(12) United States Patent
Stockley et al.

(10) Patent No.: US 11,014,912 B2
(45) Date of Patent: May 25, 2021

(54) CYANOPYRROLIDINE DERIVATIVES WITH ACTIVITY AS INHIBITORS OF USP30

(71) Applicant: MISSION THERAPEUTICS LIMITED, Cambridge (GB)

(72) Inventors: Martin Lee Stockley, Cambridge (GB); Mark Ian Kemp, Cambridge (GB); Andrew Madin, Cambridge (GB); Michael David Woodrow, Cambridge (GB); Alison Jones, Cambridge (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 0 days.

(21) Appl. No.: 16/334,836

(22) PCT Filed: Sep. 27, 2017

(86) PCT No.: PCT/GB2017/052880
§ 371 (c)(1),
(2) Date: Mar. 20, 2019

(87) PCT Pub. No.: WO2018/060689
PCT Pub. Date: Apr. 5, 2018

(65) Prior Publication Data
US 2020/0017480 A1  Jan. 16, 2020

(30) Foreign Application Priority Data

Sep. 27, 2016 (GB) ...................................... 1616348
Jun. 21, 2017 (GB) ...................................... 1709919

(51) Int. Cl.
*C07D 403/14* (2006.01)
*C07D 403/06* (2006.01)
*C07D 413/12* (2006.01)
*C07D 471/04* (2006.01)

(52) U.S. Cl.
CPC ......... *C07D 403/14* (2013.01); *C07D 403/06* (2013.01); *C07D 413/12* (2013.01); *C07D 471/04* (2013.01)

(58) Field of Classification Search
CPC .. C07D 403/06; C07D 403/14; C07D 413/12; C07D 471/04
See application file for complete search history.

(56) References Cited

U.S. PATENT DOCUMENTS

2006/0281700 A1  12/2006  Baumann et al.

FOREIGN PATENT DOCUMENTS

| WO | 9811096 A1 | 3/1998 |
|---|---|---|
| WO | 0177073 A1 | 10/2001 |
| WO | 2006110884 A2 | 10/2006 |
| WO | 2006135644 A1 | 12/2006 |
| WO | 2011032291 A1 | 3/2011 |
| WO | 2013028445 A1 | 2/2013 |
| WO | 2016/046530 A1 | 3/2016 |
| WO | 2016156816 A1 | 10/2016 |
| WO | 2017/009650 A1 | 1/2017 |
| WO | 2017/093718 A1 | 6/2017 |
| WO | 2017/109488 A1 | 6/2017 |
| WO | 2017103614 A1 | 6/2017 |
| WO | 2017/141036 A1 | 8/2017 |
| WO | 2017/149313 A1 | 9/2017 |
| WO | 2017/158381 A1 | 9/2017 |
| WO | 2017/158388 A1 | 9/2017 |
| WO | 2017/163078 A1 | 9/2017 |
| WO | 2018060689 A1 | 4/2018 |
| WO | 2018060691 A1 | 4/2018 |
| WO | 2018060742 A1 | 4/2018 |
| WO | 2018065768 A1 | 4/2018 |
| WO | 2018220355 A1 | 12/2018 |
| WO | 2018234775 A1 | 12/2018 |

OTHER PUBLICATIONS

Cancer and Metastasis Reviews (1998), 17(1), 91-106.*
Science (1999), vol. 286, 531-537.*
Ward et al., "Quantitative Chemical Proteomic Profiling of Ubiquitin Specific Proteases in Intact Cancer Cells," ACS Chem. Biol. 2016, 11, 3268-3272.
The International Search Report and Written Opinion, dated Nov. 16, 2017, in the corresponding PCT Appl. No. PCT/GB2017/052880.
Falgueyret et al., "Novel, Nonpeptidic Cyanamides as Potent and Reversible Inhibitors of Human Cathepsins K and L," J. Med. Chem. 2001, 44, 94-104.
Laine et al., "Discovery of Novel Cyanamide-Based Inhibitors of Cathepsin C," ACS Med. Chem. Lett. 2011, 2, 142-147.
Komander et al, "Breaking the chains: structure and function of the deubiquitinases", Nature Reviews Molecular Cell Biology, 10, 550-563, 2009.
Rydzewski et al, "Peptidic 1-Cyanopyrrolidines: Synthesis and SAR of a Series of Potent, Selective Cathepsin Inhibitors", Bioorganic & Medicinal Chemistry 10 (2002) 3277-3284.
Deaton et al, "Novel and potent cyclic cyanamide-based cathepsin K inhibitors", Bioorganic & Medicinal Chemistry Letters 15 (2005) 1815-1819.
Oballa et al, "A generally applicable method for assessing the electrophilicity and reactivity of diverse nitrile-containing compounds", Bioorganic & Medicinal Chemistry Letters 17 (2007) 998-1002.

(Continued)

*Primary Examiner* — Rebecca L Anderson

(57) ABSTRACT

The present invention relates to substituted-cyanopyrrolidines of Formula (I) with activity as inhibitors of deubiquitilating enzymes, in particular, ubiquitin C-terminal hydrolase 30 or ubiquitin specific peptidase 30 (USP30), having utility in a variety of therapeutic areas including cancer and conditions involving mitochondrial dysfunction. (I)

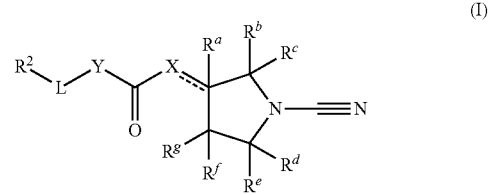

17 Claims, No Drawings

(56) References Cited

OTHER PUBLICATIONS

Zapf et al, "Covalent Inhibitors of Interleukin-2 Inducible T Cell Kinase (Itk) with Nanomolar Potency in a Whole-Blood Assay", J. Med. Chem. 2012, 55, 10047-10063.
Nakamura et al, "Regulation of Mitochondrial Morphology by USP30, a Deubiquitinating Enzyme Present in the Mitochondrial Outer Membrane", Molecular Biology of the Cell, vol. 19, 1903-1911, May 2008.
Bingol et al, "The mitochondrial deubiquitinase USP30 opposes parkin-mediated mitophagy", Nature vol. 510, 370-375, 2014.
Liang et al, "USP30 deubiquitylates mitochondrial Parkin substrates and restricts apoptotic cell death", EMBO Reports, 1-10, 2015; DOI 10.15252/embr.201439820.
Bedford et al., "Ubiquitin-like protein conjugation and the ubiquitin—proteasome system as drug targets," Nat Rev Drug Discov. Jan. 2011;10(1):29-46.

* cited by examiner

CYANOPYRROLIDINE DERIVATIVES WITH ACTIVITY AS INHIBITORS OF USP30

CROSS-REFERENCE TO RELATED APPLICATIONS

This application is a National Stage Application of PCT/GB2017/052880 filed Sep. 27, 2017, which claims priority from UK Patent Application No. 1616348.7 filed on Sep. 27, 2016 and UK Patent Application No. 1709919.3, filed on Jun. 21, 2017. The priority of said PCT and UK Patent Applications are claimed.

The present invention relates to a class of substituted-cyanopyrrolidines with activity as inhibitors of deubiquitilating enzymes, in particular, ubiquitin C-terminal hydrolase 30 or ubiquitin specific peptidase 30 (USP30), uses thereof, processes for the preparation thereof and composition containing said inhibitors. These inhibitors have utility in a variety of therapeutic areas including cancer and conditions involving mitochondrial dysfunction.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein by deubiquitylating enzymes (DUBs), of which there are approximately 95 DUBs in human cells, divided into sub-families based on sequence homology. The USP family are characterised by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently, deubiquitylating enzymes remained elusive. USP30 is a 517 amino acid protein which is found in the mitochondrial outer membrane (Nakamura et al., Mol Biol 19:1903-11, 2008). It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy.

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amylotrophic Lateral Sclerosis (ALS), multiple sclerosis), cancer, diabetes, metabolic disorders, cardio-vascular diseases, psychiatric diseases (e.g. Schizophrenia), and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death. USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteaseome, such as DUBs, are predicted to be better tolerated (Bedford et al., Nature Rev 10:29-46, 2011).

Accordingly, there is a need for compounds that are inhibitors of USP30 for the treatment of indications where inhibition of USP30 is indicated.

In accordance with a first aspect of the invention there is provided a compound of formula (I):

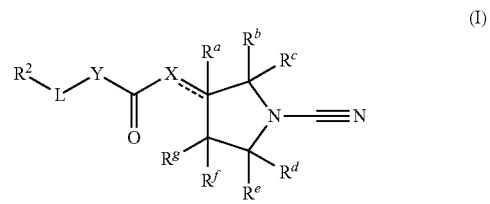

(I)

a tautomer thereof, or a pharmaceutically acceptable salt of said compound or tautomer, wherein:

⁓⁓⁓ represents a single or double bond;
when ⁓⁓⁓ is a double bond, $R^a$ does not exist;
when ⁓⁓⁓ is a double bond, X represents $C(R^x)$;
when ⁓⁓⁓ is a single bond, X represents $C(R^x)(R^y)$;
$R^x$ and $R^y$ are each independently selected from hydrogen or optionally substituted $C_1$-$C_3$ alkyl;
or $R^x$ and $R^y$ together form an optionally substituted $C_3$-$C_6$ cycloalkyl ring;
$R^a$ is selected from hydrogen, fluoro, cyano, optionally substituted $C_1$-$C_3$ alkyl, optionally substituted $C_1$-$C_3$ alkoxy, or $R^a$ is linked to $R^b$ or $R^g$ to form an optionally substituted $C_3$-$C_4$ cycloalkyl ring;

$R^b$, $R^c$, $R^d$ and $R^e$ each independently represent hydrogen, an optionally substituted $C_1$-$C_3$ alkyl; one or more spirocyclic groups where $R^b$ is linked to $R^c$, or $R^d$ is linked to $R^e$; or $R^b$ is linked to $R^a$ to form an optionally substituted $C_3$-$C_4$ cycloalkyl ring; or $R^e$ is linked to $R^f$ to form an optionally substituted $C_3$-$C_4$ cycloalkyl ring;

$R^f$ and $R^g$ are each independently selected from hydrogen, fluoro, cyano, optionally substituted $C_1$-$C_3$ alkyl, optionally substituted $C_1$-$C_3$ alkoxy, and optionally substituted 3 to 6 membered cycloalkyl, heterocyclyl, aryl or heteroaryl ring; or $R^f$ is linked to $R^e$ to form an optionally substituted $C_3$-$C_4$ cycloalkyl ring;

or $R^g$ is linked to $R^a$ to form an optionally substituted $C_3$-$C_4$ cycloalkyl ring;

or $R^g$ and $R^f$ together form a spirocyclic group;

Y is selected from $N(R^1)$, $N(R^1)$azetidinyl, and

wherein

is a 4 to 10 membered monocyclic or bicyclic heterocyclyl ring;

L is selected from a covalent bond and a linking moiety;

$R^1$ is selected from hydrogen and optionally substituted $C_1$-$C_3$ alkyl;

$R^2$ is a 5 to 10 membered, monocyclic or bicyclic, aryl or heteroaryl ring, which may be unsubstituted or substituted with one or more $Q^1(R^3)_n$ which may be the same or different;

n is 0 or 1;

$Q^1$ is selected from $Q^{1a}$ and $Q^{1b}$;

$Q^{1a}$ is selected from halo, cyano, nitro, hydroxyl, $SR^4$, $NR^4R^5$, $CONR^4R^5$, $C_0$-$C_3$ alkylene-$NR^4COR^5$, $NR^4CONR^5R^6$, $COR^4$, $C(O)OR^4$, $SO_2R^4$, $SO_2NR^4R^5$, $NR^4SO_2R^5$, $NR^4SO_2NR^5R^6$, $NR^4C(O)OR^5$, optionally substituted $C_1$-$C_6$ alkyl, optionally substituted $C_1$-$C_6$ alkoxy, halo($C_1$-$C_6$ alkyl), halo($C_1$-$C_6$ alkoxy), and optionally substituted $C_2$-$C_6$ alkenyl;

$Q^{1b}$ is selected from a covalent bond, an oxygen atom, a sulphur atom, $OR^7$, SO, $SO_2$, CO, $C(O)O$, $C_0$-$C_3$-alkylene-$C(O)NR^4$—$C_0$-$C_3$ alkylene, $C_0$-$C_3$-alkylene-$NR^4$—$C_0$-$C_3$ alkylene, $C_0$-$C_3$-alkylene-$NR^4C(O)$—$C_0$-$C_3$ alkylene, $NR^4CONR^5$, $SO_2NR^4$, $NR^4SO_2$, $NR^4SO_2NR^5$, $NR^4C(O)O$, $NR^4C(O)OR^7$, optionally substituted $C_1$-$C_6$ alkylene, and optionally substituted $C_2$-$C_6$ alkenylene;

$R^3$ is a 3 to 10 membered, monocyclic or bicyclic, heterocyclyl, heteroaryl, cycloalkyl, or aryl ring;

$R^4$, $R^5$ and $R^6$ are each independently selected from hydrogen and optionally substituted $C_1$-$C_6$ alkyl;

$R^7$ is optionally substituted $C_1$-$C_6$ alkylene;

wherein $R^3$ may be unsubstituted or substituted with one or more substituents selected from halo, cyano, oxo, nitro, hydroxyl, $SR^8$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{11}$, $Q^{2a}$-O-$Q^{2b}$-$R^{11}$, $Q^{2a}$-S-$Q^{2b}$-$R^{11}$, $Q^{2a}$-SO-$Q^{2b}$-$R^{11}$, $Q^{2a}$-$NR^8CONR^9R^{10}$, $Q^{2a}$-$NR^8CONR^9$-$Q^{2a}$-$R^{11}$, $Q^{2a}$-$NR^8R^9$, $Q^{2a}$-NR-$Q^{2b}$-$R^{11}$, $Q^{2a}$-$COR^8$-$Q^{2a}$-$CO$-$Q^{2b}$-$R^{11}$, $Q^{2a}$-$NR^8COR^9$-$Q^{2a}$-$NR^8CO$-$Q^{2b}$-$R^{11}$, $Q^{2a}$-$NR^8C(O)OR^9$, $Q^{2a}$-$NR^8C(O)O$-$Q^{2b}$-$R^{11}$, $Q^{2a}$-$SO_2R^8$, $Q^{2a}$-$SO_2$-$Q^{2b}$-$R^{11}$, $Q^{2a}$-$CONR^8R^9$, $Q^{2a}$-$CONR^8$-$Q^{2b}$-$R^{11}$, $Q^{2a}$-$CO_2R^8$, $Q^{2a}$-$CO_2$-$Q^{2b}$-$R^{11}$, $Q^{2a}$-$SO_2NR^8R^9$, $Q^{2a}$-$SO_2NR^8$-$Q^{2b}$-$R^{11}$, $Q^{2a}$-$NR^8SO_2R^9$, $Q^{2a}$-$NR^8SO_2$-$Q^{2b}$-$R^{11}$, $Q^{2a}$-$NR^8SO_2NR^9R^{10}$, and $Q^{2a}$-$NR^8SO_2NR^9$-$Q^{2b}$-$R^{11}$;

$Q^{2a}$ and $Q^{2b}$ are each independently selected from a covalent bond, optionally substituted $C_1$-$C_6$ alkylene, and optionally substituted $C_2$-$C_6$ alkenylene;

$R^8$, $R^9$ and $R^{10}$ are each independently selected from hydrogen and optionally substituted $C_1$-$C_6$ alkyl;

and $R^{11}$ is an optionally substituted 3 to 10 membered heterocyclyl, heteroaryl, aryl or cycloalkyl ring.

Unless otherwise indicated, the term substituted means substituted by one or more defined groups. In the case where groups may be selected from more than one alternatives, the selected groups may be the same or different. The term independently means that where more than one substituent is selected from more than one possible substituents, those substituents may be the same or different.

In the context of the present specification, unless otherwise stated an alkyl, alkylene, alkoxy, alkenyl, alkenylene or alkynyl substituent (or linker) group or an alkyl, alkenyl moiety in a substituent group may be linear or branched. Alkyl, alkylene, alkenyl and alkenylene chains may also include intervening heteroatoms such as oxygen.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl and $C_1$-$C_3$ alkyl within the definitions of $R^x$, $R^y$, $R^a$, $R^b$, $R^c$, $R^d$, $R^e$, $R^f$, $R^g$, $R^1$, $R^4$, $R^5$, $R^6$, $R^8$, $R^9$, $R^{10}$, $Q^{1a}$, and within the definition of substituents for $R^3$, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A $C_x$-$C_y$ alkylene group or moiety may be linear or branched and refers to a divalent hydrocarbon group having one less hydrogen atom from $C_x$-$C_y$ alkyl as defined above. $C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, $C_0$-$C_3$ alkylene, $C_1$-$C_6$ alkylene and $C_1$-$C_3$ alkylene within the definitions of $Q^{1a}$, $Q^{1b}$, $R^7$, $Q^{2a}$, $Q^{2b}$ and L, may be unsubstituted or substituted with one or more of the substituents defined herein.

$C_2$-$C_6$ alkenyl refers to a linear or branched hydrocarbon chain radical containing at least two carbon atoms and at least one double bond and includes $C_2$-$C_4$ alkenyl. Examples of alkenyl groups include ethenyl, propenyl, 2-propenyl, 1-butenyl, 2-butenyl, 1-hexenyl, 2-methyl-1-propenyl, 1,2- butadienyl, 1,3-pentadienyl, 1,4-pentadienyl and 1-hexadienyl. Unless stated otherwise, $C_2$-$C_6$ alkenyl within the definitions of $Q^{1a}$ and within the definition of substituents for $R^3$, may be unsubstituted or substituted with one or more of the substituents defined herein.

$C_2$-$C_6$ alkenylene refers to a linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene within the definition of substituents for $Q^{1b}$, $Q^{2a}$ and $Q^{2b}$, may be unsubstituted or substituted with one or more of the substituents defined herein.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl, within the definitions of substituents for $R^3$, may be unsubstituted or substituted with one or more of the substituents defined herein.

$C_1$-$C_6$ alkoxy refers to a group or part of a group having an O—$C_x$-$C_y$ alkyl group according to the definition of $C_x$-$C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, iso-propoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus the alkoxy may be linked through carbon to the remainder of the molecule, for example, $CH_2CH_2OCH_3$, or alternatively, the alkoxy is linked through oxygen to the remainder of the molecule, for example $OC_{1-6}$ alkyl. In one instance, the alkoxy is linked through oxygen to the remainder of the molecule but the alkoxy group contains a further oxygen atom, for example $OCH_2CH_2OCH_3$. Unless specified otherwise, $C_1$-$C_6$ alkoxy and $C_1$-$C_3$ alkoxy within the definitions of $R^a$, $R^f$, $R^g$, $Q^{1a}$, and within the definition of substituents for $R^3$, may be unsubstituted or substituted with one or more of the substituents defined herein. Examples of substituted $C_1$-$C_6$ alkoxy therefore include $OCF_3$, $OCHF_2$, $OCH_2CF_3$, $CH_2CH_2OCH_3$ and $CH_2CH_2OCH_2CH_3$.

The term halo refers to chloro, bromo, fluoro or iodo, in particular chloro or fluoro.

Haloalkyl and haloalkoxy groups may contain one or more halo substituents.

Examples are trifluoromethyl and trifluoromethoxy.

The term "oxo" means =O.

The term "nitro" means $NO_2$ and includes $SF_5$ (a known mimetic of nitro).

Cycloalkyl, heterocyclyl, aryl and heteroaryl rings disclosed herein and within the definitions of $R^x$, $R^y$, $R^a$, $R^b$, $R^c$, $R^d$, $R^e$, $R^f$, $R^g$, $R^2$, $R^3$, $R^{11}$ and Y may be monocyclic or bicyclic. Bicyclic ring systems include bridged, fused and spiro ring systems. In particular, the bicyclic ring systems are fused ring systems. A substituent if present may be attached to any suitable ring atom which may be a carbon atom or, in the case of heteroaryl and heterocyclyl ring systems, a heteroatom.

"cycloalkyl" refers to a monocyclic saturated or partially unsaturated, non-aromatic ring, wherein all of the ring atoms are carbon, and having the number of ring atoms as indicated. For example $C_3$-$C_{10}$ cycloalkyl refers to a monocyclic or bicyclic hydrocarbon ring containing 3 to 10 carbon atoms. Examples of $C_3$-$C_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of $R^x$, $R^y$, $R^a$, $R^b$, $R^c$, $R^d$, $R^e$, $R^f$, $R^g$, $R^3$ and $R^{11}$, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl and naphthyl. Bicyclic rings may be fused aromatic rings where both rings are aromatic, for example, naphthalenyl. Preferred aryl groups are phenyl and naphthyl, more preferably phenyl. Unless specified otherwise, aryl within the definitions of $R^f$, $R^g$, $R^2$, $R^3$ and $R^{11}$, may be unsubstituted or substituted with one or more of the substituents defined herein.

"Heteroaryl" as used herein means a polyunsaturated, monocyclic or bicyclic 5 to 10 membered aromatic moiety containing at least one and up to 5 heteroatoms, particularly 1, 2 or 3 heteroatoms selected from N, O and S, and the remaining ring atoms are carbon atoms. Heteroaryl ring nitrogen and sulphur atoms are optionally oxidised, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. Examples of fused rings where one of the rings is aromatic and the other is at least partially saturated include tetrahydropyroidopyrazinyl, tetrahydroquinolinyl and tetrahydroisoquinolinyl. In such instances, attachment of the bicyclic ring to the group it is a substituent of, e.g. Y via L, is from the aromatic ring. In particular examples, a bicyclic heteroaryl is one in which the entire fused ring system is aromatic. A bicyclic heteroaryl can have the at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heteroaryl to the group it is a substituent of can be via a carbon atom or a heteroatom (e.g. nitrogen). In instances where $R^2$ is a heteroaryl, the ring is an aromatic ring and may be fused to a further aromatic or partially saturated ring. Examples include pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, tetrahydropyridopyrazinyl and tetraydroquinolinyl, tetrahydroisoquinolinyl. Unless specified otherwise, heteroaryl within the definitions of $R^f$, $R^g$, $R^2$, $R^3$ and $R^{11}$, may be unsubstituted or substituted with one or more of the substituents defined herein.

"Heterocyclyl" as used herein in describing a ring means, unless otherwise stated, a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members or 5 to 10 members, where at least one member and up to 5 members, particularly 1, 2 or 3 members of the ring are heteroatoms selected from N, O and S, and the remaining ring atoms are carbon atoms, in stable combinations known to those of skill in the art. Heterocyclyl ring nitrogen and sulphur atoms are optionally oxidised, and the nitrogen atoms(s) are optionally quaternized. As used herein, the heterocyclyl ring may be a fused ring to another ring system to form a bicycle, i.e. one or two of the heterocyclyl ring carbons is common to an additional ring system. In instances where the heterocylcyl is a bicyclic ring, the second ring can be aromatic, e.g. a fused phenyl, pyridyl, pyrazolyl, or the like. The heterocyclyl may be linked through carbon or a heteroatom to the remainder of the molecule and in instances where the heterocyclyl is a bicyclic ring, the link may be via the heteroatom containing ring or the fused ring. In instances where the heterocyclyl is a bicyclic ring where the second ring is aromatic, e.g. tetrahydropyridopyrazinyl, tetrahydroquinolinyl or tetrahydroisoquinolinyl, attachment of the bicyclic ring to the group it is a substituent of, e.g. Y via L, is from the heterocyclcyl ring. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydropyrrolopyridinyl, dihydrobenzoxazinyl, pyrrolopyridinyl, dihydronaphthyridinyl, dihydroisoquinolinyl and tetrahydroisoquinolinyl. Unless specified otherwise, heterocyclyl within the definitions of $R^x$, $R^y$, $R^f$, $R^g$, Y, $R^3$ and $R^{11}$, may be unsubstituted or substituted with one or more of the substituents defined herein.

"Optionally substituted" as applied to any group means that the said group may if desired be substituted with one or more substituents (e.g., 1, 2, 3 or 4 substituents) which may be the same or different.

Examples of suitable substituents for "substituted" and "optionally substituted" $C_1$-$C_6$ alkyl (including $C_1$-$C_4$ alkyl, $C_1$-$C_3$ alkyl and $C_1$-$C_2$ alkyl) and $C_1$-$C_6$ alkoxy (including $C_1$-$C_4$ alkoxy, $C_1$-$C_3$ alkoxy and $C_1$-$C_2$ alkoxy) and $C_2$-$C_6$ alkenyl (including $C_2$-$C_4$ alkenyl) and $C_2$-$C_6$ alkynyl (including $C_2$-$C_4$ alkynyl), for example, within the definitions of $R^x$, $R^y$, $R^a$, $R^b$, $R^c$, $R^d$, $R^e$, $R^f$, $R^g$, $R^1$, $R^4$, $R^5$, $R^6$, $R^8$, $R^9$, $R^{10}$, $Q^{1a}$, and within the definition of substituents for $R^3$, and $C_1$-$C_6$ alkylene (including $C_1$-$C_3$ alkylene) and $C_2$-$C_6$ alkenylene, for example, within the definitions of $Q^{1a}$, $Q^{1b}R^7$, $Q^{2a}$, $Q^{2b}$ and L, include $C_1$-$C_6$ alkoxy, halo, hydroxyl, thiol, cyano, amino and nitro, in particular, halo (preferably fluoro or chloro), hydroxyl and cyano.

Examples of suitable substituents for "substituted" and "optionally substituted" rings, i.e. cycloalkyl, heterocyclyl, aryl and heteroaryl rings, for example, within the definitions of $R^x$, $R^y$, $R^a$, $R^b$, $R^c$, $R^d$, $R^e$, $R^f$, $R^g$, $R^2$, $R^3$ and $R^{11}$, include halo, cyano, oxo, nitro, amino, amide, hydroxy, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, mono-$C_{1-3}$ carbamoyl, di-$C_{1-3}$ carbamoyl or any of the above in which a hydrocarbyl moiety is itself substituted by halo, in particular fluoro, hydroxyl, cyano, amino or nitro. In groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and S(O)$_2$-alkyl.

Examples of suitable substituents for "substituted" and "optionally substituted" rings include in particular, halo, oxo, cyano, $C_1$-$C_3$ alkyl, $C_1$-$C_3$ alkoxy, heterocyclyl, cycloalkyl, heteroary or aryl, wherein the alkyl or alkoxy is optionally substituted with one or more (e.g. one, two or three) substituents selected from $C_1$-$C_6$ alkoxy, halo, hydroxyl, thiol, cyano, amino and nitro. In particular, suitable substituents for "substituted" and "optionally substituted" rings disclosed herein include fluoro, chloro, oxo, cyano, $C_1$-$C_3$ alkyl, $C_1$-$C_3$ alkoxy, wherein the alkyl or alkoxy is optionally substituted with one or more (e.g. one, two or three) substituents selected from $C_1$-$C_6$ alkoxy, halo, hydroxyl, thiol, cyano, amino and nitro, in particular, one or more fluoro.

Substituted groups thus include for example Br, Cl, F, CN, Me, Et, Pr, i-Bu, OMe, OEt, OPr, $C(CH_3)_3$, $CH(CH_3)_2$, $CF_3$, $OCF_3$, $C(O)NHCH_3$, cyclopropyl, phenyl, etc. In the case of aryl groups, the substitutions may be in the form of rings from adjacent carbon atoms in the aryl ring, for example cyclic acetals such as O—$CH_2$—O.

In preferred embodiments of the first aspect of the invention there is provided a compound of formula (I) wherein X, L, Y, $R^a$, $R^b$, $R^c$, $R^d$, $R^e$, $R^f$, $R^g$, and $R^2$, are as defined in respect of the first aspect of the invention; a tautomer thereof, or a pharmaceutically acceptable salt of said compound or tautomer; and wherein said substituents may be preferably selected as follows:

Preferably, $R^x$ is selected from hydrogen and $C_1$-$C_3$ alkyl, which may be unsubstituted or substituted with one or more substituents selected from $C_1$-$C_6$ alkoxy, halo, hydroxyl, thiol, cyano, amino and nitro, and in particular, fluoro or chloro, hydroxyl and cyano.

Preferably, $R^y$ is selected from hydrogen and $C_1$-$C_3$ alkyl, which may be unsubstituted or substituted with one or more substituents selected from $C_1$-$C_6$ alkoxy, halo, hydroxyl, thiol, cyano, amino and nitro, and in particular, fluoro or chloro, hydroxyl and cyano.

Alternatively, $R^x$ and $R^y$ may together form a $C_3$-$C_6$ cycloalkyl ring, which may be unsubstituted or substituted with a substituent selected from $C_1$-$C_3$ alkyl, $C_1$-$C_3$ alkoxy, halo, cyano, oxo, nitro, amino, amido and hydroxyl, wherein the alkyl and alkoxy may be optionally substituted with halo.

Preferably, $R^a$ is selected from hydrogen, fluoro, cyano, $C_1$-$C_3$ alkyl, and $C_1$-$C_3$ alkoxy, wherein said alkyl and alkoxy may be unsubstituted or substituted with one or more substituents selected from $C_1$-$C_6$ alkoxy, halo, hydroxyl, thiol, cyano, amino and nitro, in particular halo (preferably fluoro or chloro), hydroxyl or cyano.

Preferably, $R^b$, $R^c$, $R^d$ and $R^e$ are each independently selected from hydrogen and $C_1$-$C_3$ alkyl, which may be unsubstituted or substituted with one or more substituents selected from $C_1$-$C_6$ alkoxy, halo, hydroxyl, thiol, cyano, amino and nitro.

Preferably, $R^f$ and $R^g$ are each independently selected from hydrogen, fluoro, cyano, $C_1$-$C_3$ alkyl, $C_1$-$C_3$ alkoxy, and a 3 to 6 membered cycloalkyl, heterocyclyl, aryl or heteroaryl ring; wherein said alkyl, alkoxy, cycloalkyl, heterocyclyl, aryl and heteroaryl rings may be unsubstituted or substituted with one or more substituents selected from $C_1$-$C_6$ alkoxy, halo, hydroxyl, thiol, cyano, amino and nitro.

In an alternative embodiment, $R^b$ and $R^c$ may together form a spirocyclic ring. In addition, or alternatively, $R^d$ and $R^e$ may together form a spirocyclic ring. In addition, or alternatively, $R^f$ and $R^g$ may together form a spirocyclic ring. In such instances, preferably only one of $R^b/R^c$, $R^d/R^e$ and $R^f/R^g$ form a spirocyclic ring, wherein the remaining groups are as defined above, and in particular each of the remaining $R^a$, $R^b$, $R^c$, $R^d$, $R^e$, $R^f$, and $R^g$ groups is hydrogen.

The spirocyclic rings may contain 3, 4, 5 or 6 carbon ring atoms, in particular 3 or 4 carbon ring atoms, and may be unsubstituted or substituted with a substituent selected from $C_1$-$C_3$ alkyl, $C_1$-$C_3$ alkoxy, halo, cyano, oxo, nitro, amino, amido, hydroxyl, and nitro, wherein alkyl and alkoxy may be optionally substituted with halo.

Neighbouring R groups selected from $R^a$, $R^b$, $R^c$, $R^d$, $R^e$, $R^f$, and $R^g$ attached to the carbon ring atoms of the cyanopyrrolidine core may together form an optionally substituted $C_3$-$C_4$ cycloalkyl ring. For example, $R^a$ together with $R^b$ or $R^g$, or $R^f$ together with $R^e$. In such instances, preferably one $C_3$-$C_4$ cycloalkyl group is present whilst the remaining R groups are as defined above, in particular each of the remaining $R^a$, $R^b$, $R^c$, $R^d$, $R^e$, $R^f$, and $R^g$ groups is hydrogen. The $C_3$-$C_4$ cycloalkyl ring may be unsubstituted or substituted with a substituent selected from halo, cyano, oxo, nitro, amino, amido, hydroxyl, $C_1$-$C_6$ alkyl or $C_1$-$C_3$ alkyl, $C_1$-$C_6$ alkoxy or $C_1$-$C_3$ alkoxy, wherein the alkyl and alkoxy may be optionally substituted with halo.

Preferably, Y is selected from $N(R^1)$, $N(R^1)$azetidinyl, and

wherein

is a 4 to 10 membered monocyclic or bicyclic heterocyclyl ring; wherein $R^1$ is selected from hydrogen and optionally substituted $C_1$-$C_3$ alkyl; and said ring may be optionally substituted with one or more substituents independently selected from halo, oxo, cyano, $C_1$-$C_3$ alkyl, and $C_1$-$C_3$ alkoxy, wherein the alkyl and alkoxy may be optionally substituted with halo. When Y is a 4 to 10 membered heterocyclyl ring, the ring nitrogen is directly attached to the adjacent carbonyl.

Preferably, L is selected from a covalent bond, an oxygen atom, and $C_1$-$C_3$ alkylene, which may be optionally substituted by halo or hydroxyl, with the proviso that L cannot represent an oxygen atom when Y represents $N(R^1)$.

Preferably, $R^2$ is a 5 to 10 membered (e.g. 5, 6, 7, 8, 9 or 10 membered) ring, wherein the ring is an optionally substituted monocyclic or bicyclic aryl or heteroaryl ring. The aryl or heteroaryl ring may be attached directly to Y or may be attached via a linker, i.e. when L is not a covalent bond. When the $R^2$ ring is bicyclic, the second ring (i.e. the ring not attached to Y, either directly or via a linker) may be aromatic or partly unsaturated and thus whilst not every atom in the 5 to 10 heteroaryl or aryl ring need be in an aryl system, there must be at least one aryl or heteroaryl ring within the 5 to 10 atoms.

More preferably, $R^2$ is a 5 to 10 membered monocyclic or bicyclic aryl or heteroaryl ring and when substituted, may be substituted with one or more (e.g. one, two, three or four) of $Q^1(R^3)_n$, in particular one or two of $Q^1(R^3)_n$.

When n is 0, $Q^1$ represents $Q^{1a}$; and when n is 1, $Q^1$ represents $Q^{1b}$.

Preferably, $Q^{1a}$ is selected from halo, cyano, nitro, hydroxyl, $SR^4$, $NR^4R^5$, $CONR^4R^5$, $C_0$-$C_3$-alkylene-$NR^4COR^5$, $NR^4CONR^5R^6$, $COR^4$, $C(O)OR^4$, $SO_2R^4$, $SO_2NR^4R^5$, $NR^4SO_2R^5$, $NR^4SO_2NR^5R^6$, $NR^4C(O)OR^5$, optionally substituted $C_1$-$C_6$ alkyl, optionally substituted $C_1$-$C_6$ alkoxy, optionally substituted halo($C_1$-$C_6$ alkyl), optionally substituted halo($C_1$-$C_6$ alkoxy), and optionally substituted $C_2$-$C_6$ alkenyl; wherein the alkyl, alkoxy and alkenyl may be unsubstituted or substituted with a group selected from $C_1$-$C_6$ alkoxy, halo, hydroxyl, thiol, cyano, amino and nitro.

Preferably, $Q^{1b}$ is selected from a covalent bond, an oxygen atom, a sulphur atom, $OR^7$, SO, $SO_2$, CO, C(O)O, $C_0$-$C_3$ alkylene-C(O)$NR^4$—$C_0$-$C_3$ alkylene, $C_0$-$C_3$ alkylene-$NR^4$—$C_0$-$C_3$ alkylene, $C_0$-$C_3$-alkylene-$NR^4C(O)$—$C_0$-$C_3$ alkylene, $NR^4CONR^5$, $SO_2NR^4$, $NR^4SO_2$, $NR^4SO_2NR^5$, $NR^4C(O)O$, $NR^4C(O)OR^7$, optionally substituted $C_1$-$C_6$ alkylene and optionally substituted $C_2$-$C_6$ alkenylene; wherein the alkylene or alkenylene may be unsubstituted or substituted with a group selected from $C_1$-$C_6$ alkoxy, halo, hydroxyl, thiol, cyano, amino and nitro.

Preferably, $R^4$, $R^5$ and $R^6$ are each independently selected from hydrogen and optionally substituted $C_1$-$C_6$ alkyl, which may be unsubstituted or substituted with a group selected from $C_1$-$C_6$ alkoxy, halo, hydroxyl, thiol, cyano, amino, and nitro.

Preferably, $R^7$ is $C_1$-$C_6$ alkylene, which may be unsubstituted or substituted with a group selected from $C_1$-$C_6$ alkoxy, halo, hydroxyl, thiol, cyano, amino, and nitro.

When n is 0, $Q^1$ represents $Q^{1a}$, wherein $Q^{1a}$ is selected from halo (e.g. fluoro, chloro or bromo), cyano, nitro, hydroxyl, $SR^4$, $NR^4R^5$, $CONR^4R^5$, $C_0$-$C_3$-alkylene-$NR^4COR^5$, $NR^4CONR^5R^6$, $COR^4$, $C(O)OR^4$, $SO_2R^4$, $SO_2NR^4R^5$, $NR^4SO_2R^5$, $NR^4SO_2NR^5R^6$, $NR^4C(O)OR^5$, optionally substituted $C_1$-$C_6$ alkyl, optionally substituted $C_1$-$C_6$ alkoxy and optionally substituted $C_2$-$C_6$ alkenyl. The alkyl, alkoxy or alkenyl may be unsubstituted or substituted with a group selected from $C_1$-$C_6$ alkoxy, halo, hydroxyl, thiol, cyano, amino and nitro.

Preferably, $Q^{1a}$ is selected from halo (e.g. fluoro, chloro or bromo), optionally substituted $C_1$-$C_3$ alkyl and optionally substituted $C_1$-$C_3$ alkoxy. The alkyl or alkoxy may be unsubstituted or substituted with a group selected from $C_1$-$C_6$ alkoxy, halo, hydroxyl, thiol, cyano, amino and nitro.

In particular examples, n is 0 and $R^2$ represents a 5 or 6 membered heteroaryl or aryl ring which is substituted with one or more (e.g. one, two, three or four) $Q^{1a}$ substituents independently selected from halo (e.g. fluoro or chloro), $C_1$-$C_6$ alkyl and $C_1$-$C_6$ alkoxy, wherein the alkyl and alkoxy may be unsubstituted or substituted with one or more halo, in particular fluoro.

In further examples, n is 0 and $R^2$ represents a 9 or 10 membered heteroaryl or aryl ring which is optionally substituted with one or more (e.g. one, two, three or four) $Q^{1a}$ substituents independently selected from halo (e.g. fluoro or chloro) and $C_1$-$C_6$ alkoxy.

When n is 1, $Q^1$ represents $Q^{1b}$, wherein $Q^{1b}$ is selected from a covalent bond, an oxygen atom, a sulphur atom, $OR^7$, SO, $SO_2$, CO, C(O)O, $C_0$-$C_3$-alkylene-C(O)$NR^4C_0$-$C_3$ alkylene, $C_0$-$C_3$ alkylene-$NR^4$—$C_0$-$C_3$ alkylene, $C_0$-$C_3$-alkylene-$NR^4C(O)$—$C_0$-$C_3$ alkylene, $NR^4CONR^5$, $SO_2NR^4$, $NR^4SO_2$, $NR^4SO_2NR^5$, $NR^4C(O)O$, $NR^4C(O)OR^7$, optionally substituted $C_1$-$C_6$ alkylene and optionally substituted $C_2$-$C_6$ alkenylene. The alkylene or alkenylene may be unsubstituted or substituted with a group selected from $C_1$-$C_6$ alkoxy, halo, hydroxyl, thiol, cyano, amino and nitro.

In particular examples, $Q^{1b}$ is selected from a covalent bond and an oxygen atom.

In particular examples, $R^2$ is substituted with a further ring either directly or via a linker, i.e., $R^2$ is substituted with at least one $Q^1$-$(R^3)_n$ wherein n is 1.

When n is 1, $R^3$ represents an optionally substituted 3 to 10 membered monocyclic or bicyclic heterocyclyl, heteroaryl, cycloalkyl or aryl ring (when n is 0, $Q^1$ is present and $R^3$ is absent). The heterocyclyl, heteroaryl, cycloalkyl or aryl ring may be unsubstituted or substituted.

In all cases described herein, $R^3$ may be optionally substituted with one or more substituents independently selected from halo, cyano, oxo, nitro, hydroxyl, $SR^8$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{11}$, $Q^{2a}$-O-$Q^{2b}$-$R^{11}$, $Q^{2a}$-S-$Q^{2b}$-$R^{11}$, $Q^{2a}$-SO-$Q^{2b}$-$R^{11}$, $Q^{2a}$-$NR^8CONR^9R^{10}$, $Q^{2a}$-$NR^8CONR^9$-$Q^{2a}$-$R^{11}$, $Q^{2a}$-$NR^8R_9$, $Q^{2a}$-$NR^8$-$Q^{2b}$-$R^{11}$, $Q^{2a}$-CO-$Q^{2b}$-$R^{11}$, $Q^{2a}$-$NR^8COR^9$, $Q^{2a}$-$NR^8CO$-$Q^{2b}$-$R^{11}$, $Q^{2a}$-$NR^8C(O)OR^9$, $Q^{2a}$-$NR^8C(O)O$-$Q^{2b}$-$R^{11}$, $Q^{2a}$-$SO_2R^8$, $Q^{2a}$-$SO_2$-$Q^{2b}$-$R^{11}$, $Q^{2a}$-$CONR^8R^9$, $Q^{2a}$-$CONR^8$-$Q^{2b}$-$R^{11}$, $Q^{2a}$-$CO_2R^8$-$Q^{2a}$-$CO_2$-$Q^{2b}$-$R^{11}$, $Q^{2a}$-$SO_2NR^8R^9$, $Q^{2a}$-$SO_2NR^8$-$Q^{2b}$-$R^{11}$, $Q^{2a}$-$NR^8SO_2R^9$, $Q^{2a}$-$NR^8SO_2$-$Q^{2b}$-$R^{11}$, $Q^{2a}$-$NR^8SO_2NR^9R^{10}$ and $Q^{2a}$-$NR^8SO_2NR^9$-$Q^{2b}$-$R^{11}$, wherein the alkyl, alkoxy, alkenyl or alkynyl are optionally substituted with one or more substituents selected from $C_1$-$C_6$ alkoxy, halo, hydroxyl, thiol, cyano, amino and nitro.

$Q^{2a}$ and $Q^{2b}$ each independently represent a covalent bond, optionally substituted $C_1$-$C_6$ alkylene or optionally substituted $C_2$-$C_6$ alkenylene. The alkylene or alkenylene may be unsubstituted or substituted with a group selected from $C_1$-$C_6$ alkoxy, halo, hydroxyl, thiol, cyano, amino and nitro.

$R^8$, $R^9$ and $R^{10}$ each independently represent hydrogen or optionally substituted $C_1$-$C_6$ alkyl. The alkyl may be unsubstituted or substituted with a group selected from $C_1$-$C_6$ alkoxy, halo, hydroxyl, thiol, cyano, amino and nitro.

$R^{11}$ represents an optionally substituted 3 to 10 membered heterocyclyl, heteroaryl, aryl or cycloalkyl ring. The heterocyclyl, heteroaryl, aryl or cycloalkyl may be unsubstituted or substituted. In particular, $R^{11}$ represents a $C_3$-$C_4$ cycloalkyl ring which may be unsubstituted or substituted with a substituent selected from $C_1$-$C_3$ alkyl, $C_1$-$C_3$ alkoxy, halo, cyano, oxo, nitro, amino, amido, hydroxyl, wherein the alkyl and alkoxy may be optionally substituted with halo.

In particular, $R^3$ may be optionally substituted with one or more substituents independently selected from halo, cyano, oxo, nitro, hydroxyl, $SR^8$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$NR^8CONR^9R^{10}$, $Q^{2a}$-$NR^8R^9$, $Q^{2a}$-$COR^8$, $Q^{2a}$-$NR^8COR^9$, $Q^{2a}$-$NR^8C(O)OR^9$, $Q^{2a}$-$SO_2R^8$, $Q^{2a}$-$CONR^8R^9$, $Q^{2a}$-$CO_2R^8$, $Q^{2a}$-$SO_2NR^8R^9$, $Q^{2a}$-$NR^8SO_2R^9$ and $Q^{2a}$-$NR^8SO_2NR^9R^{10}$, wherein the alkyl, alkoxy, alkenyl or alkynyl are optionally substituted with one or more substituents selected from $C_1$-$C_6$ alkoxy, halo, hydroxyl, thiol, cyano, amino and nitro;

$Q^{2a}$ and $Q^{2b}$ each independently represent a covalent bond, optionally substituted $C_1$-$C_6$ alkylene or optionally substituted $C_2$-$C_6$ alkenylene, wherein the alkylene or alkenylene may be unsubstituted or substituted with a group selected from $C_1$-$C_6$ alkoxy, halo, hydroxyl, thiol, cyano, amino and nitro; and $R^8$, $R^9$ and $R^{10}$ each independently represent hydrogen or optionally substituted $C_1$-$C_6$ alkyl, wherein the alkyl may be unsubstituted or substituted with a group selected from $C_1$-$C_6$ alkoxy, halo, hydroxyl, thiol, cyano, amino and nitro.

$R^3$ may be substituted with one or more (e.g. one, two, three or four), in particular one or two, substituents independently selected from halo, cyano, oxo, nitro, hydroxyl, $SR^8$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{11}$, $Q^{2a}$-O-$Q^{2b}$-$R^{11}$, $Q^{2a}$-S-$Q^{2b}$-$R^{11}$, $Q^{2a}$-SO-$Q^{2b}$-$R^{11}$, $Q^{2a}$-$NR^8CONR^9R^{10}$, $Q^{2a}$-$NR^8CONR^9$-$Q^{2a}$-$R^{11}$, $Q^{2a}$-$NR^8R^9$, $Q^{2a}$-$NR^8$-$Q^{2b}$-$R^{11}$, $Q^{2a}$-$COR^8$, $Q^{2a}$-CO-$Q^{2b}$-$R^{11}$, $Q^{2a}$-$NR^8COR^9$, $Q^{2a}$-$NR^8CO$-$Q^{2b}$-$R^{11}$, $Q^{2a}$-$NR^8C(O)OR^9$, $Q^{2a}$-$NR^8C(O)O$-$Q^{2b}$-$R^{11}$, $Q^{2a}$-$SO_2R^8$, $Q^{2a}$-$SO_2$-$Q^{2b}$-$R^{11}$, $Q^{2a}$-$CONR^8R^9$, $Q^{2a}$-$CONR^8$-$Q^{2b}$-$R^{11}$, $Q^{2a}$-$CO_2R^8$, $Q^{2a}$-$CO_2$-$Q^{2b}$-$R^{11}$, $Q^{2a}$-$SO_2NR^8R^9$, $Q^{2a}$-$SO_2NR^8$-$Q^{2b}$-$R^{11}$, $Q^{2a}$-$NR^8SO_2R^9$, $Q^{2a}$-$NR^8SO_2$-$Q^{2b}$-$R^{11}$, $Q^{2a}$-$NR^8SO_2NR^9R^{10}$ and $Q^{2a}$-$NR^8SO_2NR^9$-$Q^{2b}$-$R^{11}$, wherein $Q^{2a}$ and $Q^{2b}$ each independently represent a covalent bond, optionally substituted $C_1$-$C_6$ alkylene or optionally substituted $C_2$-$C_6$ alkenylene, wherein $R^8$, $R^9$ and $R^{10}$ each independently represent hydrogen or optionally substituted $C_1$-$C_6$ alkyl, and wherein $R^{11}$ represents an optionally substituted 3 to 10 membered heterocyclyl, heteroaryl, aryl or cycloalkyl, wherein any alkyl, alkoxy, alkenyl, alkynyl, alkylene or alkenylene is optionally substituted with one or more (e.g. one, two, three or four) substituents selected from $C_1$-$C_6$ alkoxy, halo, hydroxyl, thiol, cyano, amino and nitro, and any heterocyclyl, heteroaryl, aryl or cycloalkyl may be unsubstituted or substituted.

In a preferred aspect of the present invention, there is provided a compound of formula (I):

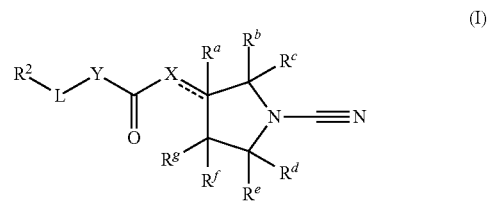

(I)

a tautomer thereof, or a pharmaceutically acceptable salt of said compound or tautomer, wherein:

⸺ represents a single or double bond;

when ⸺ is a double bond, $R^a$ does not exist;

when ⸺ is a double bond, X represents $C(R^x)$;

when ⸺ is a single bond, X represents $C(R^x)(R^y)$;

$R^x$ and $R^y$ are each independently selected from hydrogen and $C_1$-$C_3$ alkyl; or $R^x$ and $R^y$ together form a $C_3$-$C_6$ cycloalkyl ring;

$R^a$ is selected from hydrogen, fluoro, cyano, $C_1$-$C_3$ alkyl, and $C_1$-$C_3$ alkoxy;

or $R^a$ is linked to either $R^b$ or $R^g$ to form a $C_3$-$C_4$ cycloalkyl ring;

$R^b$, $R^c$, $R^d$ and $R^e$ each independently represent hydrogen, $C_1$-$C_3$ alkyl; one or more spirocyclic groups where $R^b$ is linked to $R^c$, or $R^d$ is linked to $R^e$; or $R^b$ is linked to $R^a$ to form a $C_3$-$C_4$ cycloalkyl ring; or $R^e$ is linked to $R^f$ to form a $C_3$-$C_4$ cycloalkyl ring; $R^f$ and $R^g$ are each independently selected from hydrogen, fluoro, cyano, $C_1$-$C_3$ alkyl, $C_1$-$C_3$ alkoxy, and a 3 to 6 membered cycloalkyl, heterocyclyl, aryl or heteroaryl ring; or $R^f$ is linked to $R^e$ to form a $C_3$-$C_4$ cycloalkyl ring;

or $R^g$ is linked to $R^a$ to form a $C_3$-$C_4$ cycloalkyl ring;
or $R^g$ and $R^f$ together form a spirocyclic group;
Y is selected from $N(R^1)$, $N(R^1)$azetidinyl, and

wherein

is a 4 to 10 membered, monocyclic or bicyclic, heterocyclyl ring; wherein said ring may be optionally substituted with one or more substituents independently selected from halo, oxo, cyano, $C_1$-$C_3$ alkyl, and $C_1$-$C_3$ alkoxy, wherein the alkyl and alkoxy may be optionally substituted with halo;
L is selected from a covalent bond, an oxygen atom, and $C_1$-$C_3$ alkylene, with the proviso that L cannot be an oxygen atom when Y represents $N(R^1)$;
$R^1$ is selected from hydrogen and $C_1$-$C_3$ alkyl;
$R^2$ is a 5 to 10 membered, monocyclic or bicyclic, aryl or heteroaryl ring, which may be unsubstituted or substituted with one or more $Q^1(R^3)$, which may be the same or different;
n is 0 or 1;
when n is 0, $Q^1$ represents $Q^{1a}$; and
when n is 1, $Q^1$ represents $Q^{1b}$.
$Q^{1a}$ is selected from halo, cyano, nitro, hydroxyl, $SR^4$, $NR^4R^5$, $CONR^4R^5$, $C_0$-$C_3$-alkylene-$NR^4COR^5$, $NR^4CONR^5R^6$, $COR^4$, $C(O)OR^4$, $SO_2R^4$, $SO_2NR^4R^5$, $NR^4SO_2R^5$, $NR^4SO_2NR^5R^6$, $NR^4C(O)OR^5$, $C_1$-$C_6$ alkyl, $C_1$-$C_6$ alkoxy, halo($C_1$-$C_6$ alkyl), halo($C_1$-$C_6$ alkoxy), and $C_2$-$C_6$ alkenyl; wherein said alkyl, alkoxy and alkenyl may be unsubstituted or substituted with a group selected from $C_1$-$C_6$ alkoxy, halo, hydroxyl, thiol, cyano, amino, and nitro;
$Q^{1b}$ is selected from a covalent bond, an oxygen atom, a sulphur atom, $OR^7$, $SO$, $SO_2$, $CO$, $C(O)O$, $C_0$-$C_3$ alkylene-$C(O)NR^4$—$C_0$-$C_3$ alkylene, $C_0$-$C_3$ alkylene-$NR^4$—$C_0$-$C_3$ alkylene, $C_0$-$C_3$ alkylene-$NR^4C(O)$—$C_0$-$C_3$ alkylene, $NR^4CONR^5$, $SO_2NR^4$, $NR^4SO_2$, $NR^4SO_2NR^5$, $NR^4C(O)O$, $NR^4C(O)OR^7$, $C_1$-$C_6$ alkylene, and $C_2$-$C_6$ alkenylene;
$R^3$ is a 3 to 10 membered, monocyclic or bicyclic, heterocyclyl, heteroaryl, cycloalkyl, or aryl ring;
$R^4$, $R^5$ and $R^6$ are each independently selected from hydrogen and optionally substituted $C_1$-$C_6$ alkyl;
$R^7$ is optionally substituted $C_1$-$C_6$ alkylene;
wherein $R^3$ may be unsubstituted or substituted with one or more substituents selected from halo, cyano, oxo, nitro, hydroxyl, $SR^8$, $C_1$-$C_6$ alkyl, $C_1$-$C_6$ alkoxy, halo($C_1$-$C_6$ alkyl), halo($C_1$-$C_6$ alkoxy), $C_2$-$C_6$ alkenyl, $C_2$-$C_6$ alkynyl, $Q^{2a}$-$R^{11}$, $Q^{2a}$-O-$Q^{2b}$-$R^{11}$, $Q^{2a}$-S-$Q^{2b}$-$R^{11}$, $Q^{2a}$-SO-$Q^{2b}$-$R^{11}$, $Q^{2a}$-$NR^8CONR^9R^{10}$, $Q^{2a}$-$NR^8CONR^9$-$Q^{2a}$-$R^{11}$, $Q^{2a}$-$NR^8R^9$, $Q^{2a}$-$NR^8$-$Q^{2b}$-$R^{11}$, $Q^{2a}$-$COR^8$, $Q^{2a}$-CO-$Q^{2b}$-$R^{11}$, $Q^{2a}$-$NR^8COR^9$, $Q^{2a}$-$NR^8CO$-$Q^{2b}$-$R^{11}$, $Q^{2a}$-$NR^8C(O)OR^9$, $Q^{2a}$-$NR^8C(O)O$-$Q^{2b}$-$R^{11}$, $Q^{2a}$-$SO_2R^8$, $Q^{2a}$-$SO_2$-$Q^{2b}$-$R^{11}$, $Q^{2a}$-$CONR^8R^9$, $Q^{2a}$-$CONR^9$-$Q^{2b}$-$R^{11}$, $Q^{2a}$-$CO_2R^8$, $Q^{2a}$-$CO_2$-$Q^{2b}$-$R^{11}$, $Q^{2a}$-$SO_2NR^8R^9$, $Q^{2a}$-$SO_2NR^8$-$Q^{2b}$-$R^{11}$, $Q^{2a}$-$NR^8SO_2R^9$, $Q^{2a}$-$NR^8SO_2$-$Q^{2b}$-$R^{11}$, $Q^{2a}$-$NR^8SO_2NR^9R^{10}$, and $Q^{2a}$-$NR^8SO_2NR^9$-$Q^{2b}$-$R^{11}$;
$Q^{2a}$ and $Q^{2b}$ are each independently selected from a covalent bond, $C_1$-$C_6$ alkylene, and $C_2$-$C_6$ alkenylene;
$R^8$, $R^9$ and $R^{10}$ are each independently selected from hydrogen and $C_1$-$C_6$ alkyl; and $R^{11}$ is a 3 to 10 membered, heterocyclyl, heteroaryl, aryl or cycloalkyl ring.

In preferred embodiments of the preferred aspect of the invention there is provided a compound of formula (I) wherein X, L, Y, $R^a$, $R^b$, $R^c$, $R^d$, $R^e$, $R^f$, $R^g$, and $R^2$, are as defined in respect of the first aspect of the invention and preferred embodiments thereof; a tautomer thereof, or a pharmaceutically acceptable salt of said compound or tautomer; and wherein said substituents may be preferably selected as follows:

Preferably, $R^x$ is selected from hydrogen and $C_1$-$C_3$ alkyl.
More preferably, $R^x$ is selected from hydrogen, methyl, ethyl, and propyl.
Most preferably, $R^x$ is hydrogen.
Preferably, $R^y$ is selected from hydrogen and $C_1$-$C_3$ alkyl.
More preferably, $R^y$ is selected from hydrogen, methyl, ethyl, and propyl.
Most preferably, $R^y$ is hydrogen.
Alternatively, $R^x$ and $R^y$ may together form a $C_3$-$C_6$ cycloalkyl ring, and preferably, $R^x$ and $R^y$ may together form a cyclopropyl, cyclobutyl, cyclopentyl, or cyclohexyl ring.
In a more preferred embodiment, $R^x$ is hydrogen and $R^y$ is selected from methyl and ethyl. Most preferably, $R^x$ and $R^y$ are each hydrogen.
Preferably, $R^a$ is selected from hydrogen, fluoro, cyano, $C_1$-$C_3$ alkyl and $C_1$-$C_3$ alkoxy.
More preferably, $R^a$ is selected from hydrogen, fluoro, cyano, methyl, ethyl, methoxy, and ethoxy.
Yet more preferably, $R^a$ is selected from hydrogen and methyl.
Most preferably, $R^a$ is hydrogen.
Preferably, $R^b$, $R^c$, $R^d$ and $R^e$ are each independently selected from hydrogen, and $C_1$-$C_3$ alkyl.
More preferably, $R^b$, $R^c$, $R^d$ and $R^e$ are each independently selected from hydrogen, methyl and ethyl.
Yet more preferably, $R^b$, and $R^d$ are each independently selected from hydrogen and methyl; and $R^c$ and $R^e$ are each hydrogen.
Most preferably, $R^b$, $R^c$, $R^d$ and $R^e$ are each hydrogen.
Preferably, $R^f$ and $R^g$ are each independently selected from, hydrogen, fluoro, cyano, $C_1$-$C_3$ alkyl, and $C_1$-$C_3$ alkoxy.
More preferably, $R^f$ and $R^g$ are each independently selected from hydrogen, fluoro, and methyl.
Most preferably, $R^f$ and $R^g$ are each hydrogen.
Preferably, Y is selected from $N(R^1)$, $N(R^1)$azetidinyl, and

wherein

is a 4 to 10 membered monocyclic or bicyclic heterocyclyl ring, which may be optionally substituted with one or more substituents independently selected from halo, oxo, cyano, methyl, ethyl, methoxy and ethoxy.
In one preferred aspect, Y is selected from $N(R^1)$ and $N(R^1)$azetidinyl, wherein $R^1$ is selected from hydrogen and $C_1$-$C_3$ alkyl.

More preferably, R¹ is selected from hydrogen, methyl, and ethyl.

More preferably, R¹ is selected from hydrogen and methyl.

In another preferred aspect, Y is a 4, 5, or 6-membered monocyclic ring, or a 9 or 10-membered bicyclic ring, which may be optionally substituted with 1 to 4 substituents independently selected from halo, oxo, cyano, methyl, ethyl, methoxy and ethoxy.

More preferably, Y is azetidinyl, which may be optionally substituted with 1 or 2 substituents independently selected from halo and methyl.

Most preferably, Y is selected from azetidinyl, N(H) azetidinyl, N(H), and N(CH₃).

Preferably, L is selected from a covalent bond, an oxygen atom, and $C_1$-$C_3$ alkylene, with the proviso that L cannot represent an oxygen atom when Y represents N(R¹).

More preferably, L is selected from a covalent bond, an oxygen atom, methylene, and ethylene, with the proviso that L cannot represent an oxygen atom when Y represents N(R¹).

Preferably, R² is a 5 or 6 membered monocylic, or a 9 or 10-membered bicyclic, aryl or heteroaryl ring comprising 1 to 5 heteroatoms independently selected from nitrogen, oxygen, and sulfur; said rings being optionally substituted with one or more (e.g. one, two, three or four) of $Q^1$ $(R^3)_n$.

Preferably, R² may be optionally substituted with 1 or 2 of $Q^1(R^3)_n$.

Preferably, when R² is a heteroaryl ring, the ring may comprise one or more (e.g. 1, 2 or 3) heteroatoms independently selected from nitrogen, oxygen and sulphur.

Yet more preferably, the heteroaryl ring contains at least one nitrogen atom, for example, 1, 2 or 3 nitrogen atoms, preferably 1 or 2 nitrogen heteroatoms.

Even more preferably, the heteroaryl ring of R² is selected from pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, tetrahydropyridopyrazinyl, tetraydroquinolinyl, tetrahydroisoquinolinyl, phenyl, naphthyl, and naphthalenyl.

Most preferably, the heteroaryl ring of R² is selected from thiazolyl, imidazopyridinyl, phenyl, pyridinyl, benzothiazolyl, isoxazolyl, benzoxazolyl, quinolinyl, pyrazolyl, thiadiazolyl, oxadiazolyl, and pyrazolopyridine.

Examples of the preferred rings of R² include those shown below:

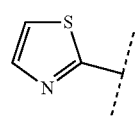

A

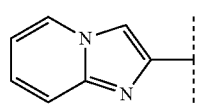

B

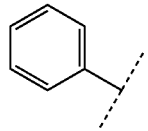

C

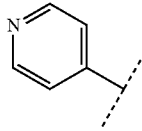

D

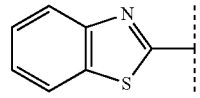

E

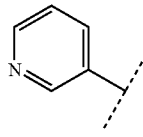

F

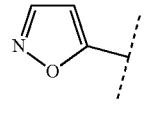

G

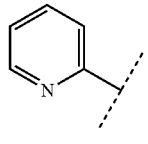

H

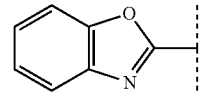

I

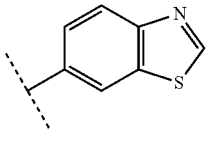

J

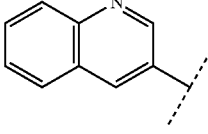

K

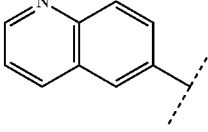

L

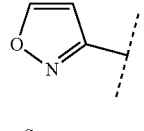

M

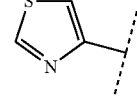

N

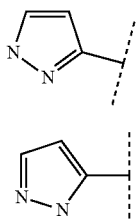

O

P wherein

represents the point of attachment to the remainder of the molecule, i.e. to Y via L, and wherein rings are optionally substituted as described herein.

In one preferred aspect, n is 0.

In another preferred aspect, n is 1.

Preferably, $Q^{1a}$ is selected from halo, cyano, nitro, hydroxyl, $SR^4$, $NR^4R^5$, $CONR^4R^5$, $C_0$-$C_3$-alkylene-$NR^4COR^5$, $NR^4CONR^5R^6$, $COR^4$, $C(O)OR^4$, $SO_2R^4$, $SO_2NR^4R^5$, $NR^4SO_2R^5$, $NR^4SO_2NR^5R^6$, $NR^4C(O)OR^5$, $C_1$-$C_6$ alkyl, $C_1$-$C_6$ alkoxy, halo($C_1$-$C_6$ alkyl), halo($C_1$-$C_6$ alkoxy), $C_1$-$C_3$ alkoxy-$C_1$-$C_3$ alkyl, and $C_1$-$C_3$ alkoxy-$C_1$-$C_3$ alkoxy and $C_2$-$C_6$ alkenyl.

More preferably, $Q^{1a}$ is selected from halo, cyano, hydroxy, $C_1$-$C_6$ alkyl, $C_1$-$C_6$ alkoxy, halo($C_1$-$C_6$ alkyl), and halo($C_1$-$C_6$ alkoxy), $C_1$-$C_3$ alkoxy-$C_1$-$C_3$ alkyl, and $C_1$-$C_3$ alkoxy-$C_1$-$C_3$ alkoxy.

Yet more preferably, $Q^{1a}$ is selected from halo, cyano, hydroxyl, $C_1$-$C_3$ alkyl, $C_1$-$C_3$ alkoxy, halo($C_1$-$C_3$ alkyl), $CON(C_1$-$C_3$ alkyl$)_2$, and $C_1$-$C_3$ alkoxy-$C_1$-$C_3$ alkoxy.

Most preferably, $Q^{1a}$ is selected from fluoro, chloro, cyano, hydroxyl, methyl, methoxy, isopropoxy, $CF_3$, $C(O)N(CH_3)_2$, and methoxyethoxy.

Preferably, $Q^{1b}$ is selected from a covalent bond, an oxygen atom, a sulphur atom, $OR^7$, SO, $SO_2$, CO, $C(O)O$, $C_0$-$C_3$ alkylene-$C(O)NR^4$—$C_0$-$C_3$ alkylene, $C_0$-$C_3$ alkylene-$NR^4$—$C_0$-$C_3$ alkylene, $C_0$-$C_3$ alkylene-$NR^4C(O)$—$C_0$-$C_3$ alkylene, $NR^4CONR^5$, $SO_2NR^4$, $NR^4SO_2$, $NR^4SO_2NR^5$, $NR^4C(O)O$, $NR^4C(O)OR^7$, $C_1$-$C_6$ alkylene and $C_2$-$C_6$ alkenylene.

Most preferably, $Q^{1b}$ is selected from a covalent bond and an oxygen atom.

Preferably, $R^4$, $R^5$ and $R^6$ are each independently selected from hydrogen and $C_1$-$C_6$ alkyl, and more preferably selected from hydrogen and methyl.

Preferably, $R^7$ is $C_1$-$C_6$ alkylene, and more preferably methylene.

Preferably, $R^3$ is a 3 to 10-membered, monocyclic or bicyclic, heterocyclyl, heteroaryl, cycloalkyl, or aryl ring, which may be unsubstituted or substituted with one or more substituents selected from halo, cyano, oxo, nitro, hydroxyl, $SR^8$, $C_1$-$C_6$ alkyl, $C_1$-$C_6$ alkoxy, halo($C_1$-$C_6$ alkyl), halo($C_1$-$C_6$ alkoxy), $C_2$-$C_6$ alkenyl, and $C_2$-$C_6$alkynyl.

More preferably, the heterocyclyl, heteroaryl, cycloalkyl, or aryl ring of $R^3$, is a 4 to 6-membered monocyclic ring, or a 9 to 10-membered bicyclic ring.

Preferably, when $R^3$ is a heterocyclyl or heteroaryl ring, the ring may comprise one or more (e.g. 1, 2 or 3) heteroatoms independently selected from nitrogen, oxygen and sulphur.

Yet more preferably, the heterocyclyl or heteroaryl ring contains at least one nitrogen atom, for example, 1, 2 or 3 nitrogen atoms, preferably 1 or 2 nitrogen heteroatoms.

Preferably, the heterocyclyl, heteroaryl, cycloalkyl, or aryl ring of $R^3$, is selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrrolidinyl, pyrazinyl, pyrimidinyl, pyridazinyl, furanyl, thiophenyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydropyridinyl, dihydropyrrolopyridinyl, quinoxalinyl, dihydrobenzoxazinyl, tetrahydropyridopyrazinyl, tetrahydroquinolinyl, tetrahydroisoquinolinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl, pyrrolopyridinyl, dihydronaphthyridinyl, dihydroisoquinolinyl, and tetrahydroisoquinolinyl.

Most preferably, the heterocyclyl, heteroaryl, cycloalkyl, or aryl ring of $R^3$, is selected from phenyl, isoxazolyl, pyridinyl, pyrazolyl, and pyrrolidinyl.

In one preferred aspect, the ring of $R^3$, is an aryl ring, which is preferably phenyl.

In another preferred aspect, the ring of $R^3$, is a heterocyclyl ring, which is preferably pyrrolidinyl.

In another preferred aspect, the ring of $R^3$, is a heteroaryl ring, which is preferably selected from isoxazolyl, pyridinyl, and pyrazolyl.

Preferably, $R^3$ is unsubstituted or substituted with one or more (preferably, 1, 2, or 3) substituents, each independently selected from halo, cyano, oxo, nitro, hydroxyl, $SR^8$, $C_1$-$C_6$ alkyl, $C_1$-$C_6$ alkoxy, halo($C_1$-$C_6$ alkyl), halo($C_1$-$C_6$ alkoxy), $C_2$-$C_6$ alkenyl, and $C_2$-$C_6$ alkynyl.

More preferably, $R^3$ is unsubstituted or substituted with one or more (preferably, 1, 2, or 3) substituents, each independently selected from halo, cyano, hydroxyl, $C_1$-$C_4$ alkyl, $C_1$-$C_4$ alkoxy, halo($C_1$-$C_4$ alkyl), and halo($C_1$-$C_4$ alkoxy).

Yet more preferably, $R^3$ is unsubstituted or substituted with 1, 2, or 3 substituents, each independently selected from fluoro, chloro, cyano, hydroxyl, methyl, ethyl, propyl, isobutyl, tert-butyl, methoxy, ethoxy, $CF_3$, and $OCF_3$.

Yet more preferably, $R^3$ is unsubstituted or substituted with 1, 2, or 3 substituents, each independently selected from fluoro, chloro, cyano, methyl, methoxy, $CF_3$, and $OCF_3$.

Most preferably, $R^3$ is unsubstituted or substituted with 1 or 2 substituents, each independently selected from fluoro, chloro, cyano, methyl, methoxy, $CF_3$, and $OCF_3$.

In a preferred aspect of the present invention, there is provided a compound of formula (IA), which corresponds to a compound of formula (I) where ⁓ is a single bond:

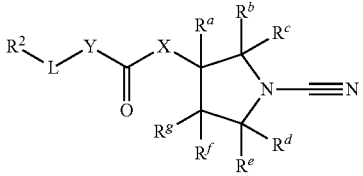

(IA)

wherein X, L, Y, $R^a$, $R^b$, $R^c$, $R^d$, $R^e$, $R^f$, $R^g$, and $R^2$, are as defined in respect of the first aspect of the invention, and preferred aspects, and embodiments thereof; a tautomer thereof, or a pharmaceutically acceptable salt of said compound or tautomer.

In an alternative preferred aspect of the present invention, there is provided a compound of formula (IB), which corresponds to a compound of formula (I) where ≈≈≈ is a double bond:

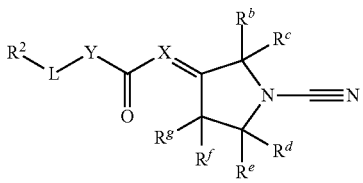

(IB)

wherein X, L, Y, $R^b$, $R^c$, $R^d$, $R^e$, $R^f$, $R^g$, and $R^2$, are as defined in respect of the first aspect of the invention, and preferred aspects, and embodiments thereof; a tautomer thereof, or a pharmaceutically acceptable salt of said compound or tautomer.

In a preferred embodiment of a compound of formula (IA), each of $R^a$, $R^b$, $R^c$, $R^d$, $R^e$, $R^f$ and $R^g$ are hydrogen, to provide a compound of formula (IC):

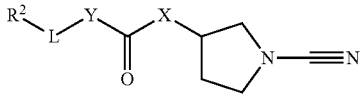

(IC)

wherein X, L, Y, and $R^2$, are as defined in respect of the first aspect of the invention, and preferred aspects, and embodiments thereof; a tautomer thereof, or a pharmaceutically acceptable salt of said compound or tautomer.

In a preferred embodiment of a compound of formula (IB), each of $R^b$, $R^c$, $R^d$, $R^e$, $R^f$ and $R^g$ are hydrogen, to provide a compound of formula (IC):

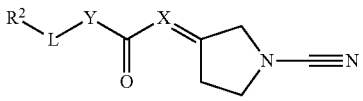

(ID)

wherein X, L, Y, and $R^2$, are as defined in respect of the first aspect of the invention, and preferred aspects, and embodiments thereof; a tautomer thereof, or a pharmaceutically acceptable salt of said compound or tautomer.

According to one example of a preferred embodiment of the invention, there is provided a compound of formula (I) as defined herein; a tautomer thereof, or a pharmaceutically acceptable salt of said compound or tautomer, wherein:
$R^x$ is selected from hydrogen and $C_1$-$C_3$ alkyl;
$R^y$ is selected from hydrogen and $C_1$-$C_3$ alkyl;
$R^a$ is selected from hydrogen, fluoro, cyano, $C_1$-$C_3$ alkyl and $C_1$-$C_3$ alkoxy;
$R^b$, $R^c$, $R^d$ and $R^e$ are each independently selected from hydrogen and $C_1$-$C_3$ alkyl; $R^f$ and $R^g$ are each independently selected from, hydrogen, fluoro, cyano, $C_1$-$C_3$ alkyl, and $C_1$-$C_3$ alkoxy;
Y is selected from $N(R^1)$, $N(R^1)$azetidinyl, and

wherein

is a 4 to 10-membered monocyclic or bicyclic heterocyclyl ring, which may be optionally substituted with one or more substituents independently selected from halo, oxo, cyano, methyl, ethyl, methoxy and ethoxy; L is selected from a covalent bond, an oxygen atom, and $C_1$-$C_3$ alkylene, with the proviso that L cannot represent an oxygen atom when Y represents $N(R^1)$;
$R^1$ is selected from hydrogen and $C_1$-$C_3$ alkyl;
$R^2$ is a 5 or 6 membered monocylic, or a 9 or 10-membered bicyclic, aryl or heteroaryl ring comprising 1 to 5 heteroatoms independently selected from nitrogen, oxygen, and sulfur; said rings being optionally substituted with 1 or 2 of $Q^1(R^3)_n$;
n is 0 or 1;
when n is 0, $Q^1$ represents $Q^{1a}$;
when n is 1, $Q^1$ represents $Q^{1b}$;
$Q^{1a}$ is selected from halo, cyano, hydroxy, $C_1$-$C_6$ alkyl, $C_1$-$C_6$ alkoxy, halo($C_1$-$C_6$ alkyl), and halo($C_1$-$C_6$ alkoxy), $C_1$-$C_3$ alkoxy-$C_1$-$C_3$ alkyl, and $C_1$-$C_3$ alkoxy-$C_1$-$C_3$ alkoxy;
$Q^{1b}$ is selected from a covalent bond, an oxygen atom, a sulphur atom, $OR^7$, SO, $SO_2$, CO, C(O)O, $C_0$-$C_3$-alkylene-C(O)$NR^4$—$C_0$-$C_3$ alkylene, $C_0$-$C_3$-alkylene-$NR^4$—$C_0$-$C_3$ alkylene, $C_0$-$C_3$-alkylene-$NR^4$C(O)—$C_0$-$C_3$ alkylene, $NR^4CONR^5$, $SO_2NR^4$, $NR^4SO_2$, $NR^4SO_2NR^5$, $NR^4$C(O)O, $NR^4$C(O)$OR^7$, $C_1$-$C_6$ alkylene and $C_2$-$C_6$ alkenylene; $R^3$ is a 3 to 10-membered, monocyclic or bicyclic, heterocyclyl, heteroaryl, cycloalkyl, or aryl ring, which may be unsubstituted or substituted with one or more substituents selected from halo, cyano, oxo, nitro, hydroxyl, $SR^8$, $C_1$-$C_6$ alkyl, $C_1$-$C_6$ alkoxy, halo($C_1$-$C_6$ alkyl), halo($C_1$-$C_6$ alkoxy), $C_2$-$C_6$ alkenyl, and $C_2$-$C_6$ alkynyl; $R^4$, $R^5$ and $R^6$ are each independently selected from hydrogen and $C_1$-$C_6$ alkyl; and $R^7$ is $C_1$-$C_6$ alkylene.

According to another example of a preferred embodiment of the invention, there is provided a compound of formula (I) as defined herein; a tautomer thereof, or a pharmaceutically acceptable salt of said compound or tautomer, wherein:
$R^x$ is selected from hydrogen, methyl, ethyl, and propyl, and is preferably hydrogen;
$R^y$ is selected from hydrogen, methyl, ethyl, and propyl and is preferably hydrogen;
$R^a$ is selected from hydrogen, fluoro, cyano, methyl, ethyl, methoxy, and ethoxy, and is preferably selected from hydrogen and methyl, and is most preferably hydrogen;

$R^b$, $R^c$, $R^d$ and $R^e$ are each independently selected from hydrogen, methyl and ethyl, and are preferably each independently selected from hydrogen and methyl; and $R^c$ and $R^e$ are each hydrogen, and most preferably are each hydrogen;

$R^f$ and $R^g$ are each independently selected from hydrogen, fluoro, and methyl, and most preferably are each hydrogen;

Y is selected from $N(R^1)$, $N(R^1)$azetidinyl, and azetidinyl, which may be optionally substituted with 1 or 2 substituents independently selected from halo and methyl; and is preferably selected from azetidinyl, N(H)azetidinyl, N(H), and $N(CH_3)$;

L is selected from a covalent bond, an oxygen atom, methylene, and ethylene, with the proviso that L cannot represent an oxygen atom when Y represents $N(R^1)$;

$R^1$ is selected from hydrogen, methyl, and ethyl;

$R^2$ is a 5 or 6 membered monocylic, or a 9 or 10 membered bicyclic, aryl or heteroaryl ring comprising 1 to 5 heteroatoms independently selected from nitrogen, oxygen, and sulfur; said rings being optionally substituted with 1 or 2 of $Q^1(R^3)_n$;

n is 0 or 1;

when n is 0, $Q^1$ represents $Q^{1a}$;

when n is 1, $Q^1$ represents $Q^{1b}$;

$Q^{1a}$ is selected from halo, cyano, hydroxyl, $C_1$-$C_3$ alkyl, $C_1$-$C_3$ alkoxy, halo($C_1$-$C_3$ alkyl), $CON(C_1$-$C_3$ alkyl)$_2$, and $C_1$-$C_3$ alkoxy-$C_1$-$C_3$ alkoxy;

$Q^{1b}$ is selected from a covalent bond and an oxygen atom;

$R^3$ is a 4 to 6-membered monocyclic, or a 9 to 10-membered bicyclic, heterocyclyl, heteroaryl, cycloalkyl, or aryl ring, which may be unsubstituted or substituted with one or more substituents selected from halo, cyano, oxo, nitro, hydroxyl, $SR^8$, $C_1$-$C_6$ alkyl, $C_1$-$C_6$ alkoxy, halo($C_1$-$C_6$ alkyl), halo($C_1$-$C_6$ alkoxy), $C_2$-$C_6$ alkenyl, and $C_2$-$C_6$ alkynyl;

$R^4$, $R^5$ and $R^6$ are each independently selected from hydrogen and methyl; and $R^7$ is methylene.

One preferred group of compounds of formula (I) for use in the present invention are selected from:

(R)—N-(3-(4-chlorophenyl)isoxazol-5-yl)-2-(1-cyanopyrrolidin-3-yl)acetamide;
(S)—N-(3-(4-chlorophenyl)isoxazol-5-yl)-2-(1-cyanopyrrolidin-3-yl)acetamide;
(S)—N-(3-(3-chlorophenyl)isoxazol-5-yl)-2-(1-cyanopyrrolidin-3-yl)acetamide;
(R)-2-(1-cyanopyrrolidin-3-yl)-N-(3-(3-methoxyphenyl)isoxazol-5-yl)acetamide;
(R)—N-(3-(3-chlorophenyl)isoxazol-5-yl)-2-(1-cyanopyrrolidin-3-yl)acetamide;
(S)-2-(1-cyanopyrrolidin-3-yl)-N-(3-(3-methoxyphenyl)isoxazol-5-yl)acetamide;
(R)—N-(5-(3-chlorophenyl)-1,3,4-oxadiazol-2-yl)-2-(1-cyanopyrrolidin-3-yl)acetamide;
(S)—N-(3-(3-chlorophenyl)isoxazol-5-yl)-2-((R)-1-cyanopyrrolidin-3-yl)propenamide;
(S)—N-(3-(3-cyanophenyl)isoxazol-5-yl)-2-(1-cyanopyrrolidin-3-yl)acetamide;
(R)-3-(2-(3-(4-cyanophenyl)azetidin-1-yl)-2-oxoethyl)pyrrolidine-1-carbonitrile;
(R)—N-(3-(3-chlorophenyl)isoxazol-5-yl)-2-((R)-1-cyanopyrrolidin-3-yl)propenamide;
(S)-2-(1-cyanopyrrolidin-3-yl)-N-(3-(3-(trifluoromethoxy)phenyl)isoxazol-5-yl)acetamide;
(S)—N-(5-(3-cyanophenyl)isoxazol-3-yl)-2-(1-cyanopyrrolidin-3-yl)acetamide;
(R)-3-(2-(3-(3-cyanophenyl)azetidin-1-yl)-2-oxoethyl)pyrrolidine-1-carbonitrile;
(R)-6-(1-(2-(1-cyanopyrrolidin-3-yl)acetyl)azetidin-3-yl)nicotinonitrile;
(R)-3-(2-(3-(4-methoxyphenyl)azetidin-1-yl)-2-oxoethyl)pyrrolidine-1-carbonitrile;
(R)-3-(2-(3-(4-cyano-3-methylphenyl)azetidin-1-yl)-2-oxoethyl)pyrrolidine-1-carbonitrile;
(R)-4-(1-(2-(1-cyanopyrrolidin-3-yl)acetyl)azetidin-3-yl)-N,N-dimethylbenzamide;
(R)-3-((S)-1-(3-(4-cyanophenyl)azetidin-1-yl)-1-oxopropan-2-yl)pyrrolidine-1-carbonitrile;
(R)-3-((R)-1-(3-(4-cyanophenyl)azetidin-1-yl)-1-oxopropan-2-yl)pyrrolidine-1-carbonitrile;
(S)-2-(1-cyanopyrrolidin-3-yl)-N-(5-phenyl-1,3,4-thiadiazol-2-yl)acetamide;
(R)-2-(1-cyanopyrrolidin-3-yl)-N-(5-phenyl-1,3,4-thiadiazol-2-yl)acetamide;
(R)-3-(2-(3-(5-isopropoxypyridin-2-yl)azetidin-1-yl)-2-oxoethyl)pyrrolidine-1-carbonitrile;
(R)-3-(2-(3-(4-(2-methoxyethoxy)phenyl)azetidin-1-yl)-2-oxoethyl)pyrrolidine-1-carbonitrile;
(R)-3-(2-(3-(4-methoxy-3-(1H-pyrazol-5-yl)phenyl)azetidin-1-yl)-2-oxoethyl)pyrrolidine-1-carbonitrile;
(R)-3-(2-(3-(4-methoxy-3-(1-methyl-1H-pyrazol-5-yl)phenyl)azetidin-1-yl)-2-oxoethyl)pyrrolidine-1-carbonitrile;
(R)-3-(2-(3-(4-methoxy-3-(1-methyl-1H-pyrazol-4-yl)phenyl)azetidin-1-yl)-2-oxoethyl)pyrrolidine-1-carbonitrile; and
(R)-3-(2-(3-(2-fluoro-3-methoxyphenyl)azetidin-1-yl)-2-oxoethyl)pyrrolidine-1-carbonitrile;
a tautomer thereof, or a pharmaceutically acceptable salt of said compound or tautomer.

More preferred compounds of formula (I) for use in the present invention are selected from: (Examples)

3-(2-(3-(4-methoxyphenyl)azetidin-1-yl)-2-oxoethyl)pyrrolidine-1-carbonitrile (Ex. 1);
N-(3-chlorophenyl)-2-(1-cyanopyrrolidin-3-yl)acetamide;
2-(1-cyanopyrrolidin-3-yl)-N-(6-methoxybenzo[d]thiazol-2-yl)acetamide;
2-(1-cyanopyrrolidin-3-yl)-N-(6-(trifluoromethyl)pyridin-3-yl)acetamide;
N-(6-chlorobenzo[d]thiazol-2-yl)-2-(1-cyanopyrrolidin-3-yl)acetamide;
2-(1-cyanopyrrolidin-3-yl)-N-(3-phenylisoxazol-5-yl)acetamide;
2-(1-cyanopyrrolidin-3-yl)-N-(5-phenylpyridin-2-yl)acetamide;
N-(5-chlorobenzo[d]oxazol-2-yl)-2-(1-cyanopyrrolidin-3-yl)acetamide;
2-(1-cyanopyrrolidin-3-yl)-N-(3,4-dichlorophenyl)acetamide;
2-(1-cyanopyrrolidin-3-yl)-N-(5-phenylthiazol-2-yl)acetamide;
2-(1-cyanopyrrolidin-3-yl)-N-phenethylacetamide;
3-(2-oxo-2-(3-phenoxyazetidin-1-yl)ethyl)pyrrolidine-1-carbonitrile;
3-(2-(3-(3-methoxyphenyl)azetidin-1-yl)-2-oxoethyl)pyrrolidine-1-carbonitrile;
3-(2-(3-(3,4-difluorophenyl)azetidin-1-yl)-2-oxoethyl)pyrrolidine-1-carbonitrile;
3-(2-(3-(2-methylpyridin-4-yl)azetidin-1-yl)-2-oxoethyl)pyrrolidine-1-carbonitrile;
2-(1-cyanopyrrolidin-3-yl)-N-(6-(3,5-dimethylisoxazol-4-yl)imidazo[1,2-a]pyridin-2-yl)acetamide;
3-(2-(3-(4-methoxyphenyl)azetidin-1-yl)-2-oxoethylidene)pyrrolidine-1-carbonitrile;
3-(2-oxo-2-(3-phenylazetidin-1-yl)ethylidene)pyrrolidine-1-carbonitrile;

N-(3-chloro-4-methylphenyl)-2-(1-cyanopyrrolidin-3-ylidene)acetamide;
N-(4-chloro-3-(trifluoromethyl)phenyl)-2-(1-cyanopyrrolidin-3-ylidene)acetamide;
N-(benzo[d]thiazol-6-yl)-2-(1-cyanopyrrolidin-3-ylidene)acetamide;
2-(1-cyanopyrrolidin-3-ylidene)-N-(4-phenoxyphenyl)acetamide;
2-(1-cyanopyrrolidin-3-ylidene)-N-(quinolin-3-yl)acetamide;
2-(1-cyanopyrrolidin-3-ylidene)-N-methyl-N-(quinolin-6-ylmethyl)acetamide;
2-(1-cyanopyrrolidin-3-ylidene)-N-methyl-N-((5-phenylisoxazol-3-yl)methyl)acetamide;
2-(1-cyanopyrrolidin-3-ylidene)-N-methyl-N-(3-(pyridin-4-yl)benzyl)acetamide;
2-(1-cyanopyrrolidin-3-ylidene)-N-methyl-N-((3-phenylisoxazol-5-yl)methyl)acetamide;
2-(1-cyanopyrrolidin-3-ylidene)-N-methyl-N-(4-(pyrrolidin-1-yl)benzyl)acetamide;
2-(1-cyanopyrrolidin-3-ylidene)-N-methyl-N-((2-phenylthiazol-4-yl)methyl)acetamide;
2-(1-cyanopyrrolidin-3-ylidene)-N-methyl-N-((5-phenyl-1H-pyrazol-3-yl)methyl)acetamide;
2-(1-cyanopyrrolidin-3-ylidene)-N-(2-fluoro-5-(trifluoromethyl)benzyl)acetamide;
N-(benzo[d]thiazol-2-yl)-2-(1-cyanopyrrolidin-3-ylidene)-N-methylacetamide;
2-(1-cyanopyrrolidin-3-ylidene)-N-(3,4-dichlorobenzyl)-N-methylacetamide;
(S)—N-(3-(4-chlorophenyl)isoxazol-5-yl)-2-(1-cyanopyrrolidin-3-yl)acetamide;
(R)—N-(3-(4-chlorophenyl)isoxazol-5-yl)-2-(1-cyanopyrrolidin-3-yl)acetamide;
(R)—N-(3-(3-chlorophenyl)isoxazol-5-yl)-2-(1-cyanopyrrolidin-3-yl)acetamide;
(S)-2-(1-cyanopyrrolidin-3-yl)-N-(3-(3-methoxyphenyl)isoxazol-5-yl)acetamide;
2-(1-cyanopyrrolidin-3-yl)-N-(5-phenyl-1,3,4-thiadiazol-2-yl)acetamide;
(S)—N-(3-(3-chlorophenyl)isoxazol-5-yl)-2-(1-cyanopyrrolidin-3-yl)acetamide;
(R)-2-(1-cyanopyrrolidin-3-yl)-N-(3-(3-methoxyphenyl)isoxazol-5-yl)acetamide;
2-(1-cyanopyrrolidin-3-yl)-N-(pyrazolo[1,5-a]pyridin-2-yl)acetamide;
2-(1-cyanopyrrolidin-3-yl)-N-(4-(trifluoromethyl)pyridin-2-yl)acetamide;
N-(5-cyanopyridin-2-yl)-2-(1-cyanopyrrolidin-3-yl)acetamide;
2-(1-cyanopyrrolidin-3-yl)-N-(1-(pyridin-2-yl)azetidin-3-yl)acetamide;
(S)—N-(5-(3-chlorophenyl)-1,3,4-oxadiazol-2-yl)-2-(1-cyanopyrrolidin-3-yl)acetamide;
N-(5-(3-cyanophenyl)-1,3,4-oxadiazol-2-yl)-2-(1-cyanopyrrolidin-3-yl)acetamide;
(S)—N-(3-(3-chlorophenyl)isoxazol-5-yl)-2-((S)-1-cyanopyrrolidin-3-yl)propenamide;
(R)—N-(3-(3-cyanophenyl)isoxazol-5-yl)-2-(1-cyanopyrrolidin-3-yl)acetamide;
(S)-3-(2-(3-(4-cyanophenyl)azetidin-1-yl)-2-oxoethyl)pyrrolidine-1-carbonitrile;
(R)—N-(3-(3-chlorophenyl)isoxazol-5-yl)-2-((S)-1-cyanopyrrolidin-3-yl)propenamide;
(R)-2-(1-cyanopyrrolidin-3-yl)-N-(3-(3-(trifluoromethoxy)phenyl)isoxazol-5-yl)acetamide;
(R)—N-(5-(3-cyanophenyl)isoxazol-3-yl)-2-(1-cyanopyrrolidin-3-yl)acetamide;
(S)-3-(2-(3-(3-cyanophenyl)azetidin-1-yl)-2-oxoethyl)pyrrolidine-1-carbonitrile;
(S)-6-(1-(2-(1-cyanopyrrolidin-3-yl)acetyl)azetidin-3-yl)nicotinonitrile;
(S)-3-(2-(3-(4-methoxyphenyl)azetidin-1-yl)-2-oxoethyl)pyrrolidine-1-carbonitrile;
3-(2-(3-(4-hydroxyphenyl)azetidin-1-yl)-2-oxoethyl)pyrrolidine-1-carbonitrile;
(S)-3-(2-(3-(4-cyano-3-methylphenyl)azetidin-1-yl)-2-oxoethyl)pyrrolidine-1-carbonitrile;
(S)-4-(1-(2-(1-cyanopyrrolidin-3-yl)acetyl)azetidin-3-yl)-N,N-dimethylbenzamide;
(S)-3-((S)-1-(3-(4-cyanophenyl)azetidin-1-yl)-1-oxopropan-2-yl)pyrrolidine-1-carbonitrile;
(S)-3-((R)-1-(3-(4-cyanophenyl)azetidin-1-yl)-1-oxopropan-2-yl)pyrrolidine-1-carbonitrile;
(R)-2-(1-cyanopyrrolidin-3-yl)-N-(5-phenyl-1,3,4-thiadiazol-2-yl)acetamide;
(S)-2-(1-cyanopyrrolidin-3-yl)-N-(5-phenyl-1,3,4-thiadiazol-2-yl)acetamide;
(S)-3-(2-(3-(5-isopropoxypyridin-2-yl)azetidin-1-yl)-2-oxoethyl)pyrrolidine-1-carbonitrile;
(S)-3-(2-(3-(4-(2-methoxyethoxy)phenyl)azetidin-1-yl)-2-oxoethyl)pyrrolidine-1-carbonitrile;
(S)-3-(2-(3-(4-methoxy-3-(1H-pyrazol-5-yl)phenyl)azetidin-1-yl)-2-oxoethyl)pyrrolidine-1-carbonitrile;
(S)-3-(2-(3-(4-methoxy-3-(1-methyl-1H-pyrazol-5-yl)phenyl)azetidin-1-yl)-2-oxoethyl)pyrrolidine-1-carbonitrile;
(S)-3-(2-(3-(4-methoxy-3-(1-methyl-1H-pyrazol-4-yl)phenyl)azetidin-1-yl)-2-oxoethyl)pyrrolidine-1-carbonitrile; and
(S)-3-(2-(3-(2-fluoro-3-methoxyphenyl)azetidin-1-yl)-2-oxoethyl)pyrrolidine-1-carbonitrile;
a tautomer thereof, or a pharmaceutically acceptable salt of said compound or tautomer.

It should be noted that each of the chemical compounds listed above represents a particular and independent aspect of the invention.

Pharmaceutical acceptable salts of the compounds of formula (I) include the acid addition and base salts (including di-salts) thereof.

Suitable acid addition salts are formed from acids which form non-toxic salts.

Examples include the acetate, aspartate, benzoate, besylate, bicarbonate/carbonate, bisulfate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D- and L-lactate, malate, maleate, malonate, mesylate, methylsulfate, 2-napsylate, nicotinate, nitrate, orotate, palmate, phosphate, saccharate, stearate, succinate sulfate, D- and L-tartrate, and tosylate salts.

Suitable base salts are formed from bases which form non-toxic salts. Examples include the aluminium, ammonium, arginine, benzathine, calcium, choline, diethylamine, triethylamine, diolamine, glycine, lysine, magnesium, meglumine, olamine, potassium, sodium, tromethamine and zinc salts.

Suitable salts also include salts of amino acids, such as glycine, alanine, valine, leucine, isoleucine, cysteine, methionine and proline. Further pharmaceutically acceptable salts include quaternary ammonium salts of the compounds of the invention.

For a review on suitable salts, see Stahl and Wermuth, Handbook of Pharmaceutical Salts: Properties, Selection, and Use, Wiley-VCH, Weinheim, Germany (2002).

A pharmaceutical acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. Salts may also be prepared by exchanging a counter-ion of a compound in the form of a salt with another counter-ion, for example using a suitable ion exchange resin.

Pharmaceutical acceptable solvates in accordance with the invention include hydrates and solvates wherein the solvent of crystallization may be isotopically substituted, e. g. $D_2O$, acetone-$d_6$, DMSO-$d_6$.

Also within the scope of the invention are clathrates, drug-host inclusion complexes wherein, in contrast to the aforementioned solvates, the drug and host are present in non-stoichiometric amounts. For a review of such complexes, see J. Pharm Sci, 64 (8), 1269-1288 by Haleblian (August 1975).

Hereinafter all references to compounds of formula (I) include references to salts thereof and to solvates and clathrates of compounds of formula (I) and salts thereof.

The invention includes all polymorphs of the compounds of formula (I) as hereinbefore defined.

Also within the scope of the invention are so-called "prodrugs" of the compounds of formula (I). Thus, certain derivatives of compounds of formula (I) which have little or no pharmacological activity themselves can, when metabolised upon administration into or onto the body, give rise to compounds of formula (I) having the desired activity. Such derivatives are referred to as "prodrugs".

Prodrugs in accordance with the invention can, for example, be produced by replacing appropriate functionalities present in the compounds of formula (I) with certain moieties known to those skilled in the art as "pro-moieties" as described, for example, in "Design of Prodrugs" by H Bundgaard (Elsevier, 1985). Finally, certain compounds of formula (I) may themselves act as prodrugs of other compounds of formula (I).

Certain derivatives of compounds of formula (I) which contain a nitrogen atom may also form the corresponding N-oxide, and such compounds are also within the scope of the present invention.

Compounds of formula (I) containing one or more asymmetric carbon atoms can exist as two or more optical isomers. Where a compound of formula (I) contains an alkenyl or alkenylene group, geometric cis/trans (or Z/E) isomers are possible, and where the compound contains, for example, a keto or oxime group, tautomeric isomerism ('tautomerism') may occur. It follows that a single compound may exhibit more than one type of isomerism.

Included within the scope of the present invention are all optical isomers, geometric isomers and tautomeric forms of the compounds of formula, including compounds exhibiting more than one type of isomerism, and mixtures of one or more thereof.

Cis/trans isomers may be separated by conventional techniques well known to those skilled in the art, for example, fractional crystallisation and chromatography.

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine.

Concentration of the eluate affords the enriched mixture. The present invention includes all crystal forms of the compounds of formula (I) including racemates and racemic mixtures (conglomerates) thereof. Stereoisomeric conglomerates may be separated by conventional techniques known to those skilled in the art—see, for example, "Stereochemistry of Organic Compounds" by E. L. Eliel and S. H. Wilen (Wiley, New York, 1994).

In particular, the compounds of formula (I) contain a chiral centre at the carbon atom of the pyrrolidine ring that is substituted by $R^a$, and said stereocentre can thus exist in either the (R) or (S) configuration. The designation of the absolute configuration (R) and (S) for stereoisomers in accordance with IUPAC nomenclature is dependent on the nature of the substituents and application of the sequence-rule procedure.

The compounds of formula (I) may thus exist in either of the following enantiomeric configurations:

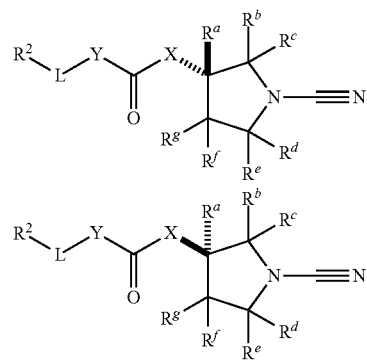

In a preferred aspect, the compounds of formula (I) possess the absolute stereochemical configuration:

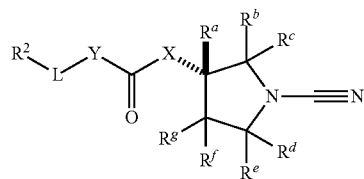

In another preferred aspect the compounds of formula (I) possess the absolute stereochemical configuration:

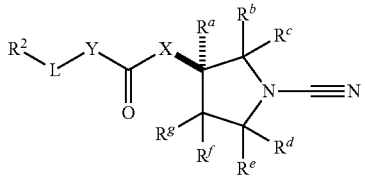

Included within the scope of the present invention are each of these (R) and (S) stereoisomers of the compounds of formula (I) in individual form, or mixtures thereof. When the compound of formula (I) is isolated as a single stereoisomer, the compound may exist with an enantiomeric excess of at least 80%, preferably at least 90%, more preferably at least 95%, for example 96%, 96%, 98%, 99%, or 100%.

The present invention also includes all pharmaceutically acceptable isotopic variations of a compound of formula (I). An isotopic variation is defined as one in which at least one atom is replaced by an atom having the same atomic number, but an atomic mass different from the atomic mass usually found in nature.

Examples of isotopes suitable for inclusion in the compounds of the invention include isotopes of hydrogen, such as $^2$H and $^3$H, carbon, such as $^{13}$C and $^{14}$C, nitrogen, such as $^{15}$N, oxygen, such as $^{17}$O and $^{18}$O, phosphorus, such as $^{32}$P, sulphur, such as $^{35}$S, fluorine, such as $^{18}$F, and chlorine, such as $^{36}$Cl.

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3$H and $^{14}$C are particularly useful for this purpose in view of their ease of incorporation and ready means of detection. Substitution with heavier isotopes i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

According to a further aspect, the present invention provides a pharmaceutical composition comprising a compound of formula (I) as defined herein, or a pharmaceutically acceptable salt of said compound or tautomer, together with a pharmaceutically acceptable diluent or carrier.

Pharmaceutical compositions of the invention comprise any of the compounds of the invention combined with any pharmaceutically acceptable carrier, adjuvant or vehicle. Examples of pharmaceutically acceptable carriers are known to those skilled in the art and include, but are not limited to, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of formula (I) are inhibitors of the deubiquitylating enzyme USP30.

According to a further aspect, the present invention provides a compound of formula (I) as defined herein, a tautomer thereof, or a pharmaceutically acceptable salt of said compound or tautomer for use as a medicament.

According to a further aspect, the present invention provides a method of treatment of a disorder or condition where inhibition of USP30 is known, or can be shown, to produce a beneficial effect, in a mammal, comprising administering to said mammal a therapeutically effective amount of a compound of formula (I) as defined herein, a tautomer thereof, or a pharmaceutically acceptable salt of said compound or tautomer.

According to a further aspect, the present invention provides the use of a compound of formula (I) as defined herein, a tautomer thereof, or a pharmaceutically acceptable salt of said compound or tautomer, in the preparation of a medicament for the treatment of a disorder or condition where inhibition of USP30 is known, or can be shown, to produce a beneficial effect.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

The disorder or condition benefiting from USP30 activity is selected from a condition involving mitochondrial dysfunction, and cancer.

In one preferred embodiment of all aspects of the invention, the disorder or condition benefiting from USP30 activity is a condition involving mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS); mitochondrial myopathy; encephalopathy; lactic acidosis; stroke-like episodes (MELAS) syndrome; Leber's hereditary optic neuropathy (LHON); cancer (including, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma); neuropathy, ataxia, retinitis pigmentosa, maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GMI-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastrointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; very long-chain acyl-CoA dehydrogenase (VL-CAD) deficiency; and age-dependent decline in cognitive function and muscle strength.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia.

In particular, the compounds of the invention may be useful in the treatment of Parkinson's disease, including, but not limited to, PD related to mutations in α-synuclein, parkin and PINK1, autosomal recessive juvenile Parkinson's disease (AR-JP) where parkin is mutated.

The compounds of the invention or pharmaceutical compositions thereof as described herein may be combined with one or more additional agents when used for the treatment of conditions involving mitochondrial dysfunction. The compounds may be combined with one or more additional agents selected from levodopa, a dopamine agonist, a mono-amino oxygenase (MAO) B inhibitor, a catechol O-methyl-transferase (COMT) inhibitor, an anticholinergic, riluzole, amantadine, a cholinesterase inhibitor, memantine, tetrabenazine, an antipsychotic, diazepam, clonazepam, an antidepressant, and an anti-convulsant.

In another preferred embodiment of all aspects of the invention, the disorder or condition benefiting from USP30 activity is cancer. The cancer may be linked to mitochondrial dysfunction. Preferred cancers include, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma.

In particular, the compounds of the invention may be useful in the treatment of cancer where apoptotic pathways are dysregulated and more particularly where proteins of the BCL-2 family are mutated, or over or under expressed.

References to 'treatment' includes curative, palliative and prophylactic, and includes means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and other mammals.

The compounds of the invention or pharmaceutical compositions thereof, as described herein, may be used alone or combined with one or more additional pharmaceutical agents. The compounds may be combined with an additional anti-tumour therapeutic agent, for example, chemotherapeutic drugs or inhibitors of other regulatory proteins. In one embodiment, the additional anti-tumour therapeutic agent is a BH-3 mimetic. In a further embodiment BH-3 mimetics may be selected from but not limited to one or more of ABT-737, ABT-199, ABT-263, and Obatoclax. In a further embodiment, the additional anti-tumour agent is a chemotherapeutic agent. Chemotherapeutic agents may be selected from but not limited to, olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

The pharmaceutical compositions of the invention may be administered in any suitably effective manner, such as oral, parenteral, topical, inhaled, intranasal, rectal, intravaginal, ocular, and andial. Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolat and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25 (2), 1-14 (2001). Other modified release formulations are described in U.S. Pat. No. 6,106,864.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Pharmaceutical compositions of the present invention also include compositions and methods known in the art for bypassing the blood brain barrier or can be injected directly into the brain. Suitable areas for injection include the cerebral cortex, cerebellum, midbrain, brainstem, hypothalamus, spinal cord and ventricular tissue, and areas of the PNS including the carotid body and the adrenal medulla.

Dosage

The magnitude of an effective dose of a compound will, of course, vary with the nature of the severity of the condition to be treated and the route of administration. The selection of appropriate dosages is within the remit of the physician. The daily dose range is about 10 μg to about 100 mg per kg body weight of a human and non-human animal and in general may be around 10 μg to 30 mg per kg body weight per dose. The above dose may be given from one to three times per day.

For example, oral administration may require a total daily dose of from 5 mg to 1000 mg, such as from 5 to 500 mg, while an intravenous dose may only require from 0.01 to 30 mg/kg body weight, such as from 0.1 to 10 mg/kg, more preferably from 0.1 to 1 mg/kg body weight. The total daily dose may be administered in single or divided doses.

The skilled person will also appreciate that, in the treatment of certain conditions, compounds of the invention may be taken as a single dose on an "as required" basis (i.e. as needed or desired).

Synthetic Methodologies

Compounds of formula (I) may be prepared using methods as described below in the general reaction schemes and the representative examples. Where appropriate, the individual transformations within a scheme may be completed in a different order.

According to a further aspect, the present invention provides a process for the preparation of a compound of formula (I), as defined herein, comprising the steps of reacting an amine of formula (II) with cyanogen bromide to form N—CN compounds of formula (I):

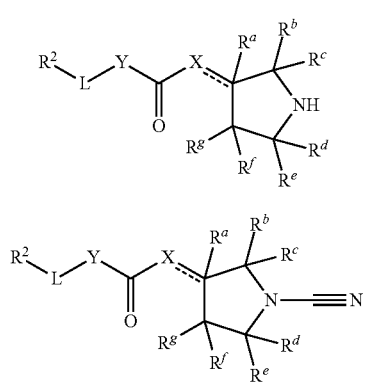

wherein $R^a$, $R^b$, $R^c$, $R^d$, $R^e$, $R^f$, $R^g$, X, Y, L and $R^2$ are as defined herein.

In a further aspect, the present invention provides a compound, which is selected from formulae (II) and (III):

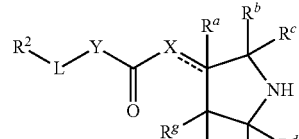

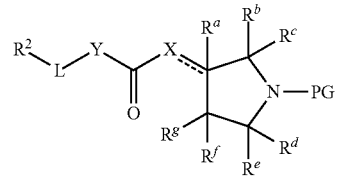

wherein PG is a protecting group, preferably BOC or CBZ, and $R^a$, $R^b$, $R^c$, $R^d$, $R^e$, $R^f$, $R^g$, X, Y, L and $R^2$ are as defined in any one of claims 1 to 12, a tautomer thereof, or a salt of said compound or tautomer.

In further preferred aspects, the present invention provides a compound, which is selected from formulae (II) and (III), as described herein, in the absolute stereochemical configuration corresponding to the compounds of formula (I), and preferred embodiments thereof.

Additional representative compounds and stereoisomers, racemic mixtures, diastereomers and enantiomers thereof may be prepared using the intermediates prepared in accordance to the general schemes and other materials, compounds and reagents known to those skilled in the art. Enantiomers may be separated using standard techniques, such as Chiral HPLC, for example, using column CHIRALART SA 250×4.6 mm 5 μm.

The invention is illustrated by the following non-limiting examples in which the following abbreviations and definitions are used.

All the compounds were characterised by liquid chromatography-mass spectroscopy (LCMS) or $^1$H NMR or both.

Synthetic Schemes

Abbreviations:

BOC Tert-butyloxycarbonyl
d Doublet (NMR signal)
DCM Dichloromethane
DIPEA Diisopropylethylamine
DMA Dimethylacetamide
DMF N,N-Dimethylformamide
DMSO Dimethylsulphoxide
dppf 1,1'-Bis(diphenylphosphino)ferrocene
EDC 1-Ethyl-3-(3-dimethylaminopropyl)carbodiimide
ES Electrospray
EtOAc Ethyl acetate
h Hour(s)
HATU 1-[Bis(dimethylamino)methylene]-1H-1,2,3-triazolo[4,5-b]pyridinium 3-oxid hexafluorophosphate
HPLC High performance liquid chromatography
HOBt 1-Hydroxybenzotriazole
IPA Isopropyl alcohol
m Multiplet (NMR signal)
MeCN Acetonitrile
min Minute(s)
rt Room temperature
RT Retention time
s Singlet (NMR signal)
SFC Supercritical fluid chromatography T3P 2,4,6-Tripropyl-1,3,5,2,4,6-trioxatriphosphorinane-2,4,6-trioxide
TEA Triethylamine
TFA Trifluoroacetic acid
THF Tetrahydrofuran
w/v Weight per volume Analytical Methods:

| Method A | | |
|---|---|---|
| Column | X-bridge C18, 50 × 4.6 mm, 3.5 μm or equivalent | |
| Mobile Phase | (A) 0.1% Ammonia in water | |
| | (B) 0.1% Ammonia in MeCN | |
| Flow Rate | 1.0 ml/min | |
| | Time | % B |
| Gradient | 0.01 | 5 |
| | 5.00 | 90 |
| | 5.80 | 95 |
| | 7.20 | 95 |

| Method B | | |
|---|---|---|
| Column | BEH C18, 50 × 2.1 mm, 1.7 μm or equivalent | |
| Mobile Phase | (A) 5 mM Ammonium acetate + 0.1% formic acid in water | |
| | (B) 0.1% Formic acid in MeCN | |
| Flow Rate | 0.45 ml/min | |
| | Time | % B |
| Gradient | 0.01 | 2 |
| | 0.50 | 2 |
| | 5.00 | 90 |
| | 6.00 | 95 |
| | 7.00 | 95 |

| Method C | | |
|---|---|---|
| Column | BEH C18, 50 × 2.1 mm, 1.7 μm or equivalent | |
| Mobile Phase | (A) 5 mM Ammonium acetate + 0.1% formic acid in water | |
| | (B) 0.1% Formic acid in MeCN | |
| Flow Rate | 0.55 ml/min | |
| | Time | % B |
| Gradient | 0.01 | 5 |
| | 0.40 | 5 |
| | 0.80 | 35 |
| | 1.20 | 55 |
| | 2.50 | 100 |
| | 3.30 | 100 |

| Method D | | |
|---|---|---|
| Column | Agilent TC-C18, 50 × 2.1 mm, 5 μm | |
| Mobile Phase | (A) 0.04% TFA in water | |
| | (B) 0.02% TFA in MeCN | |
| Flow Rate | 0.8 ml/min | |
| | Time | % B |
| Gradient | 0 | 0 |
| | 0.4 | 1 |
| | 3.4 | 100 |
| | 4 | 100 |
| Temperature | 50° C. | |

| Method E | | |
|---|---|---|
| Column | XBridge ShieldRP18, 50 × 2.1 mm, 5 μm | |
| Mobile Phase | (A) 0.05% Ammonia in water | |
| | (B) MeCN | |
| Flow Rate | 0.8 ml/min | |
| | Time | % B |
| Gradient | 0 | 0 |
| | 0.4 | 5 |
| | 3.4 | 100 |
| | 4 | 100 |
| Temperature | 40° C. | |

| Method F | | |
|---|---|---|
| Column | Agilent TC-C18, 50 × 2.1 mm, 5 μm | |
| Mobile Phase | (A) 0.04% TFA in water | |
| | (B) 0.02% TFA in MeCN | |
| Flow Rate | 0.8 ml/min | |
| | Time | % B |
| Gradient | 0 | 0 |
| | 0.4 | 0 |
| | 3.4 | 100 |
| | 4 | 100 |
| Temperature | 40° C. | |

| Method G | | |
|---|---|---|
| Column | Agilent TC-C18, 50 × 2.1 mm, 5 μm | |
| Mobile Phase | (A) 0.04% TFA in water | |
| | (B) 0.02% TFA in MeCN | |
| Flow Rate | 0.8 ml/min | |
| | Time | % B |
| Gradient | 0 | 10 |
| | 3.4 | 100 |
| | 4 | 100 |

| Method H | | |
|---|---|---|
| Column | YMC Triart C18, 150 × 4.6 mm, 5 μm | |
| Mobile Phase | (A) 10 mM Ammonium acetate in water | |
| | (B) MeCN | |
| Flow Rate | 1.0 ml/min | |
| | Time | % B |
| Gradient | 0.01 | 10 |
| | 5.00 | 90 |
| | 7.00 | 100 |
| | 11.00 | 100 |

| Chiral SFC Method Y using a Waters SFC Investigator and PDA detector | |
|---|---|
| Column | Chiralcel OJ-H, 250 × 4.6 mm, 5 μm |
| Mobile Phase | (A) Liquid CO₂ |
| | (B) IPA |
| Flow Rate | 4.0 ml/min |

| | Time | % B |
|---|---|---|
| Gradient | 0.01 | 5 |
| | 5.00 | 50 |
| | 10.00 | 50 |

| Chiral SFC Method Z using a Waters SFC Investigator and PDA detector | |
|---|---|
| Column | Chiral Pak AD-H, 250 × 4.6 mm, 5 μm |
| Mobile Phase | (A) Liquid CO₂ |
| | (B) IPA |
| Flow Rate | 4.0 ml/min |

| | Time | % B |
|---|---|---|
| Gradient | 0.01 | 5 |
| | 5.00 | 50 |
| | 8.00 | 50 |

General Method A

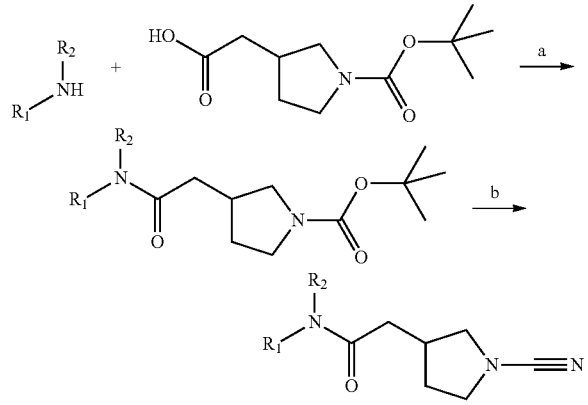

General Method B

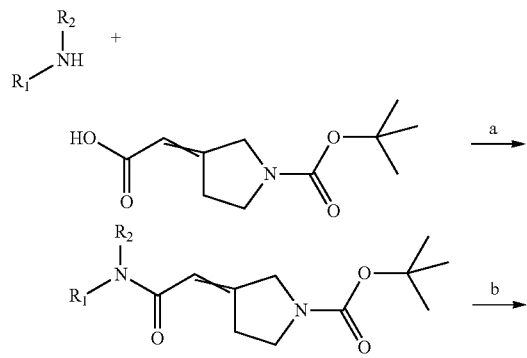

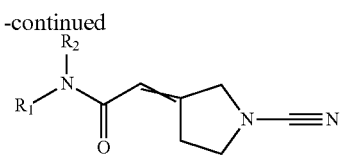

Intermediate A 3-(4-Methoxyphenyl)azetidine. TFA Salt

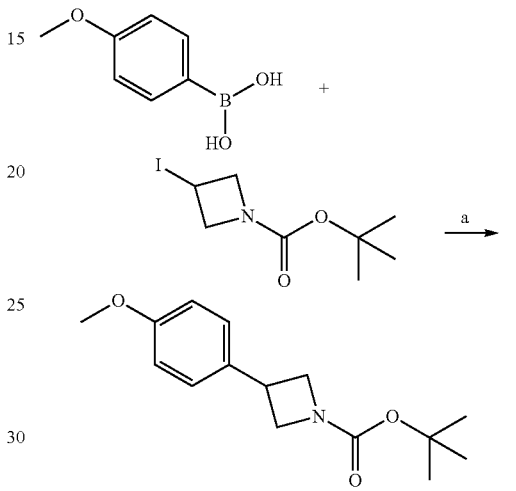

Step a

A mixture of (4-methoxyphenyl)boronic acid (CAS Number 5720-07-0; 5.37 g, 35.31 mmol), nickel iodide (0.33 g, 1.06 mmol) and trans-2-aminocyclohexanol hydrochloride (CAS Number 5456-63-3; 0.16 g, 1.06 mmol) in IPA (50 ml) was stirred at rt. Sodium bis(trimethylsilyl)amide (1M in THF) (CAS Number 1070-89-9; 35 ml, 35 mmol) was added dropwise over 20 min to the reaction mixture at rt under nitrogen, during which the colour of the reaction mixture changed from black to light green. The reaction mixture was stirred at rt for a further 20 min. A solution of tert-butyl 3-iodoazetidine-1-carboxylate (CAS Number 254454-54-1; 60.00 g, 211.9 mmol) in IPA (120 ml) was added dropwise to the reaction mixture at rt under nitrogen atmosphere. The reaction mixture was heated at 80° C. for 3 h. The resulting reaction mixture was cooled to rt and concentrated under reduced pressure. The obtained residue was diluted with saturated NaHCO₃ solution (300 ml) and extracted with EtOAc (3×200 ml). The combined organic phase was washed with brine (200 ml), dried over anhydrous Na₂SO₄, filtered and concentrated under reduced pressure. The resulting crude material was purified by column chromatography (5% EtOAc in hexane) yielding tert-butyl 3-(4-methoxyphenyl)azetidine-1-carboxylate (3.5 g, 13.290 mmol). LCMS: Method C, 2.586 min, MS: ES+264.30; ¹H NMR (400 MHz, CDCl₃) δ ppm 7.23-7.28 (m, 2H), 6.88-6.92 (m, 2H), 4.30-4.34 (m, 2H), 3.93-4.00 (m, 2H), 3.82 (s, 3H), 3.70-3.73 (m, 1H), 1.45 (s, 9H).

Step b

To a stirred solution of tert-butyl 3-(4-methoxyphenyl)azetidine-1-carboxylate (1.65 g, 6.27 mmol) in DCM (16.5 ml) was added TFA (3.3 ml, 2.0 w/v) dropwise at 0° C. The reaction was warmed to rt and stirred for 2 h. The resulting reaction mixture was concentrated under reduced pressure and azeotropically distilled using DCM (3×20 ml) followed by diethyl ether (2×20 ml). The obtained material was dried under vacuum yielding 3-(4-methoxyphenyl)azetidine TFA salt (2.65 g, quantitative). LCMS: Method C, 1.486 min, MS: ES+164.22.

Intermediate B 4-(Azetidin-3-yl)-2-methylpyridine. TFA Salt

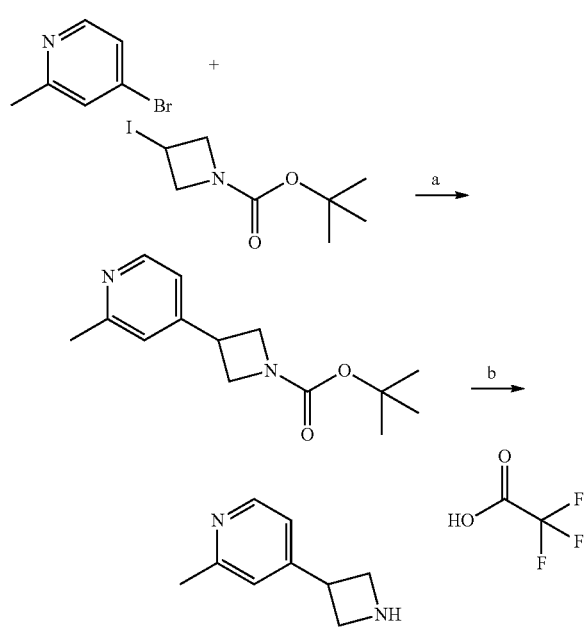

Step a

To a stirred suspension of zinc dust (0.684 g, 10.46 mmol) in DMA (6 ml) were added trimethylsilyl chloride (0.158 g, 1.453 mmol) and 1,2-dibromoethane (0.273 g, 1.453 mmol) dropwise under nitrogen atmosphere at rt in glass vial-1. The reaction mixture was stirred at rt for 20 min. N—BOC-3-iodoazetidine (CAS Number 254454-54-1; 2.468 g, 8.720 mmol) was added to the reaction mixture at rt. The resulting reaction mixture was degassed for 30 min. Simultaneously in glass vial-2 was prepared a solution of 4-bromo-2-methylpyridine (CAS Number 22282-99-1; 1.000 g, 5.81 mmol) in DMA (6 ml). CuI (0.110 g, 0.581 mmol) and Pd(dppf)Cl₂.DCM (0.332 g, 0.407 mmol) were added to the reaction mixture at rt. The resulting reaction mixture was degassed for 30 min. Then glass vial-2 reaction mixture was added dropwise into glass vial-1 reaction mixture at rt. The resulting reaction mixture was heated at 80° C. for 16 h. The reaction mixture was cooled to rt and poured into water (100 ml). The obtained mixture was extracted with EtOAc (2×80 ml). The combined organic phase was washed with brine solution (100 ml), dried over Na₂SO₄, filtered and concentrated under reduced pressure. The resulting residue was purified by flash chromatography (60% EtOAc in hexane) yielding tert-butyl 3-(2-methylpyridin-4-yl)azetidine-1-carboxylate (0.640 g, 2.58 mmol). LCMS: Method C, 1.401 min, MS: ES+249.38; ¹H NMR (400 MHz, CDCl₃) δ ppm 8.38 (d, J=5.2 Hz, 1H), 7.22 (s, 1H), 7.14 (d, J=5.2 Hz, 1H), 4.21-4.35 (m, 2H), 3.80-3.84 (m, 2H), 3.74-3.78 (m, 1H), 2.45 (s, 3H), 1.39 (s, 9H).

Step b

The title compound was synthesised from the intermediate above using a procedure similar to that described for Intermediate A. MS: ES+148.99

Intermediate C 2-(1-(Tert-butoxycarbonyl)pyrrolidin-3-ylidene)acetic acid

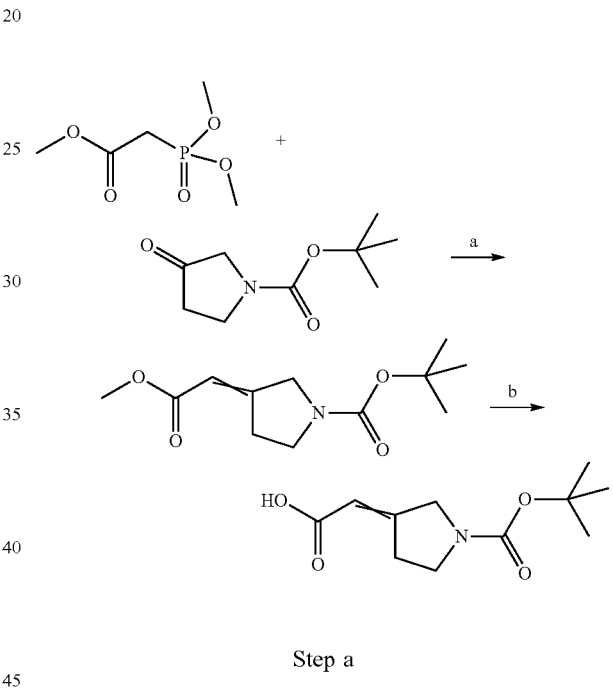

Step a

To a stirred solution of methyl 2-(dimethoxyphosphoryl)acetate (CAS Number 5927-18-4; 2.360 g, 12.96 mmol) in THF (40 ml) was added 60% NaH on mineral oil (0.311 g, 12.96 mmol) portion wise at 0° C. The reaction mixture stirred for 20 min at 0° C. A solution of tert-butyl 3-oxopyrrolidine-1-carboxylate (CAS Number 101385-93-7; 2.000 g, 10.80 mmol) in THF (10 ml) was dropwise added to the reaction mixture at 0° C. The reaction mixture was warmed to rt and stirred for 16 h. The resulting reaction mixture was combined with one other batch prepared on the same scale by an identical method. The reaction mixture quenched with ice cold water (150 ml) and extracted with EtOAc (3×100 ml). The combined organic phase was dried over Na₂SO₄, filtered and concentrated on reduced pressure yielding tert-butyl 3-(2-methoxy-2-oxoethylidene)pyrrolidine-1-carboxylate (5.679 g, quantitative). LCMS: Method C, 2.034 min, MS: ES+242.50. This material was directly used for the next step without any further purification.

Step b

To a stirred solution of tert-butyl 3-(2-methoxy-2-oxoethylidene)pyrrolidine-1-carboxylate (5.659 g, 23.43 mmol) in THF:water (1:1, 50 ml) was added LiOH (1.970 g, 46.86 mmol) portion-wise at rt. The reaction mixture was heated at 50° C. for 16 h then cooled to 0° C. and adjusted to pH ~4 using dilute HCl solution (14 ml). The resulting mixture was diluted with water (10 ml) and extracted with EtOAc (50 ml) followed by 10% IPA: CHCl₃ mixture (2×100 ml). The combined organic phase was dried over Na₂SO₄, filtered and concentrated under reduced pressure yielding 2-(1-(tert-butoxycarbonyl)pyrrolidin-3-ylidene)acetic acid (5.540 g, quantitative). LCMS: Method C, 1.652, 1.677 min, MS: ES+228.30. This material was directly used for the next step without any further purification.

Example 1 3-(2-(3-(4-Methoxyphenyl)azetidin-1-yl)-2-oxoethyl)pyrrolidine-1-carbonitrile (Prepared According to General Method A)

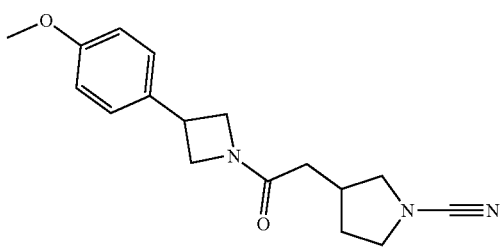 [SMILES: COc1ccc(C2CN(C(=O)CC3CCN(C#N)C3)C2)cc1]

Step a

To a solution of 2-(1-(tert-butoxycarbonyl)pyrrolidin-3-yl)acetic acid (CAS Number 175526-97-3; 0.200 g, 0.872 mmol) in DMF (5 ml) were added HATU (0.397 g, 1.046 mmol) and DIPEA (0.225 g, 1.744 mmol) at 0° C. The reaction mixture was stirred at 0° C. for 20 min. A solution of 3-(4-methoxyphenyl)azetidine TFA salt (Intermediate A, 0.241 g, 0.872 mmol) in DMF (2 ml) was added to the reaction mixture at rt. The reaction mixture was stirred at rt for 16 h. The resulting mixture was diluted with water (200 ml) and extracted with EtOAc (5×50 ml). The combined organic phase was washed with dilute citric acid solution (2×100 ml) followed by saturated NaHCO₃ solution (2×100 ml). The organic phase was dried over anhydrous Na₂SO₄, filtered and concentrated under reduced pressure. The resulting residue was purified by flash column chromatography (2.5% MeOH in DCM) yielding tert-butyl 3-(2-(3-(4-methoxyphenyl)azetidin-1-yl)-2-oxoethyl)pyrrolidine-1-carboxylate (0.190 g, 0.507 mmol). LCMS: Method C, 1.978 min, MS: ES+375.55.

Step b

To a stirred solution of tert-butyl 3-(2-(3-(4-methoxyphenyl)azetidin-1-yl)-2-oxoethyl)pyrrolidine-1-carboxylate (0.180 g, 0.481 mmol) in DCM (10 ml) was added TFA (0.4 ml, 2.0 w/v) dropwise at 0° C. The reaction mixture was stirred at rt for 30 min. The resulting mixture was concentrated under reduced pressure yielding 1-(3-(4-methoxyphenyl)azetidin-1-yl)-2-(pyrrolidin-3-yl)ethan-1-one TFA salt (0.170 g, quantitative). LCMS: Method C, 1.398 min, MS: ES+275.43.

Step c

To a solution of 1-(3-(4-methoxyphenyl)azetidin-1-yl)-2-(pyrrolidin-3-yl)ethan-1-one TFA salt (0.165 g, 0.425 mmol) in THF (15 ml) was added K₂CO₃ (0.586 g, 4.252 mmol) at 0° C. The reaction mixture was stirred at 0° C. for 10 min. Cyanogen bromide (0.054 g, 0.510 mmol)) was added to the reaction mixture at 0° C., warmed to rt and stirred for 30 min. The resulting mixture was poured into water (50 ml) and extracted with EtOAc (6×50 ml). The combined organic phase was dried over Na₂SO₄, filtered and concentrated under reduced pressure. The resulting residue was purified by flash column chromatography (2% MeOH in DCM) yielding title compound (0.073 g, 0.24 mmol). LCMS: Method B, 3.360 min, MS: ES+300.48; ¹H NMR (400 MHz, DMSO-d6) δ ppm: 7.28 (d, J=8.4 Hz, 2H), 6.90-6.93 (m, 2H), 4.44-4.49 (m, 1H), 4.19-4.24 (m, 1H), 4.04-4.07 (m, 1H), 3.76-3.81 (m, 2H), 3.74 (s, 3H), 3.49-3.53 (m, 1H), 3.33-3.44 (m, 1H), 3.22-3.32 (m, 1H), 2.98-3.03 (m, 1H), 2.44-2.49 (m, 1H), 2.16-2.29 (m, 2H), 1.97-2.04 (m, 1H), 1.52-1.59 (m, 1H).

Compounds in Table 1 were synthesised according to general method A as exemplified by Example 1.

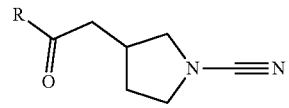

TABLE 1

| Ex | R | Name | LCMS Method | LCMS RT (min) | MS |
|---|---|---|---|---|---|
| 2 | ![Cl-phenyl-NH] | N-(3-Chlorophenyl)-2-(1-cyanopyrrolidin-3-yl)acetamide | D | 2.795 | ES+ 264.0 |
| 3 | ![methoxybenzothiazol-NH] | 2-(1-Cyanopyrrolidin-3-yl)-N-(6-methoxybenzo[d]thiazol-2-yl)acetamide | D | 2.735 | ES+ 317.0 |

TABLE 1-continued

| Ex | R | Name | LCMS Method | LCMS RT (min) | MS |
|----|---|------|-------------|---------------|-----|
| 4 | 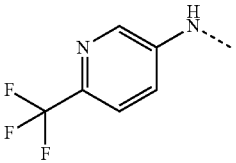 | 2-(1-Cyanopyrrolidin-3-yl)-N-(6-(trifluoromethyl)pyridin-3-yl)acetamide | E | 2.307 | ES+ 299.0 |
| 5 | 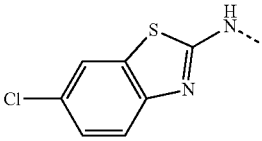 | N-(6-Chlorobenzo[d]thiazol-2-yl)-2-(1-cyanopyrrolidin-3-yl)acetamide | D | 3.001 | ES+ 320.9 |
| 6 | 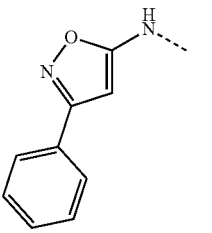 | 2-(1-Cyanopyrrolidin-3-yl)-N-(3-phenylisoxazol-5-yl)acetamide | D | 2.827 | ES+ 297.0 |
| 7 | 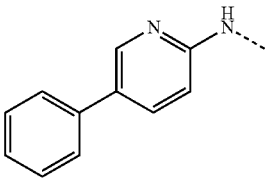 | 2-(1-Cyanopyrrolidin-3-yl)-N-(5-phenylpyrrolidin-2-yl)acetamide | D | 2.679 | ES+ 307.0 |
| 8 | 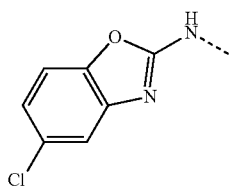 | N-(5-Chlorobenzo[d]oxazol-2-yl)-2-(1-cyanopyrrolidin-3-yl)acetamide | D | 2.651 | ES+ 304.9 |
| 9 | 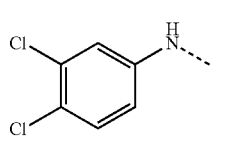 | 2-(1-Cyanopyrrolidin-3-yl)-N-(3,4-dichlorophenyl)acetamide | D | 3.016 | ES+ 297.9 & 299.9 |

Compounds in Table 2 were synthesised according to general method A as exemplified by Example 1.

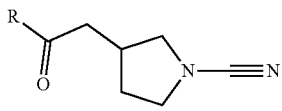

TABLE 2

| Ex | R | Name | Amine CAS Number | $^1$H NMR: (400 MHz, DMSO-d$_6$) δ ppm | LCMS Method | LCMS RT (min) | MS |
|---|---|---|---|---|---|---|---|
| 10 | (5-phenylthiazol-2-yl)amino group | 2-(1-Cyanopyrrolidin-3-yl)-N-(5-phenylthiazol-2-yl)acetamide | 39136-63-5 | 12.26 (s, 1 H), 7.88 (s, 1 H), 7.60-7.62 (m, 2 H), 7.40-7.43 (m, 2 H), 7.28-7.32 (m, 1 H), 3.53-3.57 (m, 1 H), 3.42-3.47 (m, 1 H), 3.33-3.39 (m, 2 H), 3.06-3.10 (m, 1 H), 2.59 (d, J = 2.0 Hz, 2 H), 2.01-2.06 (m, 1 H), 1.57-1.62 (m, 1 H). | A | 3.902 | ES+ 312.97 |
| 11 | phenethylamino group | 2-(1-Cyanopyrrolidin-3-yl)-N-phenethylacetamide | 64-04-0 | 7.96 (t, J = 5.2 Hz, 1 H), 7.27-7.30 (m, 2 H), 7.17-7.21 (m, 3 H), 3.37-3.44 (m, 2 H), 3.25-3.33 (m, 3 H), 2.91-2.95 (m, 1 H), 2.68-2.72 (m, 2 H), 2.38-2.45 (m, 1 H), 2.12-2.14 (m, 2 H), 1.86-1.93 (m, 1 H), 1.41-1.51 (m, 1 H) | B | 3.344 | ES+ 258.46 |
| 12 | 3-phenoxyazetidin-1-yl | 3-(2-Oxo-2-(3-phenoxyazetidin-1-yl)ethyl)pyrrolidine-1-carbonitrile | 301335-39-7 | 7.28-7.34 (m, 2 H), 7.01-7.05 (m, 1 H), 6.75-6.77 (m, 2 H), 4.97-4.99 (m, 1 H), 4.47-4.52 (m, 1 H), 4.38-4.42 (m, 1 H), 4.16-4.20 (m, 1 H), 4.07-4.10 (m, 1 H), 3.64-3.68 (m, 1 H), 3.40-3.52 (m, 2 H), 3.01-3.10 (m, 1 H), 2.67-2.72 (m, 1 H), 2.19-2.23 (m, 2 H), 2.12-2.17 (m, 1 H), 1.60-1.67 (m, 1 H) | B | 3.523 | ES+ 286.43 |
| 13 | 3-(3-methoxyphenyl)azetidin-1-yl | 3-(2-(3-(3-Methoxyphenyl)azetidin-1-yl)-2-oxoethyl)pyrrolidine-1-carbonitrile | synthesised using a procedure similar to that described for Intermediate A | 7.28 (t, J = 8.0 Hz, 1 H), 6.90-6.94 (m, 2 H), 6.83 (dd, J = 8.0, 2.4 Hz, 1 H), 4.46-4.48 (m, 1 H), 4.20-4.26 (m, 1 H), 4.10-4.14 (m, 1 H), 3.79-3.84 (m, 2 H), 3.76 (s, 3 H), 3.49-3.53 (m, 1 H), 3.28-3.45 (m, 2 H), 2.98-3.03 (m, 1 H), 2.44-2.49 (m, 1 H), 2.16-2.29 (m, 2 H), 1.99-2.04 (m, 1 H), 1.50-1.58 (m, 1 H) | A | 3.658 | ES+ 300.03 |
| 14 | 3-(3,4-difluorophenyl)azetidin-1-yl | 2-(1-Cyanopyrrolidin-3-yl)-N-(3,4-dichlorophenyl)acetamide | synthesised using a procedure similar to that described for Intermediate A | 7.49-7.54 (m, 1 H), 7.38-7.45 (m, 1 H), 7.21-7.26 (m, 1 H), 4.44-4.49 (m, 1 H), 4.20-4.24 (m, 1 H), 4.10-4.13 (m, 1 H), 3.78-3.90 (m, 2 H), 3.49-3.53 (m, 1 H), 3.39-3.44 (m, 1 H), 3.29-3.32 (m, 1 H), 2.98-3.03 (m, 1 H), 2.43-2.47 (m, 1 H), 2.15-2.29 (m, 2 H), 1.98-2.03 (m, 1 H), 1.53-1.59 (m, 1 H) | A | 3.795 | ES+ 305.95 |
| 15 | 3-(2-methylpyridin-4-yl)azetidin-1-yl | 3-(2-(3-(2-Methylpyridin-4-yl)azetidin-1-yl)-2-oxoethyl)pyrrolidine-1-carbonitrile | Intermediate B | 8.39 (dd, J = 4.8, 2.4 Hz, 1 H), 7.25 (s, 1 H), 7.16-7.18 (m, 1 H), 4.46-4.50 (m, 1 H), 4.21-4.25 (m, 1 H), 4.11-4.14 (m, 1 H), 3.82-3.85 (m, 2 H), 3.44-3.53 (m, 1 H), 3.28-3.45 (m, 2 H), 2.98-3.03 (m, 1 H), 2.46-2.49 (m, 1 H), 2.45 (s, 3 H), 2.18-2.29 (m, 2 H), 2.00-2.03 (m, 1 H), 1.52-1.59 (m, 1 H) | H | 4.129 | ES+ 285.10 |

Example 16 2-(1-Cyanopyrrolidin-3-yl)-N-(6-(3,5-dimethylisoxazol-4-yl)imidazo[1,2-a]pyridin-2-yl) acetamide

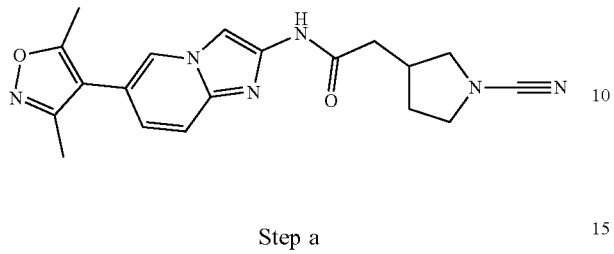

Step a

To a stirred solution of 6-bromoimidazo[1,2-a]pyridin-2-amine (CAS Number 947248-52-4; 0.200 g, 1.00 mmol) and 2-(1-(tert-butoxycarbonyl)pyrrolidin-3-yl)acetic acid (CAS Number 175526-97-3; 0.229 g, 1.00 mmol) in THF (10 ml) were added TEA (0.200 g, 2.01 mmol) at 0° C. T3P (50% in EtOAc) (0.479 g, 1.50 mmol) was added dropwise to the reaction mixture at 0° C. then stirred at rt for 1 h. The resulting mixture was diluted with water (10 ml) and extracted with EtOAc (2×10 ml). The combined organic phase was dried over anhydrous $Na_2SO_4$, filtered and concentrated under reduced pressure. The residue was purified by flash column chromatography (2% MeOH in DCM) yielding tert-butyl 3-(2-((6-bromoimidazo[1,2-a]pyridin-2-yl)amino)-2-oxoethyl)pyrrolidine-1-carboxylate (0.230 g, 0.543 mmol). LCMS: Method C, 2.048 min, MS: ES+423.28, 425.30.

Step b

A solution of methyl tert-butyl 3-(2-((6-bromoimidazo[1,2-a]pyridin-2-yl)amino)-2-oxoethyl)pyrrolidine-1-carboxylate (0.230 g, 0.543 mmol) and (3,5-dimethylisoxazol-4-yl)boronic acid (CAS Number 16114-47-9; 0.190 g, 1.35 mmol) in THF:water (1:1, 20 ml) was prepared in a microwaveable glass tube. CsF (0.164 g, 1.078 mmol) was added to the reaction mixture, which was then degassed for 15 min before adding $Pd(PPh_3)_2Cl_2$ (0.076 g, 0.108 mmol). The glass tube was sealed and the reaction mixture was subjected to microwave heating at 100° C. for 1 h. The resulting reaction mixture was cooled to rt, poured into water (10 ml) and extracted with EtOAc (2×20 ml). The combined organic layer was dried over $Na_2SO_4$, filtered and concentrated under reduced pressure. The residue was purified by flash column chromatography (7-8% MeOH in DCM) yielding tert-butyl 3-(2-((6-(3,5-dimethylisoxazol-4-yl)imidazo[1,2-a]pyridin-2-yl)amino)-2-oxoethyl)pyrrolidine-1-carboxylate (0.200 g, 0.454 mmol). LCMS: Method C, 1.920 min, MS: ES+440.53.

Steps c, d

The title compound was synthesised from the intermediate above using a procedure similar to that described for Example 1. LCMS: Method B, 3.041 min, MS: ES+365.33; $^1$H NMR (400 MHz, DMSO-d6) δ ppm 10.82 (s, 1H), 8.64 (s, 1H), 8.14 (s, 1H), 7.50 (d, J=9.2 Hz, 1H), 7.24 (dd, J=9.2, 2.0 Hz, 1H), 3.51-3.55 (m, 1H), 3.42-3.47 (m, 1H), 3.33-3.39 (m, 1H), 3.05-3.09 (m, 1H), 2.59 (d, J=2.0 Hz, 2H), 2.43 (s, 3H), 2.25 (s, 3H), 1.98-2.06 (m, 1H), 1.54-1.64 (m, 1H).

Example 17 3-(2-(3-(4-Methoxyphenyl)azetidin-1-yl)-2-oxoethylidene)pyrrolidine-1-carbonitrile (Prepared according to general method B)

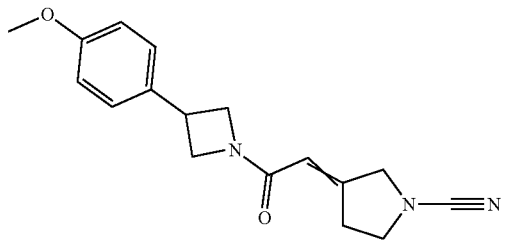 [SMILES: COc1ccc(C2CN(C(=O)C=C3CCN(C#N)C3)C2)cc1]

Step a

To a stirred solution of 2-(1-(tert-butoxycarbonyl)pyrrolidin-3-ylidene)acetic acid (Intermediate C; 1.100 g, 4.84) in THF (10 ml) was added EDC.HCl (1.390 g, 7.26 mmol) at 0° C. The reaction mixture was stirred for 10 min before addition of HOBt (0.982 g, 7.26 mmol). The reaction mixture was stirred at 0° C. for a further 30 min. A solution of 3-(4-methoxyphenyl)azetidine TFA salt (Intermediate A; 1.540 g, 5.56 mmol) in THF (5 ml) was dropwise added to the reaction mixture at 0° C. The resulting mixture was stirred at rt for 16 h. The reaction was diluted with water (50 ml) and basified using saturated $NaHCO_3$ solution. The resulting mixture was extracted with EtOAc (5×30 ml). The combined organic phase was dried over anhydrous $Na_2SO_4$, filtered and concentrated under reduced pressure. The residue was purified by flash column chromatography (16% EtOAc in hexane) yielding tert-butyl 3-(2-(3-(4-methoxyphenyl)azetidin-1-yl)-2-oxoethylidene)pyrrolidine-1-carboxylate (0.430 g, 1.155 mmol). LCMS: Method C, 8.331, 8.626 min, MS: ES+373.20.

Step b

To a stirred solution of tert-butyl 3-(2-(3-(4-methoxyphenyl)azetidin-1-yl)-2-oxoethylidene)pyrrolidine-1-carboxylate (0.430 g, 1.155 mmol) in DCM (10 ml) was added TFA (2.1 ml) dropwise at 0° C. The reaction mixture was stirred at rt for 45 min. The resulting reaction mixture was concentrated under reduced pressure and azeotropically distilled using DCM (3×20 ml) followed by diethyl ether (2×20 ml). The obtained material was dried under vacuum yielding 1-(3-(4-methoxyphenyl)azetidin-1-yl)-2-(pyrrolidin-3-ylidene)ethan-1-one TFA salt (0.440 g, quantitative). LCMS: Method C, 1.402 min, MS: ES+273.48.

Step c

To a solution of 1-(3-(4-methoxyphenyl)azetidin-1-yl)-2-(pyrrolidin-3-ylidene)ethan-1-one TFA salt (0.440 g, 1.14 mmol) in THF (15 ml) was added TEA (0.60 ml, 4.55 mmol) at −78° C. The reaction mixture was stirred at −78° C. for 10 min. Cyanogen bromide (0.181 g, 1.71 mmol) was added to the reaction mixture at −78° C. The reaction mixture was slowly warmed to rt and stirred for 1.5 h. The resulting mixture was poured into water (30 ml) and extracted with EtOAc (3×15 ml). The combined organic phase was dried over $Na_2SO_4$, filtered and concentrated under reduced pressure. The resulting residue was purified by flash column chromatography (60% EtOAc in hexane) yielding title compound (0.162 g, 0.545 mmol). LCMS: Method B, 3.532, 3.626 min, MS: ES+298.48; $^1$H NMR (400 MHz, DMSO-d6) δ ppm: 7.28 (d, J=8.4 Hz, 2H), 6.92 (d, J=8.8 Hz, 2H), 5.98-6.02 (m, 1H), 4.50-4.57 (m, 1H), 4.39 (s, 1H), 4.23-4.29 (m, 1H), 4.16-4.14 (m, 2H), 3.77-3.84 (m, 2H), 3.74 (s, 3H), 3.50-3.54 (m, 1H), 3.43-3.46 (m, 1H), 2.99-3.03 (m, 1H), 2.71-2.74 (m, 1H).

Example 18 3-(2-Oxo-2-(3-phenylazetidin-1-yl)ethylidene)pyrrolidine-1-carbonitrile

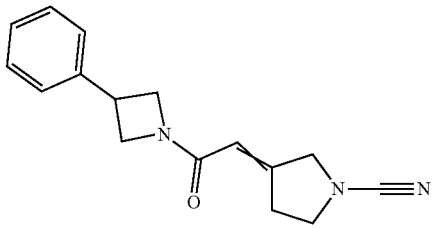 [SMILES: N#CN1CCC(=CC(=O)N2CC(c3ccccc3)C2)C1]

The title compound was synthesised using a procedure similar to that described for Example 17, using 3-phenylazetidine (CAS Number 4363-13-7) in step a. LCMS: Method B, 3.559, 3.655 min, MS: ES+268.48; $^1$H NMR (400 MHz, DMSO-d$_6$) δ ppm 7.35-7.36 (m, 4H), 7.24-7.28 (m, 1H), 5.99-6.02 (m, 1H), 4.53-4.59 (m, 1H), 4.39 (s, 1H), 4.26-4.32 (m, 1H), 4.11-4.17 (m, 2H), 3.83-3.87 (m, 2H), 3.50-3.53 (m, 1H), 3.40-3.46 (m, 1H), 2.99-3.02 (m, 1H), 2.71-2.74 (m, 1H).

Compounds in Table 3 were synthesised according to general method B as exemplified by Example 17.

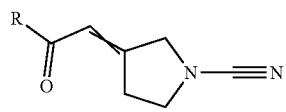

TABLE 3

| Ex | R | Name | LCMS Method | LCMS RT (min) | MS |
|---|---|---|---|---|---|
| 19 | 3-Chloro-4-methylphenyl | N-(3-Chloro-4-methylphenyl)-2-(1-cyanopyrrolidin-3-ylidene)acetamide | F | 3.197 | ES+ 276.1 |
| 20 | 4-Chloro-3-(trifluoromethyl)phenyl | N-(4-Chloro-3-(trifluoromethyl)phenyl)-2-(1-cyanopyrrolidin-3-ylidene)acetamide | F | 3.402 | ES+ 330.0 |
| 21 | Benzo[d]thiazol-6-yl | N-(Benzo[d]thiazol-6-yl)-2-(1-cyanopyrrolidin-3-ylidene)acetamide | D | 2.178 | ES+ 285.0 |
| 22 | 4-phenoxyphenyl | 2-(1-Cyanopyrrolidin-3-ylidene)-N-(4-phenoxyphenyl)acetamide | E | 2.567 | ES+ 320.1 |
| 23 | quinolin-3-yl | 2-(1-Cyanopyrrolidin-3-ylidene)-N-(quinolin-3-yl)acetamide | E | 2.262 | ES+ 279.1 |
| 24 | N-methyl-N-(quinolin-6-ylmethyl) | 2-(1-Cyanopyrrolidin-3-ylidene)-N-methyl-N-(quinolin-6-ylmethyl)acetamide | E | 2.822 | ES+ 307.2 |
| 25 | N-methyl-N-((5-phenylisoxazol-3-yl)methyl) | 2-(1-Cyanopyrrolidin-3-ylidene)-N-methyl-N-((5-phenylisoxazol-3-yl)methyl)acetamide | E | 3.261 | ES+ 323.2 |

TABLE 3-continued

| Ex | R | Name | LCMS Method | LCMS RT (min) | MS |
|---|---|---|---|---|---|
| 26 | 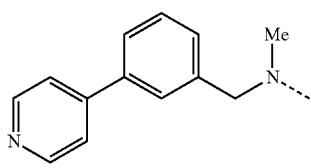 | 2-(1-Cyanopyrrolidin-3-ylidene)-N-methyl-N-(3-(pyridin-4-yl)benzyl)acetamide | E | 3.029 | ES+ 333.2 |
| 27 | 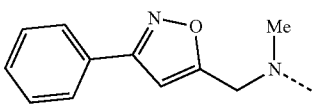 | 2-(1-Cyanopyrrolidin-3-ylidene)-N-methyl-N-((3-phenylisoxazol-5-yl)methyl)acetamide | E | 3.219 | ES+ 323.2 |
| 28 | 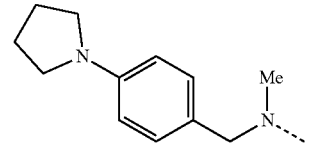 | 2-(1-Cyanopyrrolidin-3-ylidene)-N-methyl-N-(4-(pyrrolidin-1-yl)benzyl)acetamide | E | 3.448 | ES+ 325.2 |
| 29 | 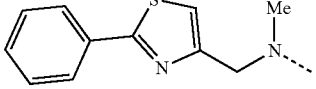 | 2-(1-Cyanopyrrolidin-3-ylidene)-N-methyl-((2-phenylthiazol-4-yl)methyl)acetamide | E | 2.545 | ES+ 339.1 |
| 30 | 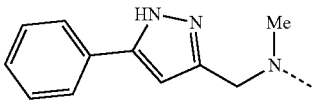 | 2-(1-Cyanopyrrolidin-3-ylidene)-N-methyl-N-((5-phenyl-1H-pyrazol-3-yl)methyl)acetamide | E | 2.231 | ES+ 322.1 |
| 31 |  | 2-(1-Cyanopyrrolidin-3-ylidene)-N-(2-fluoro-5-(trifluoromethyl)benzyl)acetamide | G | 2.785 | ES+ 328.1 |
| 32 | 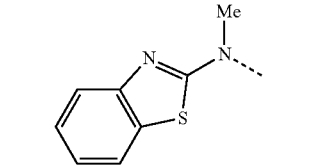 | N-(Benzo[d]thiazol-2-yl)-2-(1-cyanopyrrolidin-3-ylidene)-N-methylacetamide | F | 3.404 | ES+ 299.0 |
| 33 | 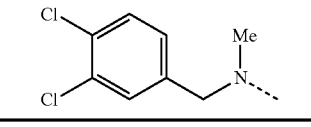 | 2-(1-Cyanopyrrolidin-3-ylidene)-N-(3,4-dichlorobenzyl)-N-methylacetamide | G | 2.982 | ES+ 324.0 |

Example 34 (S)—N-(3-(4-Chlorophenyl)isoxazol-5-yl)-2-(1-cyanopyrrolidin-3-yl)acetamide

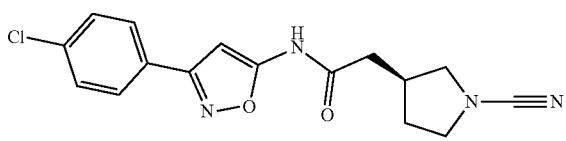 [SMILES: N#CN1CC[C@@H](CC(=O)Nc2cc(-c3ccc(Cl)cc3)no2)C1]

Step a. To a solution of 3-(4-chlorophenyl)-3-oxopropanenitrile (CAS Number 4640-66-8; 3.000 g, 16.70 mmol) and NH₂OH.HCl (1.390 g, 20.00 mmol) in water (45 ml) was added NaOH (1.330 g, 33.41 mmol) portion wise at 0° C. The reaction mixture was heated to 100° C. for 3 h. The resulting reaction mixture was cooled to rt and poured into water (250 ml) then extracted with EtOAc (4×50 ml). The combined organic layer was dried over Na₂SO₄, filtered and concentrated under reduced pressure. The resulting residue was purified by flash column chromatography (32% EtOAc in hexane) yielding 3-(4-chlorophenyl)isoxazol-5-amine (1.800 g, 9.277 mmol). LCMS: Method C, 1.777 min, MS: ES+195.19; ¹H NMR (400 MHz, DMSO) b ppm 7.75 (d, J=8.8, 2H), 7.51 (d, J=8.8, 2H), 6.83 (s, 2H), 5.42 (s, 1H).

Step b

To a solution of 3-(4-chlorophenyl)isoxazol-5-amine (0.170 g, 0.876 mmol) and (S)-2-(1-(tert-butoxycarbonyl)pyrrolidin-3-yl)acetic acid (CAS Number 204688-61-9; 0.200 g, 0.876 mmol) in pyridine (6 ml) was added POCl₃ (0.25 ml, 2.628 mmol) dropwise at 0° C. The reaction mixture was stirred for 30 min at rt. The resulting reaction mixture was poured into water (100 ml) and extracted with EtOAc (3×25 ml). The combined organic layer was dried over Na$_2$SO$_4$, filtered and concentrated under reduced pressure. The resulting residue was purified by flash column chromatography (36% EtOAc in hexane) yielding tert-butyl (S)-3-(2-((3-(4-chlorophenyl) isoxazol-5-yl)amino)-2-oxoethyl)-pyrrolidine-1-carboxylate (0.153 g, 0.377 mmol). LCMS Method C: 2.396 min, MS: ES+406.53.

Step c

To a solution of tert-butyl (S)-3-(2-((3-(4-chlorophenyl) isoxazol-5-yl)amino)-2-oxoethyl)pyrrolidine-1-carboxylate (0.150 g, 0.370 mmol) was added TFA (1.5 ml, 10 vol) at 0° C. The reaction mixture was stirred at rt for 1 h then concentrated under reduced pressure and azeotropically distilled using DCM (3×10 ml). The obtained material was dried under vacuum yielding (S)—N-(4-(4-chlorophenyl) furan-2-yl)-2-(pyrrolidin-3-yl)acetamide TFA salt (0.150 g, quantitative). LCMS: Method C, 1.552 min, MS: ES+306.43.

Step d

To a solution of (S)—N-(4-(4-chlorophenyl)furan-2-yl)-2-(pyrrolidin-3-yl)acetamide TFA salt (0.150 g, 0.357 mmol) in THF (5 ml) was added K$_2$CO$_3$ (0.148 g, 1.073 mmol) at 0° C. The reaction mixture was stirred for 5 min and then treated with cyanogen bromide (0.045 g, 0.429 mmol). The reaction mixture was slowly warmed to rt and stirred for 1 h. The resulting mixture was poured into water (50 ml) and extracted with EtOAc (3×15 ml). The combined organic phase was dried over Na$_2$SO$_4$, filtered and concentrated under reduced pressure. The resulting residue was purified by flash column chromatography (72% EtOAc in hexane) yielding title compound (0.075 g, 0.226 mmol). LCMS: Method A, 4.399 min, MS: ES+331.02; $^1$H NMR (400 MHz, DMSO-d6) δ ppm 11.81 (s, 1H), 7.89 (d, J=8.4 Hz, 2H), 7.57 (d, J=8.4 Hz, 2H), 6.77 (s, 1H), 3.53-3.57 (m, 1H), 3.42-3.47 (m, 1H), 3.35-3.39 (m, 1H), 3.05-3.09 (m, 1H), 2.56-2.60 (m, 3H), 2.02-2.06 (m, 1H), 1.57-1.62 (m, 1H).

Example 35 (R)—N-(3-(4-Chlorophenyl)isoxazol-5-yl)-2-(1-cyanopyrrolidin-3-yl)acetamide

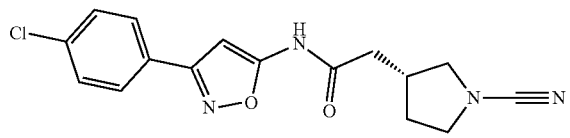 [SMILES: N#CN1CC[C@H](CC(=O)Nc2cc(-c3ccc(Cl)cc3)no2)C1]

The title compound was synthesised using a procedure similar to that described for Example 34. LCMS: Method A, 4.527 min, MS: ES+331.02; $^1$H NMR (400 MHz, DMSO-d6) δ ppm 11.77 (s, 1H), 7.86 (d, J=8.4 Hz, 2H), 7.52 (d, J=8.4 Hz, 2H), 6.74 (s, 1H), 3.50-3.54 (m, 1H), 3.39-3.42 (m, 1H), 3.34-3.36 (m, 1H), 3.03-3.07 (m, 1H), 2.53-2.64 (m, 3H), 1.99-2.02 (m, 1H), 1.54-1.59 (m, 1H).

Example 36 (R)—N-(3-(3-Chlorophenyl)isoxazol-5-yl)-2-(1-cyanopyrrolidin-3-yl)acetamide

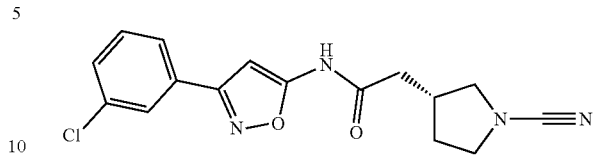

The title compound was synthesised using a procedure similar to that described for Example 34, using 3-(3-chlorophenyl)-3-oxopropanenitrile (CAS Number 21667-62-9) in step a. LCMS: Method A, 4.358 min, MS: ES+330.95; Chiral SFC: Method Z, 4.25 min; $^1$H NMR (400 MHz, DMSO-d6) δ ppm 11.82 (s, 1H), 7.92 (s, 1H), 7.83-7.85 (m, 1H), 7.51-7.59 (m, 2H), 6.83 (s, 1H), 3.53-3.55 (m, 1H), 3.42-3.47 (m, 1H), 3.35-3.39 (m, 1H), 3.06-3.10 (m, 1H), 2.56-2.60 (m, 3H), 1.99-2.08 (m, 1H), 1.55-1.65 (m, 1H).

Example 37 (S)—N-(3-(3-Methoxyphenyl)isoxazol-5-yl)-2-(1-cyanopyrrolidin-3-yl)acetamide

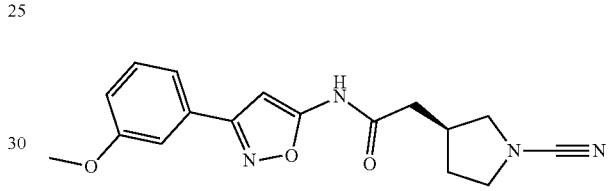

The title compound was synthesised using a procedure similar to that described for Example 34, steps b-d, using 3-(3-methoxyphenyl)isoxazol-5-amine (CAS Number 119162-46-8) in step b. LCMS: Method A, 3.937 min, MS: ES+327.03; Chiral SFC: Method Z, 4.73 min; $^1$H NMR (400 MHz, DMSO-d6) δ ppm 11.75 (s, 1H), 7.34-7.39 (m, 3H), 7.03-7.04 (m, 1H), 6.73 (s, 1H), 3.80 (s, 3H), 3.50-3.54 (m, 1H), 3.36-3.41 (m, 1H), 3.31-3.34 (m, 1H), 3.03-3.07 (m, 1H), 2.53-2.56 (m, 3H), 2.00-2.02 (m, 1H), 1.54-1.59 (m, 1H).

Example 38 (S)-3-(2-(3-(4-Methoxyphenyl)azetidin-1-yl)-2-oxoethyl)pyrrolidine-1-carbonitrile (Prepared according to general method A)

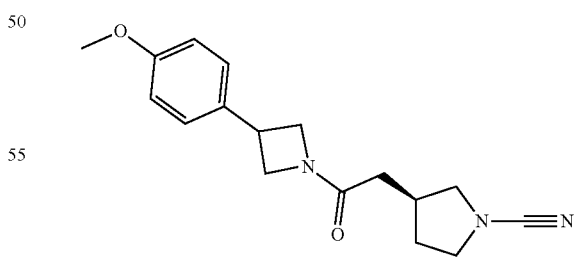

The title compound was synthesised using a procedure similar to that described for Example 1, using (S)-2-(1-(tert-butoxycarbonyl)pyrrolidin-3-yl)acetic acid (CAS Number 204688-61-9) in step a. LCMS: Method A, 3.226 min, MS: ES+300.1; Chiral SFC: Method Y, 4.62 min; $^1$H NMR (400 MHz, DMSO-d6) δ ppm 7.30 (d, J=8.4 Hz 2H), 6.93 (d, J=8.8 Hz 2H), 4.46-4.50 (m, 1H), 4.20-4.26 (m, 1H), 4.07-

4.09 (m, 1H), 3.75-3.80 (m, 5H), 3.50-3.54 (m, 1H), 3.43-3.46 (m, 2H), 3.00-3.04 (m, 1H), 2.43-2.49 (m, 1H), 2.17-2.30 (m, 2H), 1.99-2.06 (m, 1H), 1.53-1.58 (m, 1H).

Example 39 (S)-3-(2-(3-(4-Methoxy-3-(1H-pyrazol-5-yl)phenyl)azetidin-1-yl)-2-oxoethyl)pyrrolidine-1-carbonitrile DCM (27 ml) was added TFA (8.1 ml) drop-wise at 0° C. and the resulting mixture was stirred for 1 h at rt. The reaction mixture was concentrated under reduced pressure and was azeotopically distilled from DCM (3×20 ml) to obtain 3-(3-bromo-4-methoxyphenyl)azetidine TFA salt [3.500 g, 9.83 mmol (crude)]. LCMS: Method C, 1.284 min, MS: ES+242.2, 244.2.

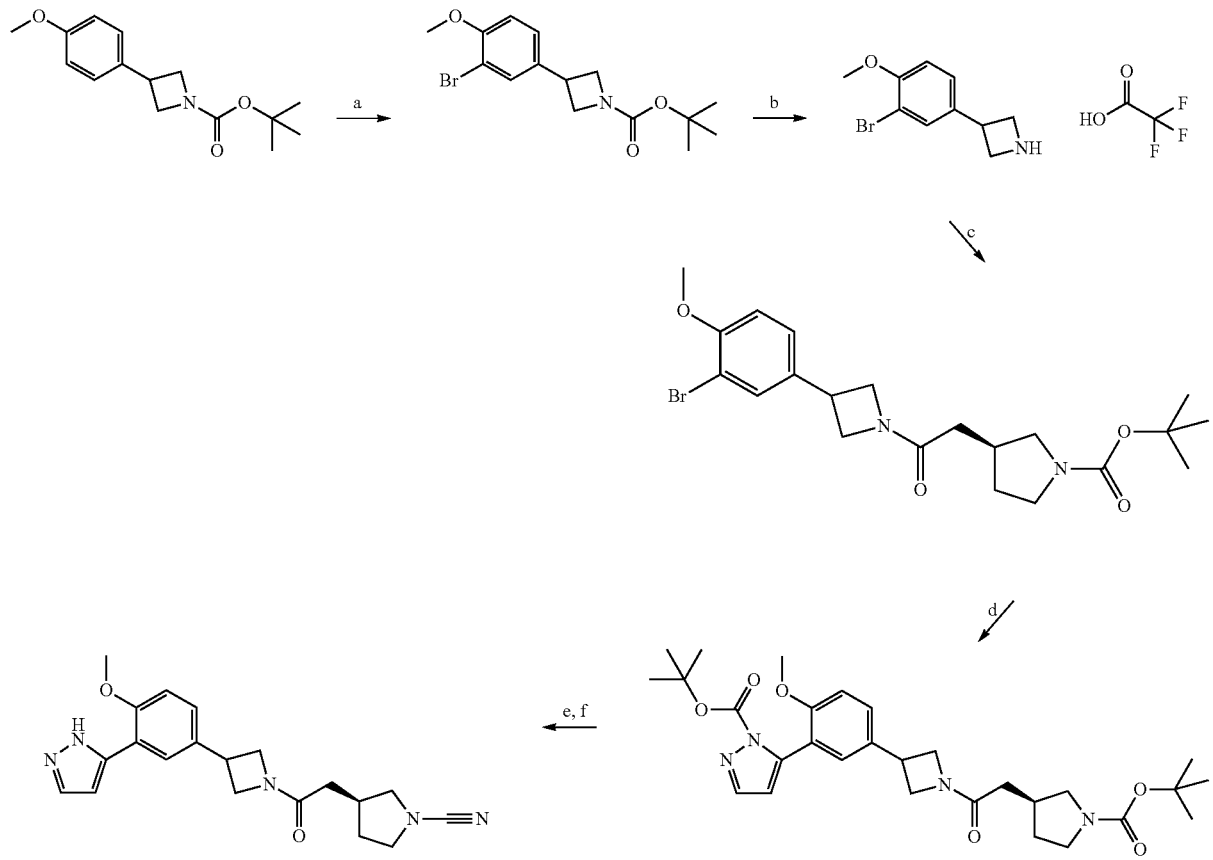

Step a

To a stirred solution of N-bromosuccimide (1.680 g, 9.51 mmol) in MeN (20 ml) was added a solution of tert-butyl 3-(4-methoxyphenyl)azetidine-1-carboxylate (Intermediate A, step a, 2.500 g, 9.51 mmol) in MeCN (5 ml) at 0° C. under inert atmosphere and then stirred at rt for 5 h. The reaction mixture was diluted with water (100 ml) and was extracted with EtOAc (2×100 ml). Combined organic extracts were dried over anhydrous sodium sulfate, filtered and concentrated under reduced pressure. The crude residue was purified by flash column chromatography (compound eluted in 10% EtOAc in hexane) to give tert-butyl 3-(3-bromo-4-methoxyphenyl)azetidine-1-carboxylate (2.700 g, 7.90 mmol). LCMS: Method C, 1.862 min, MS: ES+286.2, 288.2 (M-56), ¹H NMR (400 MHz, CDCl₃) δ ppm 7.54 (d, J=2.4 Hz, 1H), 7.26 (dd, J1=2.4 Hz, J2=8.8 Hz, 1H), 6.92 (d, J=8.4 Hz, 1H), 4.34 (t, J=8.8 Hz, 2H), 3.95-3.99 (m, 2H), 3.93 (s, 3H), 3.67-3.71 (m, 1H), 1.46 (s, 9H).

Step b

To a stirred solution of tert-butyl 3-(3-bromo-4-methoxyphenyl)azetidine-1-carboxylate (2.700 g, 7.90 mmol) in

Step c

To a stirred solution of (S)-2-(1-(tert-butoxycarbonyl)pyrrolidin-3-yl)acetic acid (0.643 g, 2.81 mmol) in DMF (7 ml) was added DIPEA (2.4 ml, 14.0 mmol) and HATU (1.600 g, 4.21 mmol) at 0° C. The resulting reaction mixture was stirred for 1 h at rt. The reaction mixture was cooled to 0° C. and a solution of 3-(3-bromo-4-methoxyphenyl)azetidine TFA salt (1.000 g, 2.80 mmol) in DMF (3 ml) was slowly added. Stirring continued for another at rt for a further 16 h. The reaction mixture was diluted with water (100 ml) and extracted into EtOAc (2×100 ml). Combined organic extracts were dried over anhydrous sodium sulfate, filtered and concentrated under reduced pressure. The resulting residue was purified by flash column chromatography (compound eluted in 95% EtOAc in hexane) to give tert-butyl (S)-3-(2-(3-(3-bromo-4-methoxyphenyl)azetidin-1-yl)-2-oxoethyl)pyrrolidine-1-carboxylate (0.850 g, 1.876 mmol). LCMS: Method C, 1.706 min, MS: ES+453.4/455.4.

Step d

To a mixture of tert-butyl (S)-3-(2-(3-(3-bromo-4-methoxyphenyl)azetidin-1-yl)-2-oxoethyl)pyrrolidine-1- carboxylate (0.270 g, 0.60 mmol) and (1-(tert-butoxycarbonyl)-1H-pyrazol-5-yl)boronic acid (0.151 g, 0.72 mmol) in 1,4-dioxane:water (6:1; 7 ml) was added K₂CO₃ (0.164 g, 1.19 mmol). Resulting mixture was degassed with nitrogen for 20 min before addition of PdCl₂(dppf) (0.043 g, 0.06 mmol) and the resulting reaction mixture was heated at 80° C. for 2 h. The resulting reaction mixture was cooled to rt, diluted with water (50 ml) and extracted into EtOAc (2×50 ml). Combined organic extracts were dried over anhydrous sodium sulfate, filtered and concentrated under reduced pressure. The crude residue was purified by flash column chromatography (compound eluted in 3% MeOH in DCM) to give tert-butyl (S)-5-(5-(1-(2-(1-(tert-butoxycarbonyl)pyrrolidin-3-yl)-2-methoxyphenyl)-1H-pyrazole-1-carboxylate (0.275 g, 0.51 mmol). LCMS: Method C, 1.828 min, MS: ES+541.6.

Step e

To a solution of tert-butyl (S)-5-(5-(1-(2-(1-(tert-butoxycarbonyl)pyrrolidin-3-yl)acetyl)-azetidin-3-yl)-2-methoxyphenyl)-1H-pyrazole-1-carboxylate (0.270 g, 0.61 mmol) in DCM (3 ml) was added TFA (1 mL) at 0° C. The reaction mixture was stirred at rt for 1 h. The resulting mixture was concentrated under reduced pressure to give residue, which was azeotopically distilled from DCM (3×10 ml) and dried under reduced pressure to obtain (S)-1-(3-(4-methoxy-3-(1H-pyrazol-5-yl)phenyl)-azetidin-1-yl)-2-(pyrrolidin-3-yl)ethan-1-one TFA salt (0.450 g, crude). LCMS: Method C, 1.263 min, MS: ES+241.5.

Step f

To a solution of (S)-1-(3-(4-methoxy-3-(1H-pyrazol-5-yl)phenyl)azetidin-1-yl)-2-(pyrrolidin-3-yl)ethan-1-one TFA salt (0.450 g, crude from previous step) in THF (5 ml) was cooled at 0° C. and added K₂CO₃ (0.683 g, 4.95 mmol). The reaction mixture was stirred at 0° C. for 15 min. Cyanogen bromide (0.105 g, 0.99 mmol) was added to reaction mixture at 0° C. and stirred for 45 min. The resulting reaction mixture was poured into water (50 ml) and extracted with EtOAc (2×50 ml). Combined organic extracts were dried over sodium sulphate and concentrated under reduced pressure. The crude residue was purified by column chromatography (compound eluted in 4% MeOH in DCM) to give (S)-3-(2-(3-(4-methoxy-3-(1H-pyrazol-5-yl)phenyl)azetidin-1-yl)-2-oxoethyl)pyrrolidine-1-carbonitrile (0.120 g, 0.33 mmol). LCMS: Method A, 2.90 min, MS: ES+366.22. ¹H NMR (400 MHz, DMSO-d6 with one drop of TFA) b ppm 7.89 (brs, 1H), 7.79 (d, J=2.0 Hz, 1H), 7.36 (d, J=8.4 Hz, 1H), 7.13 (d, J=8.4 Hz, 1H), 6.90 (brs, 1H), 4.52-4.48 (m, 1H), 4.28-4.24 (m, 1H), 4.15-4.11 (m, 1H), 3.89 (s, 3H), 3.86-3.83 (m, 2H), 3.52-3.50 (m, 1H), 3.45-3.40 (m, 1H), 3.36-3.30 (m, 1H), 3.04-2.99 (m, 1H), 2.31-2.18 (m, 2H), 2.06-2.00 (m, 1H), 1.60-1.52 (m, 1H), 1.23 (brs, 1H).

Example 40 (S)-3-(2-(3-(4-Methoxy-3-(1-methyl-1H-pyrazol-5-yl)phenyl)azetidin-1-yl)-2-oxoethyl)-pyrrolidine-1-carbonitrile

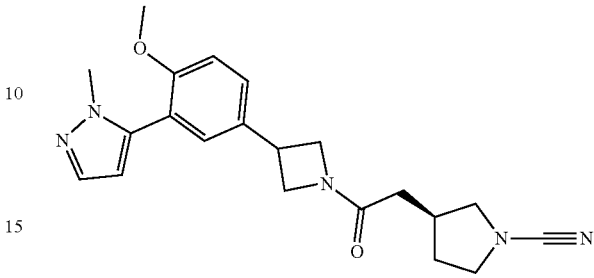

Step a

To a mixture of tert-butyl (S)-3-(2-(3-(3-bromo-4-methoxyphenyl)azetidin-1-yl)-2-oxoethyl)pyrrolidine-1-carboxylate (0.220 g, 0.49 mmol) and 1-methyl-5-(4,4,5,5-tetramethyl-1,3,2-dioxaborolan-2-yl)-1H-pyrazole (0.151 g, 0.73 mmol) in 1,4-dioxane:water mixture (2.5:1; 7 ml) was added K₂CO₃ (0.134 g, 0.97 mmol) at rt. The resulting mixture was degassed with nitrogen for 20 min before addition of PdCl₂(dppf) (0.035 g, 0.05 mmol) and the resulting mixture was heated at 100° C. for 6 h. The reaction was cooled to rt, diluted with water (30 ml) and extracted into EtOAc (2×30 ml). Combined organic extracts were dried over anhydrous sodium sulfate, filtered and concentrated under reduced pressure. The crude residue was purified by flash column chromatography (eluted with DCM) to obtain tert-butyl (S)-3-(2-(3-(4-methoxy-3-(1-methyl-1H-pyrazol-5-yl)phenyl)azetidin-1-yl)-2-oxo-ethyl)pyrrolidine-1-carboxylate (0.275 g, 0.61 mmol). LCMS: Method C, 1.577 min, MS: ES+455.47.

Step b

To a solution of tert-butyl (S)-5-(5-(1-(2-(1-(tert-butoxycarbonyl)pyrrolidin-3-yl)acetyl)-azetidin-3-yl)-2-methoxyphenyl)-1H-pyrazole-1-carboxylate (0.270 g, 0.59 mmol) in DCM (5 ml) was added TFA (1.4 ml) at 0° C. The reaction mixture was stirred at rt for 2 h. The resulting mixture was concentrated under reduced pressure to give residue, which was azeotopically distilled from DCM (3×15 ml) and dried under reduced pressure to obtain (S)-1-(3-(4-methoxy-3-(1-methyl-1H-pyrazol-5-yl)phenyl)azetidin-1-yl)-2-(pyrrolidin-3-yl)ethan-1-one TFA salt (0.400 g, crude). LCMS: Method C, 1.322 min, MS: ES+355.5.

Step c

To a solution of (S)-1-(3-(4-methoxy-3-(1-methyl-1H-pyrazol-5-yl)phenyl)azetidin-1-yl)-2-(pyrrolidin-3-yl)ethan-1-one TFA salt (0.395 g, 0.84 mmol, crude from previous step) in THF (7 ml) was cooled at 0° C. and added K₂CO₃ (0.582 g, 4.22 mmol). The reaction mixture was stirred at 0° C. for 5 min. Cyanogen bromide (0.089 g, 0.84 mmol) was added to reaction mixture at 0° C. and stirred for 20 min. The resulting reaction mixture was poured into water (30 ml) and extracted with EtOAc (2×30 ml). Combined organic extracts were dried over sodium sulphate and concentrated under reduced pressure. The crude residue was purified by column chromatography (compound eluted in 80%-100% EtOAc in hexane) to give (S)-3-(2-(3-(4-methoxy-3-(1-methyl-1H-pyrazol-5-yl)phenyl)azetidin-1-yl)-2-oxoethyl)pyrrolidine-1-carbonitrile (0.055 g, 0.15 mmol). LCMS: Method B, 3.267 min, MS: ES+380.48; $^1$H NMR (400 MHz, DMSO-d6) δ ppm 7.48-7.45 (m, 2H), 7.27 (s, 1H), 7.17 (d, J=8.4 Hz, 1H), 6.27 (s, 1H), 4.51-4.49 (m, 1H), 4.25-4.15 (m, 2H), 3.84-3.83 (m, 2H), 3.81 (s, 3H), 3.63 (s, 3H), 3.52-3.50 (m, 1H), 3.40-3.49 (m, 2H), 3.04-3.00 (m, 1H), 2.29-2.20 (m, 2H), 2.02 (brs, 1H), 1.59-1.53 (m, 1H).

The Examples in Table 4 were synthesised according to the methods described herein.

TABLE 4

| Example | Name |
| --- | --- |
| 41 | 2-(1-cyanopyrrolidin-3-yl)-N-(5-phenyl-1,3,4-thiadiazol-2-yl)acetamide |
| 42 | (S)-N-(3-(3-chlorophenyl)isoxazol-5-yl)-2-(1-cyanopyrrolidin-3-yl)acetamide |
| 43 | (R)-2-(1-cyanopyrrolidin-3-yl)-N-(3-(3-methoxyphenyl)isoxazol-5-yl)acetamide |
| 44 | 2-(1-cyanopyrrolidin-3-yl)-N-(pyrazolo[1,5-a]pyridin-2-yl)acetamide |
| 45 | 2-(1-cyanopyrrolidin-3-yl)-N-(4-(trifluoromethyl)pyridin-2-yl)acetamide |
| 46 | N-(5-cyanopyridin-2-yl)-2-(1-cyanopyrrolidin-3-yl)acetamide |
| 47 | 2-(1-cyanopyrrolidin-3-yl)-N-(1-(pyridin-2-yl)azetidin-3-yl)acetamide |
| 48 | (S)-N-(5-(3-chlorophenyl)-1,3,4-oxadiazol-2-yl)-2-(1-cyanopyrrolidin-3-yl)acetamide |
| 49 | N-(5-(3-cyanophenyl)-1,3,4-oxadiazol-2-yl)-2-(1-cyanopyrrolidin-3-yl)acetamide |
| 50 | (S)-N-(3-(3-chlorophenyl)isoxazol-5-yl)-2-((S)-1-cyanopyrrolidin-3-yl)propanamide |
| 51 | (R)-N-(3-(3-cyanophenyl)isoxazol-5-yl)-2-(1-cyanopyrrolidin-3-yl)acetamide |
| 52 | (S)-3-(2-(3-(4-cyanophenyl)azetidin-1-yl)-2-oxoethyl)pyrrolidine-1-carbonitrile |
| 53 | (R)-N-(3-(3-chlorophenyl)isoxazol-5-yl)-2-((S)-1-cyanopyrrolidin-3-yl)propanamide |
| 54 | (R)-2-(1-cyanopyrrolidin-3-yl)-N-(3-(3-(trifluoromethoxy)phenyl)isoxazol-5-yl)acetamide |
| 55 | (R)-N-(5-(3-cyanophenyl)isoxazol-3-yl)-2-(1-cyanopyrrolidin-3-yl)acetamide |
| 56 | (S)-3-(2-(3-(3-cyanophenyl)azetidin-1-yl)-2-oxoethyl)pyrrolidine-1-carbonitrile |
| 57 | (S)-6-(1-(2-(1-cyanopyrrolidin-3-yl)acetyl)azetidin-3-yl)nicotinonitrile |
| 58 | 3-(2-(3-(4-hydroxyphenyl)azetidin-1-yl)-2-oxoethyl)pyrrolidine-1-carbonitrile |
| 59 | (S)-3-(2-(3-(4-cyano-3-methylphenyl)azetidin-1-yl)-2-oxoethyl)pyrrolidine-1-carbonitrile |
| 60 | (S)-4-(1-(2-(1-cyanopyrrolidin-3-yl)acetyl)azetidin-3-yl)-N,N-dimethylbenzamide |
| 61 | (S)-3-(1-(3-(4-cyanophenyl)azetidin-1-yl)-1-oxopropan-2-yl)pyrrolidine-1-carbonitrile (Diastereomer 1) |
| 62 | (S)-3-(1-(3-(4-cyanophenyl)azetidin-1-yl)-1-oxopropan-2-yl)pyrrolidine-1-carbonitrile (Diastereomer 2) |
| 63 | (R)-2-(1-cyanopyrrolidin-3-yl)-N-(5-phenyl-1,3,4-thiadiazol-2-yl)acetamide |
| 64 | (S)-2-(1-cyanopyrrolidin-3-yl)-N-(5-phenyl-1,3,4-thiadiazol-2-yl)acetamide |
| 65 | (S)-3-(2-(3-(5-isopropoxypyridin-2-yl)azetidin-1-yl)-2-oxoethyl)pyrrolidine-1-carbonitrile |
| 66 | (S)-3-(2-(3-(4-(2-methoxyethoxy)phenyl)azetidin-1-yl)-2-oxoethyl)pyrrolidine-1-carbonitrile |
| 67 | (S)-3-(2-(3-(4-methoxy-3-(1-methyl-1H-pyrazol-4-yl)phenyl)azetidin-1-yl)-2-oxoethyl)pyrrolidine-1-carbonitrile |
| 68 | (S)-3-(2-(3-(2-fluoro-3-methoxyphenyl)azetidin-1-yl)-2-oxoethyl)pyrrolidine-1-carbonitrile |

Biological Activity of Compounds of the Invention
Abbreviations:
TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue
In Vitro USP30 Inhibition Assay
USP30 Biochemical Kinetic Assay.

Reactions were performed in duplicate in black 384 well plates (small volume, Greiner 784076) in a final reaction volume of 21 µl. USP30 CD (57-517, #64-0057-050 Ubiquigent) was diluted in reaction buffer (40 mM Tris, pH 7.5, 0.005% Tween 20, 0.5 mg/ml BSA, 5 mM beta-mercaptoethanol) to the equivalent of 0, 0.005, 0.01, 0.05, 0.1 and 0.5 µl/well. Buffer was optimised for optimal temperature, pH, reducing agent, salts, time of incubation, and detergent. Reactions were initiated by the addition of 50 nM of TAMRA labelled peptide linked to ubiquitin via an isopeptide bond as fluorescence polarisation substrate. Reactions were incubated at room temperature and read every 2 min for 120 min. Readings were performed on a Pherastar Plus (BMG Labtech). A Excitation 540 nm; A Emission 590 nm.

USP30 Biochemical IC50 Assay

Dilution plates were prepared at 21 times the final concentration (2100 µM for a final concentration of 100 µM) in 50% DMSO in a 96-well polypropylene V-bottom plate (Greiner #651201). A typical 8-point dilution series would be 100, 30, 10, 3, 1, 0.3, 0.1, 0.03 µM final. Reactions were performed in duplicate in black 384 well plates (small volume, Greiner 784076) in a final reaction volume of 21 µl. Either 1 µl of 50% DMSO or diluted compound was added to the plate. USP30 was diluted in reaction buffer (40 mM Tris, pH 7.5, 0.005% Tween 20, 0.5 mg/ml BSA, 5 mM beta-mercaptoethanol) to the equivalent of 0.05 µl/well and 10 µl of diluted USP30 was added to the compound. Enzyme and compound were incubated for 30 min at room temp. Reactions were initiated by the addition of 50 nM of TAMRA labelled peptide linked to ubiquitin via an isopeptide bond as fluorescence polarisation substrate. Reactions were read immediately after addition of substrate and following a 2 h incubation at room temperature. Readings were performed on a Pherastar Plus (BMG Labtech). A Excitation 540 nm; A Emission 590 nm.

Activity of Exemplary Compounds in USP30 biochemical IC50 assay Ranges:
0.001<A*<0.0.1 µM;
0.01<A<0.1 µM;
0.1<B<1 µM;
1<C<10 µM.

| Example | IC50 range |
| --- | --- |
| 1 | B |
| 2 | B |
| 3 | B |
| 4 | C |
| 5 | B |
| 6 | B |
| 7 | B |
| 8 | B |
| 9 | B |
| 10 | B |

-continued

| Example | IC50 range |
|---------|------------|
| 11 | C |
| 12 | B |
| 13 | B |
| 14 | B |
| 15 | C |
| 16 | C |
| 17 | B |
| 18 | B |
| 19 | B |
| 20 | B |
| 21 | C |
| 22 | A |
| 23 | B |
| 24 | B |
| 25 | B |
| 26 | B |
| 27 | B |
| 28 | B |
| 29 | B |
| 30 | B |
| 31 | C |
| 32 | B |
| 33 | B |
| 34 | B |
| 35 | B |
| 36 | A* |
| 37 | B |
| 38 | A |
| 39 | A |
| 40 | A |
| 41 | B |
| 42 | A |
| 43 | A |
| 44 | C |
| 45 | B |
| 46 | C |
| 47 | B |
| 48 | B |
| 49 | B |
| 50 | A* |
| 51 | A* |
| 52 | B |
| 53 | A |
| 54 | A* |
| 55 | A* |
| 56 | B |
| 57 | B |
| 58 | B |
| 59 | A |
| 60 | B |
| 61 | C |
| 62 | B |
| 63 | C |
| 64 | B |
| 65 | B |
| 66 | C |
| 67 | A |
| 68 | A |

The invention claimed is:

1. A compound of formula (I):

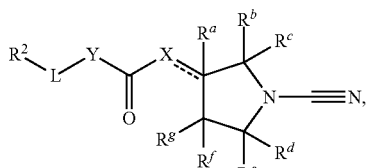

or a tautomer thereof, or a pharmaceutically acceptable salt of said compound or tautomer, wherein:

⸺ represents a single or double bond;

when ⸺ is a double bond, $R^a$ does not exist;

when ⸺ is a double bond, X represents $C(R^x)$;

when ⸺ is a single bond, X represents $C(R^x)(R^y)$;

$R^x$ and $R^y$ are each independently selected from hydrogen or optionally substituted $C_1$-$C_3$ alkyl;

or $R^x$ and $R^y$ together form an optionally substituted $C_3$-$C_6$ cycloalkyl ring;

$R^a$ is selected from hydrogen, fluoro, cyano, optionally substituted $C_1$-$C_3$ alkyl, optionally substituted $C_1$-$C_3$ alkoxy, or $R^a$ is linked to $R^b$ or $R^g$ to form an optionally substituted $C_3$-$C_4$ cycloalkyl ring;

$R^b$, $R^c$, $R^d$ and $R^e$ each independently represent hydrogen, an optionally substituted $C_1$-$C_3$ alkyl;

one or more spirocyclic groups where $R^b$ is linked to $R^c$, or $R^d$ is linked to $R^e$; or $R^b$ is linked to $R^a$ to form an optionally substituted $C_3$-$C_4$ cycloalkyl ring; or $R^e$ is linked to $R^f$ to form an optionally substituted $C_3$-$C_4$ cycloalkyl ring;

$R^f$ and $R^g$ are each independently selected from hydrogen, fluoro, cyano, optionally substituted $C_1$-$C_3$ alkyl, optionally substituted $C_1$-$C_3$ alkoxy, and optionally substituted 3 to 6 membered cycloalkyl, heterocyclyl, aryl or heteroaryl ring;

or $R^f$ is linked to $R^e$ to form an optionally substituted $C_3$-$C_4$ cycloalkyl ring;

or $R^g$ is linked to R to form an optionally substituted $C_3$-$C_4$ cycloalkyl ring;

or $R^g$ and $R^f$ together form a spirocyclic group;

Y is selected from $N(R^1)$, $N(R^1)$azetidinyl, and

wherein

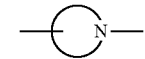

is a 4 to 10-membered monocyclic or bicyclic heterocyclyl ring;

L is selected from a covalent bond and a linking moiety;

$R^1$ is selected from hydrogen and optionally substituted $C_1$-$C_3$ alkyl;

$R^2$ is a 5 to 10-membered, monocyclic or bicyclic, aryl or heteroaryl ring, which may be unsubstituted or substituted with one or more $Q^1(R^3)_n$ which may be the same or different;

n is 0 or 1;

$Q^1$ is selected from $Q^{1a}$ and $Q^{1b}$;

$Q^{1a}$ is selected from halo, cyano, nitro, hydroxyl, $SR^4$, $NR^4R^5$, $CONR^4R^5$, $C_0$-$C_3$-alkylene-$NR^4COR^5$, $NR^4CONR^5R^6$, $COR^4$, $C(O)OR^4$, $S_2R^4$, $SO_2NR^4R^5$, $NR^4SO_2R^5$, $NR^4SO_2NR^5R^6$, $NR^4C(O)OR^5$, optionally substituted $C_1$-$C_6$ alkyl, optionally substituted $C_1$-$C_6$ alkoxy, optionally substituted halo($C_1$-$C_6$ alkyl), optionally substituted halo($C_1$-$C_6$ alkoxy), and optionally substituted $C_2$-$C_6$ alkenyl;

$Q^{1b}$ is selected from a covalent bond, an oxygen atom, a sulphur atom, $OR^7$, SO, $SO_2$, CO, $C(O)O$, $C_0$-$C_3$-alkylene-$C(O)NR^4$—$C_0$-$C_3$ alkylene, $C_0$-$C_3$-alkylene-$NR^4$—$C_0$-$C_3$ alkylene, $C_0$-$C_3$-alkylene-$NR^4C(O)$—$C_0$-$C_3$ alkylene, $NR^4CONR^5$, $SO_2NR^4$, $NR^4SO_2$, NR$^4$SO$_2$NR$^5$, NR$^4$C(O)O, NR$^4$C(O)OR$^7$, optionally substituted C$_1$-C$_6$ alkylene, and optionally substituted C$_2$-C$_6$ alkenylene;

R$^3$ is a 3 to 10 membered, monocyclic or bicyclic, heterocyclyl, heteroaryl, cycloalkyl, or aryl ring;

R$^4$, R$^5$ and R$^6$ are each independently selected from hydrogen and optionally substituted C$_1$-C$_6$ alkyl;

R$^7$ is optionally substituted C$_1$-C$_6$ alkylene;

wherein R$^3$ may be unsubstituted or substituted with one or more substituents selected from halo, cyano, oxo, nitro, hydroxyl, SR$^8$, optionally substituted C$_1$-C$_6$ alkyl, optionally substituted C$_1$-C$_6$ alkoxy, optionally substituted C$_2$-C$_6$ alkenyl, optionally substituted C$_2$-C$_6$ alkynyl, Q$^{2a}$-R$^{11}$, Q$^{2a}$-O-Q$^{2b}$-R$^{11}$, Q$^{2a}$-S-Q$^{2b}$-R$^{11}$, Q$^{2a}$-SO-Q$^{2b}$-R$^{11}$, Q$^{2a}$-NR$^8$CONR$^9$R$^{10}$, Q$^{2a}$-R$^8$CONR$^9$-Q$^{2a}$-R$^{11}$, Q$^{2a}$-NR$^8$R$^9$, Q$^{2a}$-NR$^8$-Q$^{2b}$-R$^{11}$, Q$^{2a}$-COR$^8$, Q$^{2a}$-CO-Q$^{2b}$-R$^{11}$, Q$^{2a}$-NR$^8$COR$^9$, Q$^{2a}$-NR$^8$CO-Q$^{2b}$-R$^{11}$, Q$^{2a}$-NR$^8$C(O)OR$^9$, Q$^{2a}$-NR$^8$C(O)O-Q$^{2b}$-R$^{11}$, Q$^{2a}$-SO$_2$R$^8$, Q$^{2a}$-SO$_2$-Q$^{2b}$-R$^{11}$, Q$^{2a}$-CONR$^8$R$^9$, Q$^{2a}$-CONR$^8$-Q$^{2b}$-R$^{11}$, Q$^{2a}$-CO$_2$R$^8$, Q$^{2a}$-CO$_2$-Q$^{2b}$-R$^{11}$, Q$^{2a}$-SO$_2$NR$^8$R$^9$, Q$^{2a}$-SO$_2$NR$^8$-Q$^{2b}$-R$^{11}$, Q$^{2a}$-NR$^8$SO$_2$R$^9$, Q$^{2a}$-NR$^8$SO$_2$-Q$^{2b}$-R$^{11}$, Q$^{2a}$-NR$^8$SO$_2$NR$^9$R$^{10}$, and Q$^{2a}$-NR$^8$SO$_2$NR$^9$-Q$^{2b}$-R$^{11}$;

Q$^{2a}$ and Q$^{2b}$ are each independently selected from a covalent bond, optionally substituted C$_1$-C$_6$ alkylene, and optionally substituted C$_2$-C$_6$ alkenylene;

R$^8$, R$^9$ and R$^{10}$ are each independently selected from hydrogen and optionally substituted C$_1$-C$_6$ alkyl;

and R$^{11}$ is an optionally substituted 3 to 10 membered heterocyclyl, heteroaryl, aryl or cycloalkyl ring.

2. The compound according to claim 1, wherein:

R$^x$ and R$^y$ are each independently selected from hydrogen and C$_1$-C$_3$ alkyl; or R$^x$ and R$^y$ together form a C$_3$-C$_6$ cycloalkyl ring;

R$^a$ is selected from hydrogen, fluoro, cyano, C$_1$-C$_3$ alkyl, and C$_1$-C$_3$ alkoxy;

or R$^a$ is linked to either R$^b$ or R$^g$ to form a C$_3$-C$_4$ cycloalkyl ring;

R$^b$, R$^c$, R$^d$ and R$^e$ each independently represent hydrogen, C$_1$-C$_3$ alkyl; one or more spirocyclic groups where R$^b$ is linked to R$^c$, or R$^d$ is linked to R$^e$; or R$^b$ is linked to R$^a$ to form a C$_3$-C$_4$ cycloalkyl ring; or R$^e$ is linked to R$^f$ to form a C$_3$-C$_4$ cycloalkyl ring;

R$^f$ and R$^g$ are each independently selected from hydrogen, fluoro, cyano, C$_1$-C$_3$ alkyl, C$_1$-C$_3$ alkoxy, and a 3 to 6 membered cycloalkyl, heterocyclyl, aryl or heteroaryl ring;

or R$^f$ is linked to R to form a C$_3$-C$_4$ cycloalkyl ring;

or R$^g$ is linked to R$^a$ to form a C$_3$-C$_4$ cycloalkyl ring;

or R$^g$ and R$^f$ together form a spirocyclic group;

Y is selected from N(R$^1$), N(R$^1$)azetidinyl, and

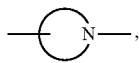

wherein

is a 4 to 10-membered, monocyclic or bicyclic, heterocyclyl ring; wherein said ring may be optionally substituted with one or more substituents independently selected from halo, oxo, cyano, C$_1$-C$_3$ alkyl, and C$_1$-C$_3$ alkoxy, wherein the alkyl and alkoxy may be optionally substituted with halo;

L is selected from a covalent bond, an oxygen atom, and C$_1$-C$_3$ alkylene, with the proviso that L cannot be an oxygen atom when Y represents N(R$^1$);

R$^1$ is selected from hydrogen and C$_1$-C$_3$ alkyl;

R$^2$ is a 5 to 10 membered, monocyclic or bicyclic, aryl or heteroaryl ring, which may be unsubstituted or substituted with one or more Q$^1$(R$^3$)$_n$ which may be the same or different;

n is 0 or 1;

when n is 0, Q$^1$ represents Q$^{1a}$; and when n is 1, Q$^1$ represents Q$^{1b}$;

Q$^{1a}$ is selected from halo, cyano, nitro, hydroxyl, SR$^4$, NR$^4$R$^5$, CONR$^4$R$^5$, C$_0$-C$_3$-alkylene-NR$^4$COR$^5$, NR$^4$CONR$^5$R$^6$, COR$^4$, C(O)OR$^4$, S$_2$R$^4$, SO$_2$NR$^4$R$^5$, NR$^4$SO$_2$R$^5$, NR$^4$SO$_2$NR$^5$R$^6$, NR$^4$C(O)OR$^5$, C$_1$-C$_6$ alkyl, C$_1$-C$_6$ alkoxy, halo(C$_1$-C$_6$ alkyl), halo(C$_1$-C$_6$ alkoxy), and C$_2$-C$_6$ alkenyl; wherein said alkyl, alkoxy and alkenyl may be unsubstituted or substituted with a group selected from C$_1$-C$_6$ alkoxy, halo, hydroxyl, thiol, cyano, amino, and nitro;

Q$^{1b}$ is selected from a covalent bond, an oxygen atom, a sulphur atom, OR$^7$, SO, SO$_2$, CO, C(O)O, C$_0$-C$_3$-alkylene-C(O)NR$^4$—C$_0$-C$_3$ alkylene, C$_0$-C$_3$-alkylene-NR$^4$—C$_0$-C$_3$ alkylene, C$_0$-C$_3$-alkylene-NR$^4$C(O)—C$_0$-C$_3$ alkylene, NR$^4$CONR$^5$, SO$_2$NR$^4$, NR$^4$SO$_2$, NR$^4$SO$_2$NR$^5$, NR$^4$C(O)O, NR$^4$C(O)OR$^7$, C$_1$-C$_6$ alkylene, and C$_2$-C$_6$ alkenylene;

R$^3$ is a 3 to 10 membered, monocyclic or bicyclic, heterocyclyl, heteroaryl, cycloalkyl, or aryl ring;

R$^4$, R$^5$ and R$^6$ are each independently selected from hydrogen and optionally substituted C$_1$-C$_6$ alkyl;

R$^7$ is optionally substituted C$_1$-C$_6$ alkylene;

wherein R$^3$ may be unsubstituted or substituted with one or more substituents selected from halo, cyano, oxo, nitro, hydroxyl, SR$^8$, C$_1$-C$_6$ alkyl, C$_1$-C$_6$ alkoxy, halo (C$_1$-C$_6$ alkyl), halo(C$_1$-C$_6$ alkoxy), C$_2$-C$_6$ alkenyl, C$_2$-C$_6$ alkynyl, Q$^{2a}$-R$^{11}$, Q$^{2a}$-S-Q$^{2b}$-R$^{11}$, Q$^{2a}$-S-Q$^{2b}$-R$^{11}$, Q$^{2a}$-SO-Q$^{2b}$-R$^{11}$, Q$^{2a}$-NR$^8$CONR$^9$R$^{10}$, Q$^{2a}$-NR$^8$CONR$^9$-Q$^{2a}$-R$^{11}$, Q$^{2a}$-NR$^8$R$^9$, Q$^{2a}$-NR$^8$-Q$^{2b}$-R$^{11}$, Q$^{2a}$-COR$^8$, Q$^{2a}$-CO-Q$^{2b}$-R$^{11}$, Q$^{2a}$-NR$^8$COR$^9$, Q$^{2a}$-NR$^8$CO-Q$^{2b}$-R$^{11}$, Q$^{2a}$-NR$^8$C(O)OR$^9$, Q$^{2a}$-NR$^8$C(O)O-Q$^{2b}$-R$^{11}$, Q$^{2a}$-SO$_2$R$^8$, Q$^{2a}$-SO$_2$-Q$^{2b}$-R$^{11}$, Q$^{2a}$-CONR$^8$R$^9$, Q$^{2a}$-CONR$^8$-Q$^{2b}$-R$^{11}$, Q$^{2a}$-CO$_2$R$^8$, Q$^{2a}$-CO$_2$-Q$^{2b}$-R$^{11}$, Q$^{2a}$-SO$_2$NR$^8$R$^9$, Q$^{2a}$-SO$_2$NR$^8$-Q$^{2b}$-R$^{11}$, Q$^{2a}$-NR$^9$SO$_2$R$^9$, Q$^{2a}$-NR$^9$SO$_2$-Q$^{2b}$-R$^{11}$, Q$^{2a}$-NR$^8$SO$_2$NR$^9$R$^{10}$, and Q$^{2a}$-NR$^8$SO$_2$NR$^9$-Q$^{2b}$-R$^{11}$;

Q$^{2a}$ and Q$^{2b}$ are each independently selected from a covalent bond, C$_1$-C$_6$ alkylene, and C$_2$-C$_6$ alkenylene;

R$^8$, R$^9$ and R$^{10}$ are each independently selected from hydrogen and C$_1$-C$_6$ alkyl;

and R$^{11}$ is a 3 to 10 membered, heterocyclyl, heteroaryl, aryl or cycloalkyl ring.

3. The compound according to claim 2, wherein R$^2$ is selected from thiazolyl, imidazopyridinyl, phenyl, pyridinyl, benzothiazolyl, isoxazolyl, benzoxazolyl, quinolinyl, pyrazolyl, thiadiazolyl, oxadiazolyl, and pyrazolopyridine;

each of which may be unsubstituted or substituted with one or more Q$^1$(R$^3$)$_n$ which may be the same or different.

4. The compound according to claim 1, wherein Q$^{1a}$ is selected from halo, cyano, hydroxyl, C$_1$-C$_6$ alkyl, C$_1$-C$_6$ alkoxy, halo(C$_1$-C$_6$ alkyl), and halo(C$_1$-C$_6$ alkoxy), C$_1$-C$_3$ alkoxy-C$_1$-C$_3$ alkyl, and C$_1$-C$_3$ alkoxy-C$_1$-C$_3$ alkoxy.

5. The compound according to claim 4, wherein $Q^{1a}$ is selected from halo, cyano, hydroxyl, $C_1$-$C_3$ alkyl, $C_1$-$C_3$ alkoxy, halo($C_1$-$C_3$ alkyl), and $C_1$-$C_3$ alkoxy-$C_1$-$C_3$ alkoxy.

6. The compound according to claim 1, wherein $Q^{1b}$ is selected from a covalent bond and an oxygen atom.

7. The compound according to claim 1, wherein $R^3$ is selected from phenyl, isoxazolyl, pyridinyl, pyrrolidinyl, and pyrazolyl.

8. The compound according to claim 1, wherein $R^3$ is unsubstituted or substituted with 1, 2, or 3 substituents, each independently selected from halo, cyano, oxo, nitro, hydroxyl, $SR^8$, $C_1$-$C_6$ alkyl, $C_1$-$C_6$ alkoxy, halo($C_1$-$C_6$ alkyl), halo($C_1$-$C_6$ alkoxy), $C_2$-$C_6$ alkenyl, and $C_2$-$C_6$ alkynyl.

9. The compound according to claim 1, wherein Y is selected from azetidinyl, N(H)azetidinyl, N(H), and N(CH$_3$).

10. The compound according to claim 1, wherein $R^a$, $R^b$, $R^c$, $R^d$, $R^e$, $R^f$ and $R^g$, $R^x$, and $R^y$, are each independently selected from hydrogen and methyl.

11. The compound according to claim 10, wherein $R^a$, $R^b$, $R^c$, $R^d$, $R^e$, $R^f$ and $R^g$ are hydrogen.

12. The compound according to claim 10, wherein $R^x$ and $R^y$ are hydrogen.

13. The compound according to claim 1, which is selected from:
3-(2-(3-(4-methoxyphenyl)azetidin-1-yl)-2-oxoethyl)pyrrolidine-1-carbonitrile;
N-(3-chlorophenyl)-2-(1-cyanopyrrolidin-3-yl)acetamide;
2-(1-cyanopyrrolidin-3-yl)-N-(6-methoxybenzo[d]thiazol-2-yl)acetamide;
2-(1-cyanopyrrolidin-3-yl)-N-(6-(trifluoromethyl)pyridin-3-yl)acetamide;
N-(6-chlorobenzo[d]thiazol-2-yl)-2-(1-cyanopyrrolidin-3-yl)acetamide;
2-(1-cyanopyrrolidin-3-yl)-N-(3-phenylisoxazol-5-yl)acetamide;
2-(1-cyanopyrrolidin-3-yl)-N-(5-phenylpyridin-2-yl)acetamide;
N-(5-chlorobenzo[d]oxazol-2-yl)-2-(1-cyanopyrrolidin-3-yl)acetamide;
2-(1-cyanopyrrolidin-3-yl)-N-(3,4-dichlorophenyl)acetamide;
2-(1-cyanopyrrolidin-3-yl)-N-(5-phenylthiazol-2-yl)acetamide;
2-(1-cyanopyrrolidin-3-yl)-N-phenethylacetamide;
3-(2-oxo-2-(3-phenoxyazetidin-1-yl)ethyl)pyrrolidine-1-carbonitrile;
3-(2-(3-(3-methoxyphenyl)azetidin-1-yl)-2-oxoethyl)pyrrolidine-1-carbonitrile;
3-(2-(3-(3,4-difluorophenyl)azetidin-1-yl)-2-oxoethyl)pyrrolidine-1-carbonitrile;
3-(2-(3-(2-methylpyridin-4-yl)azetidin-1-yl)-2-oxoethyl)pyrrolidine-1-carbonitrile;
2-(1-cyanopyrrolidin-3-yl)-N-(6-(3,5-dimethylisoxazol-4-yl)imidazo[1,2-a]pyridin-2-yl)acetamide;
3-(2-(3-(4-methoxyphenyl)azetidin-1-ylidene)pyrrolidine-1-carbonitrile;
3-(2-oxo-2-(3-phenylazetidin-1-yl)ethylidene)pyrrolidine-1-carbonitrile;
N-(3-chloro-4-methylphenyl)-2-(1-cyanopyrrolidin-3-ylidene)acetamide;
N-(4-chloro-3-(trifluoromethyl)phenyl)-2-(1-cyanopyrrolidin-3-ylidene)acetamide;
N-(benzo[d]thiazol-6-yl)-2-(1-cyanopyrrolidin-3-ylidene)acetamide;
2-(1-cyanopyrrolidin-3-ylidene)-N-(4-phenoxyphenyl)acetamide;
2-(1-cyanopyrrolidin-3-ylidene)-N-(quinolin-3-yl)acetamide;
2-(1-cyanopyrrolidin-3-ylidene)-N-methyl-N-(quinolin-6-ylmethyl)acetamide;
2-(1-cyanopyrrolidin-3-ylidene)-N-methyl-N-((5-phenylisoxazol-3-yl)methyl)acetamide;
2-(1-cyanopyrrolidin-3-ylidene)-N-methyl-N-(3-(pyridin-4-yl)benzyl)acetamide;
2-(1-cyanopyrrolidin-3-ylidene)-N-methyl-N-((3-phenylisoxazol-5-yl)methyl)acetamide;
2-(1-cyanopyrrolidin-3-ylidene)-N-methyl-N-(4-(pyrrolidin-1-yl)benzyl)acetamide;
2-(1-cyanopyrrolidin-3-ylidene)-N-methyl-N-((2-phenylthiazol-4-yl)methyl)acetamide;
2-(1-cyanopyrrolidin-3-ylidene)-N-methyl-N-((5-phenyl-1H-pyrazol-3-yl)methyl)acetamide;
2-(1-cyanopyrrolidin-3-ylidene)-N-(2-fluoro-5-(trifluoromethyl)benzyl)acetamide;
N-(benzo[d]thiazol-2-yl)-2-(1-cyanopyrrolidin-3-ylidene)-N-methylacetamide;
2-(1-cyanopyrrolidin-3-ylidene)-N-(3,4-dichlorobenzyl)-N-methylacetamide;
(S)—N-(3-(4-chlorophenyl)isoxazol-5-yl)-2-(1-cyanopyrrolidin-3-yl)acetamide;
(R)—N-(3-(4-chlorophenyl)isoxazol-5-yl)-2-(1-cyanopyrrolidin-3-yl)acetamide;
(R)—N-(3-(3-chlorophenyl)isoxazol-5-yl)-2-(1-cyanopyrrolidin-3-yl)acetamide;
(S)-2-(1-cyanopyrrolidin-3-yl)-N-(3-(3-methoxyphenyl)isoxazol-5-yl)acetamide;
2-(1-cyanopyrrolidin-3-yl)-N-(5-phenyl-1,3,4-thiadiazol-2-yl)acetamide;
(S)—N-(3-(3-chlorophenyl)isoxazol-5-yl)-2-(1-cyanopyrrolidin-3-yl)acetamide;
(R)-2-(1-cyanopyrrolidin-3-yl)-N-(3-(3-methoxyphenyl)isoxazol-5-yl)acetamide;
2-(1-cyanopyrrolidin-3-yl)-N-(pyrazolo[1,5-a]pyridin-2-yl)acetamide;
2-(1-cyanopyrrolidin-3-yl)-N-(4-(trifluoromethyl)pyridin-2-yl)acetamide;
N-(5-cyanopyridin-2-yl)-2-(1-cyanopyrrolidin-3-yl)acetamide;
2-(1-cyanopyrrolidin-3-yl)-N-(1-(pyridin-2-yl)azetidin-3-yl)acetamide;
(S)—N-(5-(3-chlorophenyl)-1,3,4-oxadiazol-2-yl)-2-(1-cyanopyrrolidin-3-yl)acetamide;
N-(5-(3-cyanophenyl)-1,3,4-oxadiazol-2-yl)-2-(1-cyanopyrrolidin-3-yl)acetamide;
(S)—N-(3-(3-chlorophenyl)isoxazol-5-yl)-2-((S)-1-cyanopyrrolidin-3-yl)propenamide;
(R)—N-(3-(3-cyanophenyl)isoxazol-5-yl)-2-(1-cyanopyrrolidin-3-yl)acetamide;
(S)-3-(2-(3-(4-cyanophenyl)azetidin-1-yl)-2-oxoethyl)pyrrolidine-1-carbonitrile;
(R)—N-(3-(3-chlorophenyl)isoxazol-5-yl)-2-((S)-1-cyanopyrrolidin-3-yl)propenamide;
(R)-2-(1-cyanopyrrolidin-3-yl)-N-(3-(3-(trifluoromethoxy)phenyl)isoxazol-5-yl)acetamide;
(R)—N-(5-(3-cyanophenyl)isoxazol-3-yl)-2-(1-cyanopyrrolidin-3-yl)acetamide;
(S)-3-(2-(3-(3-cyanophenyl)azetidin-1-yl)-2-oxoethyl)pyrrolidine-1-carbonitrile;
(S)-6-(1-(2-(1-cyanopyrrolidin-3-yl)acetyl)azetidin-3-yl)nicotinonitrile;

(S)-3-(2-(3-(4-methoxyphenyl)azetidin-1-yl)-2-oxoethyl)pyrrolidine-1-carbonitrile;
3-(2-(3-(4-hydroxyphenyl)azetidin-1-yl)-2-oxoethyl)pyrrolidine-1-carbonitrile;
(S)-3-(2-(3-(4-cyano-3-methylphenyl)azetidin-1-yl)-2-oxoethyl)pyrrolidine-1-carbonitrile;
(S)-4-(1-(2-(1-cyanopyrrolidin-3-yl)acetyl)azetidin-3-yl)-N,N-dimethylbenzamide;
(S)-3-((S)-1-(3-(4-cyanophenyl)azetidin-1-yl)-1-oxopropan-2-yl)pyrrolidine-1-carbonitrile;
(S)-3-((R)-1-(3-(4-cyanophenyl)azetidin-1-yl)-1-oxopropan-2-yl)pyrrolidine-1-carbonitrile;
(R)-2-(1-cyanopyrrolidin-3-yl)-N-(5-phenyl-1,3,4-thiadiazol-2-yl)acetamide;
(S)-2-(1-cyanopyrrolidin-3-yl)-N-(5-phenyl-1,3,4-thiadiazol-2-yl)acetamide;
(S)-3-(2-(3-(5-isopropoxypyridin-2-yl)azetidin-1-yl)-2-oxoethyl)pyrrolidine-1-carbonitrile;
(S)-3-(2-(3-(4-(2-methoxyethoxy)phenyl)azetidin-1-yl)-2-oxoethyl)pyrrolidine-1-carbonitrile;
(S)-3-(2-(3-(4-methoxy-3-(1H-pyrazol-5-yl)phenyl)azetidin-1-yl)-2-oxoethyl)pyrrolidine-1-carbonitrile;
(S)-3-(2-(3-(4-methoxy-3-(1-methyl-1H-pyrazol-5-yl)phenyl)azetidin-1-yl)-2-oxoethyl)pyrrolidine-1-carbonitrile;
(S)-3-(2-(3-(4-methoxy-3-(1-methyl-1H-pyrazol-4-yl)phenyl)azetidin-1-yl)-2-oxoethyl)pyrrolidine-1-carbonitrile; and
(S)-3-(2-(3-(2-fluoro-3-methoxyphenyl)azetidin-1-yl)-2-oxoethyl)pyrrolidine-1-carbonitrile;
or a tautomer thereof, or a pharmaceutically acceptable salt of said compound or tautomer.

14. The compound according to claim 1, a tautomer thereof, or a pharmaceutically acceptable salt of said compound or tautomer, for use as a medicament.

15. A method of inhibiting USP30 in a mammal, comprising administering to said mammal a therapeutically effective amount of a compound according to claim 1, or a tautomer thereof, or a pharmaceutically acceptable salt of said compound or tautomer.

16. A pharmaceutical composition, comprising a compound of formula (I) according to claim 1, or a pharmaceutically acceptable salt of said compound or tautomer, together with a pharmaceutically acceptable diluent or carrier.

17. A process for the preparation of a compound of formula (I) or a pharmaceutically acceptable salt thereof as defined in claim 1, which comprises the steps of reacting an amine of formula (II) with cyanogen bromide:

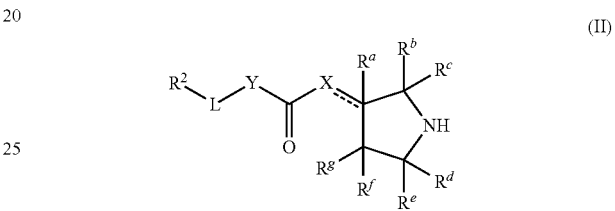

(II)

wherein $R^a$, $R^b$, $R^c$, $R^d$, $R^e$, $R^f$, $R^g$, X, Y, L and $R^2$ are as defined in claim 1.

* * * * *

UNITED STATES PATENT AND TRADEMARK OFFICE
CERTIFICATE OF CORRECTION

PATENT NO. : 11,014,912 B2
APPLICATION NO. : 16/334836
DATED : May 25, 2021
INVENTOR(S) : Stockley et al.

Page 1 of 1

It is certified that error appears in the above-identified patent and that said Letters Patent is hereby corrected as shown below:

In the Claims

At Column 62, Line 21, "R9" should be "Rg."

At Column 62, Line 28, "R" should be "Ra."

At Column 63, Line 16, "Q2a-R8CONR9-" should be "Q2a-NR8CONR9-."

At Column 63, Line 49, "R" should be "Re."

At Column 64, Line 41, "Q2a-S-Q2b-R11" should be "Q2a-O-Q2b-R11."

At Column 64, Line 49, "Q2a-NR9SO2R9" should be "Q2a-NR8SO2R9."

At Column 64, Line 49, "Q2a-NR9SO2-Q2b-R11" should be "Q2a-NR8SO2-Q2b-R11."

Signed and Sealed this
Twenty-fourth Day of May, 2022

Katherine Kelly Vidal
*Director of the United States Patent and Trademark Office*